US012698480B2

(12) United States Patent
Taniguchi et al.

(10) Patent No.: US 12,698,480 B2
(45) Date of Patent: *Aug. 4, 2026

(54) FORMATION OF THREE-DIMENSIONAL ORGAN FROM PLURIPOTENT STEM CELLS

(71) Applicant: Public University Corporation Yokohama City University, Yokohama (JP)

(72) Inventors: Hideki Taniguchi, Yokohama (JP); Takanori Takebe, Yokohama (JP)

(73) Assignee: Public University Corporation Yokohama City University, Yokohama (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/670,347

(22) Filed: May 21, 2024

(65) Prior Publication Data

US 2024/0301361 A1 Sep. 12, 2024

Related U.S. Application Data

(60) Continuation-in-part of application No. 16/768,019, filed as application No. PCT/JP2018/044144 on Nov. 30, 2018, now Pat. No. 12,012,616, and a continuation-in-part of application No. 15/296,912, filed on Oct. 18, 2016, now abandoned, which is a division of application No. 14/347,482, filed as application No. PCT/JP2012/074840 on Sep. 27, 2012, now Pat. No. 11,326,150.

(30) Foreign Application Priority Data

Sep. 27, 2011 (JP) ................................. 2011-210157
Nov. 30, 2017 (JP) ................................. 2017-230647

(51) Int. Cl.
*C12N 5/071* (2010.01)
*A01K 67/0271* (2024.01)
*A61L 27/38* (2006.01)

(52) U.S. Cl.
CPC ........ *C12N 5/0697* (2013.01); *A01K 67/0271* (2013.01); *A61L 27/3808* (2013.01); *A61L 27/3834* (2013.01); *A61L 27/3839* (2013.01); *A61L 27/3886* (2013.01); *A01K 2207/12* (2013.01); *A61L 2430/28* (2013.01); *C12N 2506/45* (2013.01)

(58) Field of Classification Search
CPC .............. C12N 5/0697; C12N 2506/45; A01K 67/0271; A01K 2207/12; A61L 27/3808; A61L 27/3834; A61L 27/3839; A61L 27/3886; A61L 2430/28
See application file for complete search history.

(56) References Cited

PUBLICATIONS

Abbasalizadeh et al., Continuous production of highly functional vascularized hepatobiliary organoids from human pluripotent stem cells using a scalable microfluidic platform. Advanced Functional Materials, vol. 33, No. 49 (2023) 2210233.*
Takebe et al., Massive and reproducible production of liver buds entirely from human pluripotent stem cells. Cell Reports, vol. 21, No. 10 (Dec. 5, 2017) pp. 2661-2670.*
Takebe et al., (2014) Generation of a vascularized and functional liver from an iPSC-derived organ bud transplant. Nature Protocols, 9: pp. 396-409 (Year: 2014).*

* cited by examiner

*Primary Examiner* — Kara D Johnson
(74) *Attorney, Agent, or Firm* — Morgan, Lewis & Bockius LLP

(57) ABSTRACT

The present disclosure relates to an organ bud and a method of preparing an organ bud.

16 Claims, 63 Drawing Sheets

Figure1. Scalable liver bud production and differentiation by developing an omni-well-array platform.

Figure2. Reverse optimization of human iPSC derived liver bud forming multiple progenitors.

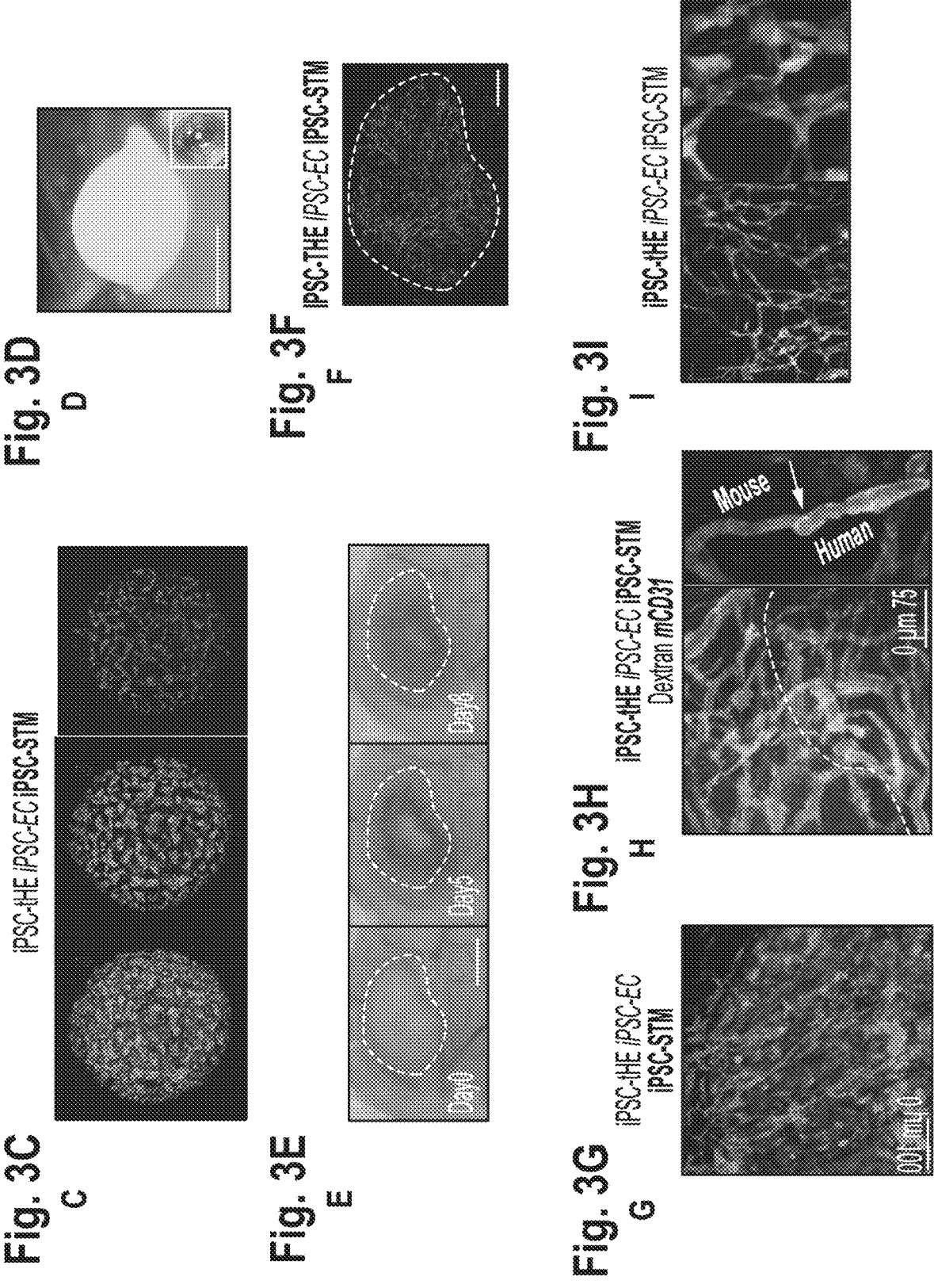

F

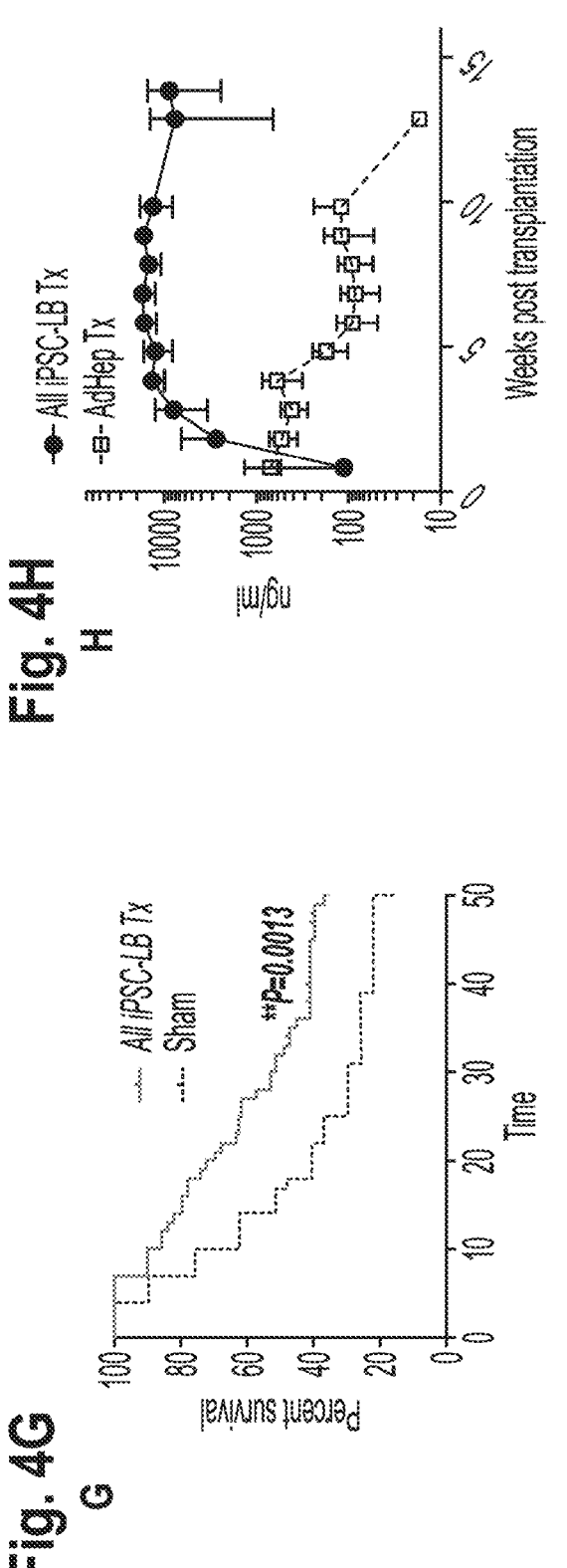
Fig. 4H
Fig. 4G
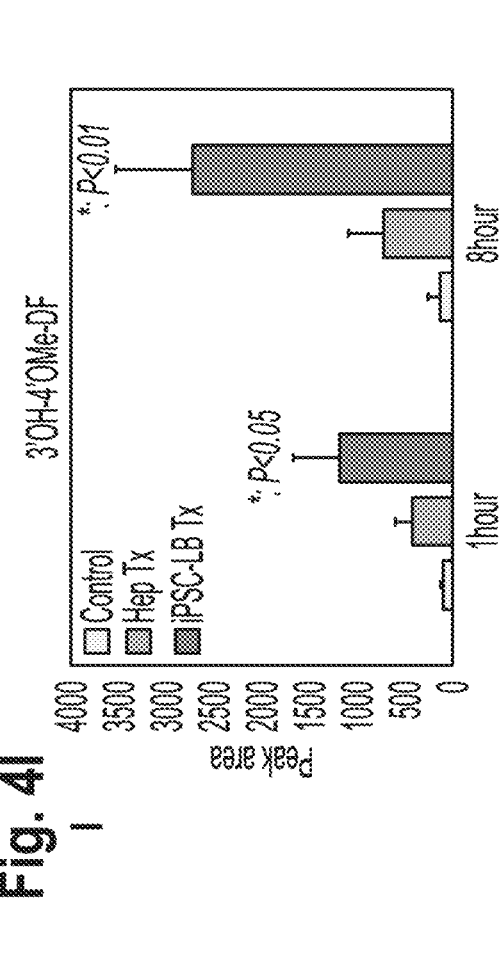
Fig. 4I

Figure S1 Coating optimization and collection of mass produced liver buds

A

B

Figure S2 Cell dose- and mixture ratio-dependent studies for generating LBs

Figure S3 Establishment of the omni-well plate for large-scale production .

Figure S4 Optimization of iPSC-derived endodermal cell induction protocol

Figure S5 Optimization of iPSC-derived liver bud generation protocols

Figure S6 Identification of TBX3 and ADRA1B as a marker for iPSC-tHE

A

B

Figure S7. Highly efficient differentiation into primitive endothelial progenitors from feeder free human iPSC

Figure S8. In vivo functionalization of human iPSC liver buds.

Revised Method

Fig. 21

Independent Culture Group

Coculture Group 60 hr (high-power field)          250μm

Arrowheads: reconstitution of vascular networks around pancreatic β cell-derived spheroid

GFP-HUVEC/AO 0 hr (high-power field)

Circles: vessel-like luminal structures formed by vascular endothelial cells

Fig. 27

Normal pancreatic islets

Transplant

Mouse brain

Insulin

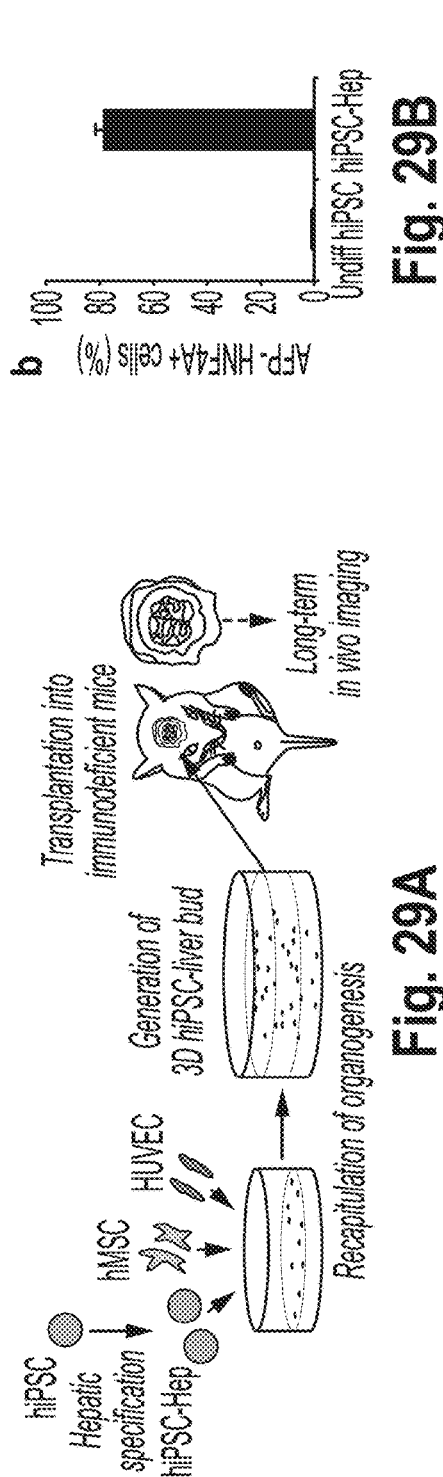
Fig. 29A
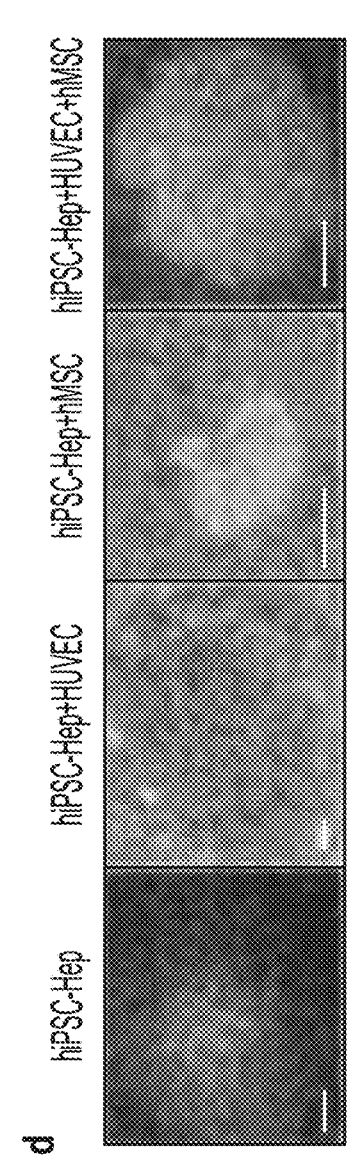
Fig. 29B
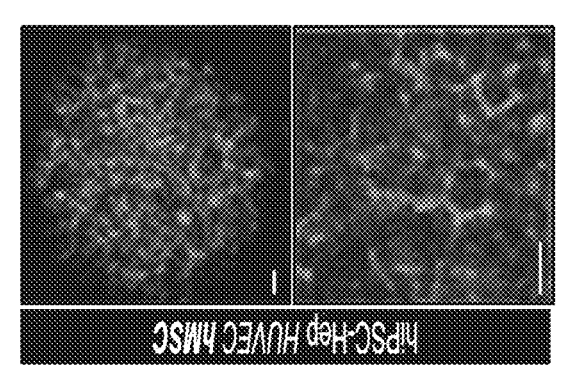
Fig. 29C
Fig. 29D

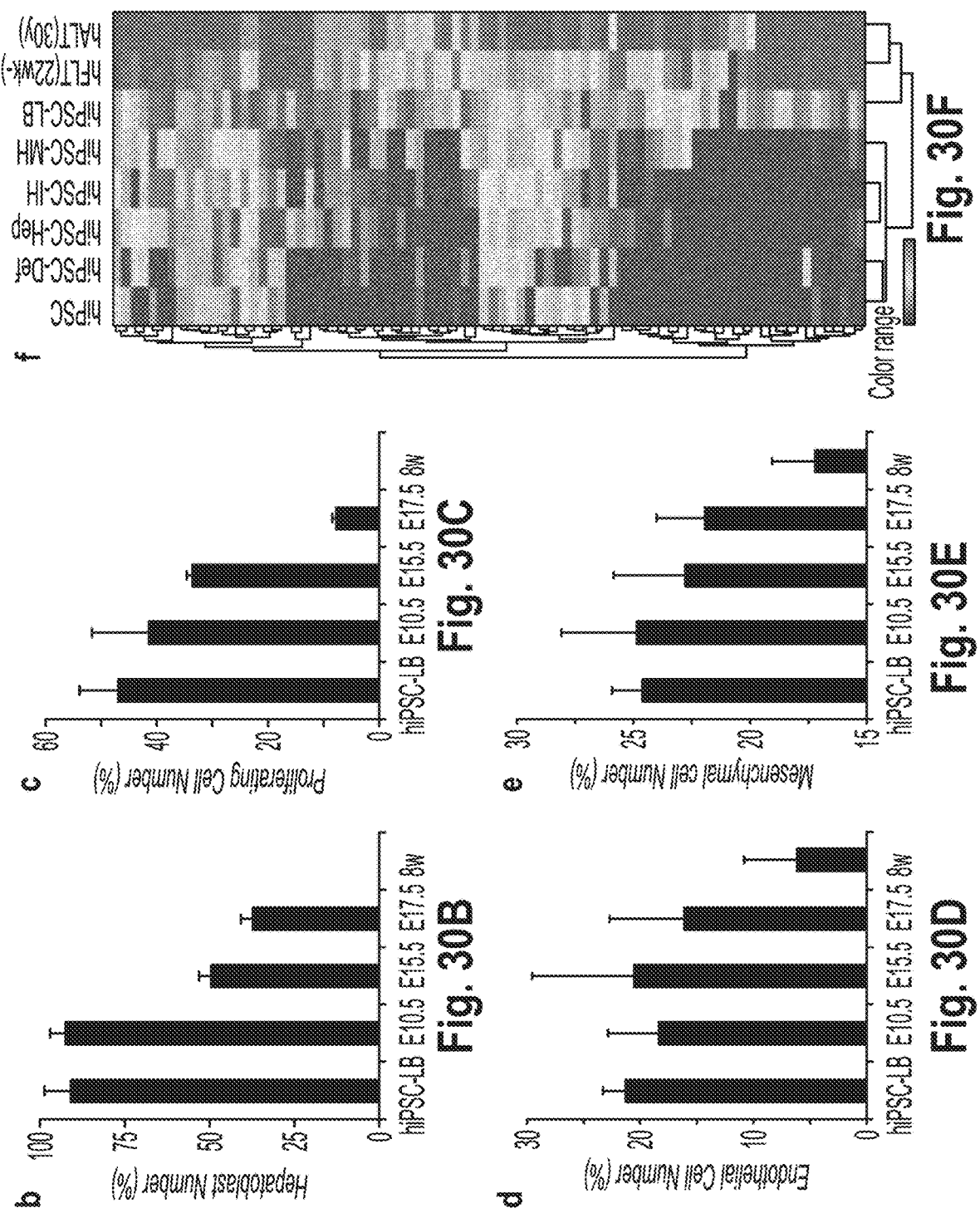

a b b transplants (●), human adult liver (●) and native hiPSCs (●).

FORMATION OF THREE-DIMENSIONAL ORGAN FROM PLURIPOTENT STEM CELLS

TECHNICAL FIELD

The present disclosure relates to construction of three-dimensional organs from pluripotent stem cells.

BACKGROUND ART

The preset inventors have developed a method of preparing three-dimensional tissues (organ primordia) by mixing functional cells used in regenerative medicine, etc. (such as pluripotent stem cell-derived organ cells) with umbilical cord-derived vascular endothelial cells and bone marrow-derived mesenchymal cells; and reported that organ primordia prepared by this method are superior to those cells obtained by directed differentiation under plane culture, in terms of function in vitro and therapeutic effects for disease model animals (Non-Patent Document No. 1: Nature 2013; Non-Patent Document No. 2: Cell Stem Cell 2015; Patent Documents Nos. 1 and 2).

PRIOR ART LITERATURE

Non-Patent Documents

Non-Patent Document No. 1: Takebe T et al., Nature 499, pp 481-484, 2013
Non-Patent Document No. 2: Takebe T et al., Cell Stem Cell 16, pp 556-565, 2015

Patent Documents

Patent Document No. 1: WO2013/047639
Patent Document No. 2: WO2015/012158

DISCLOSURE OF THE INVENTION

Problem for Solution by the Invention

Conventional methods using two types of cells, one derived from umbilical cord and the other from bone marrow, have the following problems which are ultimate challenges for practical application: (1) the quality of resultant organ primordia varies greatly depending on donors; (2) the growth capacities of cell sources are limited; and (3) it is difficult to secure immunocompatibility because cells are derived from different sources. Moreover, since umbilical cord/bone marrow-derived cells are highly matured cells, they greatly differ in differentiation stage from the immature cells required for generation of organ primordia, and largely depart from the scenario of in vivo development.

Moreover, conventional methods of directed differentiation using pluripotent stem cells are attempts to induce cell differentiation with a various combination of differentiation factors such as addition of humoral factors, gene transfer, etc. However, with these conventional methods, it is impossible to induce terminally differentiated functional cells. Furthermore, even the induction of early differentiation into tissue stem cells (i.e., progenitor populations of functional cells) has not been sufficiently achieved by those methods.

On the other hand, cells constituting tissues and organs comprise not only functional cells but also a plurality of cell species such as vascular cells and mesenchymal cells. Such cells take an orderly spatial arrangement, which generates coordinate interactions. As a result, a tissue structure is formed. However, at present, only a method using a support such as scaffolding is available as a technique to reconstitute human tissues and organs. This method has the following problems. Seeded functional cells have an extremely low engraft rate, and long-term culture of them is difficult. Further, the function of reconstituted tissue/organ is extremely immature.

Means to Solve the Problem

The present inventors have succeeded in preparing organ primordia from differentiation stage-synchronized multiple immature cells by ensuring that all three cell species used to prepare three-dimensional organ primordia are made from induced pluripotent stem cells (iPS cells). Specifically, the present inventors have prepared human liver buds using a combination of iPS cell-derived hepatic endoderm cells, iPS cell-derived vascular endothelial cells and iPS cell-derived mesenchymal cells, and compared them with those human liver buds which are prepared by conventional methods using a combination of iPS cell-derived hepatic endoderm cells, umbilical cord-derived vascular endothelial cells and bone marrow-derived mesenchymal cells, in terms of in vitro albumin secretion capacity, gene expression of differentiation markers, and so on. As a result, a remarkable improvement of function was recognized compared with the liver buds prepared by conventional methods. Further, when liver buds equivalent to $6 \times 10^6$ iPS cell-derived hepatic endoderm cells were transplanted into immunodeficient animal (NOD/scid mouse), the same result was obtained from the human albumin level secreted into the serum. According to the present disclosure, it becomes possible to achieve a remarkable improvement of function and also to reduce cost and labor required for quality evaluation and production. It is highly probable that similar effects will be obtained by replacing iPS cells with other pluripotent stem cells (e.g., embryonic stem (ES) cells).

Additionally, for solving the above-described problems, the present inventors believe that it is essential to induce cell differentiation and morphogenesis simultaneously by precisely recapitulating processes of organogenesis. Briefly, it is extremely important to develop a novel method for reconstituting a three-dimensional tissue structure in which different cell lineages are arranged well spatiotemporally. In the present disclosure, the inventors have developed a technique for reconstituting three-dimensional tissues and organs by an approach of recapitulating the interactions among a plurality of cells generated in organogenesis.

During physiological organogenesis processes, organogenesis accompanied by autonomous constitution of tissue structures and cell differentiation progresses through close interactions of organ cells with vascular endothelial cells and undifferentiated mesenchymal cells.

The present disclosure intends to artificially generate organ buds (that become a starting material for tissues and organs in vitro) by artificially recapitulating those early processes of organogenesis to thereby direct early differentiation via interactions among a plurality of cell lineages and induce the histogenetic capacity of those organ cells which achieved early differentiation. Further, the present disclosure intends to generate tissues and organs which are composed of terminally differentiated functional cells and vascular networks by transplanting those organ buds induced in culture systems into living bodies so as to initiate blood flow.

Specifically, organ cells at an optimal differentiation stage as obtained from pluripotent stem cells such as iPS cells are cocultured with vascular endothelial cells and mesenchymal cells. These three different cell components may preferably be cultured at an optimal mixture ratio. When these cells are cultured for a short time in a differentiation-inducing medium containing specific nutritional factors and humoral factors under special circumstances where cells are supported by extracellular matrix components, it becomes possible to induce three-dimensional organ buds with microvasculature in vitro. Further, by transplanting those organ buds induced in culture systems into a living body and initiating blood flow by promoting vascularization, it becomes possible to generate tissues and organs which have a highly ordered tissue structure comparable to that of adult tissues. Either one or both of vascular endothelial cells and mesenchymal cells may be replaced by a substance such as a factor secreted from vascular endothelial cells, a factor secreted from mesenchymal cells, or a factor secreted as a result of the presence of both vascular endothelial cells and mesenchymal cells.

A summary of the present disclosure is as described below.

(1) An organ bud prepared from vascular cells, mesenchymal cells and tissue or organ cells, wherein each of the vascular cell, the mesenchymal cell and the tissue or organ cell has been induced from pluripotent stem cells.

(2) The organ bud of (1) above, which is a structure capable of differentiating into an organ through maturing.

(3) The organ bud of (1) or (2) above, wherein the pluripotent stem cell is derived from human.

(4) The organ bud of any one of (1) to (3) above, wherein the pluripotent stem cell is at least one cell selected from the group consisting of induced pluripotent stem cell and embryonic stem cell.

(5) The organ bud of any one of (1) to (4) above, wherein the organ cell is hepatocyte and the organ bud is liver bud.

(6) The organ bud of (5) above, wherein the hepatocyte is TBX3 positive and ADRA1B positive.

(7) The organ bud of any one of (1) to (6) above, wherein the mesenchymal cell is CD166 positive and CD31 negative.

(8) The organ bud of any one of (1) to (7) above, wherein the mesenchymal cell is LHX2 positive and WT1 positive.

(9) The organ bud of (8) above, wherein the transcriptions of FOXF1, HLX1, COL4A and ALCAM of the mesenchymal cell are activated and the mesenchymal cell is LHX2 positive, WT1 positive and MIIA positive.

(10) The organ bud of any one of (1) to (9) above, wherein the vascular cell is CD31 positive and CD144 positive.

(11) The organ bud of (10) above, wherein expression of at least one gene selected from the group consisting of PECAM1, CDH5, KDR and CD34 of the vascular cell is increased relative to the corresponding expression in the pluripotent stem cell before directed differentiation.

(12) The organ bud of any one of (1) to (11) above, wherein TBX3 and ADRA1B co-positive cells obtained through the following steps are used as tissue or organ cells:

a) culturing pluripotent stem cells in the presence of a ROCK inhibitor and then in the presence of a factor belonging to the transforming growth factor β family, a factor belonging to the Wnt family and a class I histone deacetylase (HDAC) inhibitor, and further culturing the cells in the presence of a factor belonging to the transforming growth factor β family and a factor belonging to the Wnt family, and b) culturing the resultant cells from the above step in the presence of an FGF and a factor belonging to the TGF-β superfamily for directed differentiation into TBX3 and ADRA1B co-positive cells.

(13) The organ bud of any one of (1) to (11) above, wherein TBX3 and ADRA1B co-positive cells obtained through the following steps are used as tissue or organ cells:

a) culturing pluripotent stem cells in the presence of a ROCK inhibitor and then in the presence of a β catenin activator, a PI3K inhibitor and a factor belonging to the transforming growth factor β family, and further culturing the cells in the presence of a factor belonging to the transforming growth factor β family and a BMP inhibitor, and b) culturing the resultant cells from the above step in the presence of an FGF and a factor belonging to the TGF-β superfamily for directed differentiation into TBX3 and ADRA1B co-positive cells.

(14) The organ bud of any one of (1) to (11) above, wherein TBX3 and ADRA1B co-positive cells obtained through the following steps are used as tissue or organ cells:

a) culturing pluripotent stem cells in the presence of a ROCK inhibitor and then in the presence of a factor belonging to the transforming growth factor β family, and b) culturing the resultant cells from the above step in the presence of an FGF and a factor belonging to the TGF-β superfamily for directed differentiation into TBX3 and ADRA1B co-positive cells.

(15) The organ bud of any one of (1) to (12) above, wherein TBX3 and ADRA1B co-positive cells obtained through the following steps are used as tissue or organ cells:

a) culturing pluripotent stem cells in the presence of a ROCK inhibitor and then in the presence of a factor belonging to the transforming growth factor β family and a β catenin activator, and further culturing the cells in the presence of a factor belonging to the transforming growth factor β family, and b) culturing the resultant cells from the above step in the presence of an FGF and a factor belonging to the TGF-β superfamily for directed differentiation into TBX3 and ADRA1B co-positive cells.

(16) The organ bud of any one of (1) to (15) above, wherein LHX2 and WT1 co-positive cells obtained through the following steps are used as mesenchymal cells:

a) culturing pluripotent stem cells in the presence of a β catenin activator and a factor belonging to the TGF-β superfamily, b) then culturing the cells in the presence of a PDGF receptor agonist and a factor belonging to the transforming growth factor β family, and c) further culturing the cells in the presence of an FGF.

(17) The organ bud of any one of (1) to (15) above, wherein CD166 positive but CD31 negative cells obtained through the following steps are used as mesenchymal cell:

a) culturing pluripotent stem cells in the presence of a β catenin activator and a factor belonging to the TGF-β superfamily,

b) then culturing the cells in the presence of a PDGF receptor agonist and a factor belonging to the transforming growth factor β family, c) further culturing the cells in the presence of an FGF, and d) subsequently conducting maintenance culture of the cells in a medium for mesenchymal cells.

(18) The organ bud of any one of (1) to (17) above, wherein CD31 and CD144 co-positive cells obtained through the following steps are used as vascular cells:

a) culturing pluripotent stem cells in the presence of a ROCK inhibitor, b) then culturing the cells in the presence of a β catenin activator and a factor belonging to the TGF-β superfamily, and c) further culturing the cells in the presence of a vascular endothelial growth factor receptor (VEGFR) agonist and an adenylate cyclase activator.

(19) The organ bud of any one of (1) to (17) above, wherein CD31 and CD144 co-positive cells obtained through the following steps are used as vascular cells:

a) culturing pluripotent stem cells in the presence of a ROCK inhibitor, b) then culturing the cells in the presence of a VEGFR agonist, a factor belonging to the transforming growth factor β family, a β catenin activator and a factor belonging to the TGF-β superfamily, and c) further culturing the cells in the presence of a VEGFR agonist and an inhibitor of TGF-β type I receptor.

(20) The organ bud of any one of (1) to (17) above, wherein CD31 and CD144 co-positive cells obtained through the following steps are used as vascular cells:

a) culturing pluripotent stem cells in the presence of a ROCK inhibitor, b) then culturing the cells in the presence of a factor belonging to the transforming growth factor β family, c) further culturing the cells in the presence of an FGF and a factor belonging to the TGF-β superfamily, and d) subsequently culturing the cells in the presence of a VEGFR agonist.

(21) The organ bud of any one of (1) to (17) above, wherein CD31 and CD144 co-positive cells obtained through the following steps are used as vascular cells:

a) culturing pluripotent stem cells in the presence of a ROCK inhibitor, b) then culturing the cells in the presence of a factor belonging to the TGF-β superfamily, and c) further culturing the cells in the presence of a factor belonging to the TGF-β superfamily, a VEGFR agonist and an FGF.

(22) A method of preparing an organ bud, comprising culturing vascular cells, mesenchymal cells and tissue or organ cells in vitro, wherein each of the vascular cell, the mesenchymal cell and the tissue or organ cell has been induced from pluripotent stem cells.

(23) The method of (22) above, wherein the cells are cultured without using scaffold materials.

(24) A method of preparing a tissue or an organ, comprising transplanting the organ bud of any one of (1) to (21) above into a non-human animal and differentiating the organ bud into a tissue or an organ.

(25) A method of transplanting an organ bud, comprising transplanting the organ bud of any one of (1) to (21) above into a human or a non-human animal.

(26) A method of regeneration or function recovery of a tissue or an organ, comprising transplanting the organ bud of any one of (1) to (21) above into a human or a non-human animal and differentiating the organ bud into a tissue or an organ.

(27) A method of preparing a non-human chimeric animal, comprising transplanting the organ bud of any one of (1) to (21) above into a non-human animal and differentiating the organ bud into a tissue or an organ.

(28) A method of evaluating a drug, comprising using at least one member selected from the group consisting of the organ bud of any one of (1) to (21) above, the tissue or organ prepared by the method of (24) above and the non-human chimeric animal prepared by the method of (27) above.

(29) A method of preparing TBX3 and ADRA1B co-positive cells, comprising:

a) culturing pluripotent stem cells in the presence of a ROCK inhibitor and then in the presence of a factor belonging to the transforming growth factor β family, a factor belonging to the Wnt family and a class I histone deacetylase (HDAC) inhibitor, and further culturing the cells in the presence of a factor belonging to the transforming growth factor β family and a factor belonging to the Wnt family, and b) culturing the resultant cells from the above step in the presence of an FGF and a factor belonging to the TGF-β superfamily for directed differentiation into TBX3 and ADRA1B co-positive cells.

(30) A method of preparing TBX3 and ADRA1B co-positive cells, comprising:

a) culturing pluripotent stem cells in the presence of a ROCK inhibitor and then in the presence of a β catenin activator, a PI3K inhibitor and a factor belonging to the transforming growth factor β family, and further culturing the cells in the presence of a factor belonging to the transforming growth factor β family and a BMP inhibitor, and b) culturing the resultant cells from the above step in the presence of an FGF and a factor belonging to the TGF-β superfamily for directed differentiation into TBX3 and ADRA1B co-positive cells.

(31) A method of preparing TBX3 and ADRA1B co-positive cells, comprising:

a) culturing pluripotent stem cells in the presence of a ROCK inhibitor and then in the presence of a factor belonging to the transforming growth factor β family, and b) culturing the resultant cells from the above step in the presence of an FGF and a factor belonging to the TGF-β superfamily for directed differentiation into TBX3 and ADRA1B co-positive cells.

(32) A method of preparing TBX3 and ADRA1B co-positive cells, comprising:

a) culturing pluripotent stem cells in the presence of a ROCK inhibitor and then in the presence of a factor belonging to the transforming growth factor β family and a β catenin activator, and further culturing the cells in the presence of a factor belonging to the transforming growth factor β family, and b) culturing the resultant cells from the above step in the presence of an FGF and a factor belonging to the TGF-β superfamily for directed differentiation into TBX3 and ADRA1B co-positive cells.

(33) A method of preparing LHX2 and WT1 co-positive cells, comprising:

a) culturing pluripotent stem cells in the presence of a β catenin activator and a factor belonging to the TGF-β superfamily, b) then culturing the cells in the presence of a PDGF receptor agonist and a factor belonging to the transforming growth factor β family, and c) further culturing the cells in the presence of an FGF.

(34) A method of preparing CD166 positive but CD31 negative cells, comprising:

a) culturing pluripotent stem cells in the presence of a β catenin activator and a factor belonging to the TGF-β superfamily, b) then culturing the cells in the presence of a PDGF receptor agonist and a factor belonging to the transforming growth factor β family, c) further culturing the cells in the presence of an FGF, and d) subsequently conducting maintenance culture of the cells in a medium for mesenchymal cells.

(35) A method of preparing CD31 and CD144 co-positive cells, comprising:

a) culturing pluripotent stem cells in the presence of a ROCK inhibitor, b) then culturing the cells in the presence of a β catenin activator and a factor belonging to the TGF-β superfamily, and c) further culturing the cells in the presence of a vascular endothelial growth factor receptor (VEGFR) agonist and an adenylate cyclase activator.

(36) A method of preparing CD31 and CD144 co-positive cells, comprising:

a) culturing pluripotent stem cells in the presence of a ROCK inhibitor, b) then culturing the cells in the presence of a VEGFR agonist, a factor belonging to the transforming growth factor β family, a β catenin activator and a factor belonging to the TGF-β superfamily, and c) further culturing the cells in the presence of a VEGFR agonist and an inhibitor of TGF-type I receptor.

(37) A method of preparing CD31 and CD144 co-positive cells, comprising:

a) culturing pluripotent stem cells in the presence of a ROCK inhibitor, b) then culturing the cells in the presence of a factor belonging to the transforming growth factor β family, c) further culturing the cells in the presence of an FGF and a factor belonging to the TGF-β superfamily, and d) subsequently culturing the cells in the presence of a VEGFR agonist.

(38) A method of preparing CD31 and CD144 co-positive cells, comprising:

a) culturing pluripotent stem cells in the presence of a ROCK inhibitor, b) then culturing the cells in the presence of a factor belonging to the TGF-β superfamily, and c) further culturing the cells in the presence of a factor belonging to the TGF-β superfamily, a VEGFR agonist and an FGF.

(39) A method of preparing an organ bud, comprising culturing an organ cell together with at least one cell and/or factor selected from the group consisting of vascular endothelial cells, mesenchymal cells, factors secreted from vascular endothelial cells, factors secreted from mesenchymal cells, and factors secreted as a result of the presence of both vascular endothelial cells and mesenchymal cells.

(40) The method of (39) above, wherein the organ cell is a differentiated cell.

(41) The method of (39) above, wherein the organ cell is an undifferentiated cell.

(42) The method of any one of (39) to (41) above, wherein the organ cell is a cell of an endodermal organ or a cell capable of differentiating thereinto, a cell of a mesodermal organ or a cell capable of differentiating thereinto, or a cell of an ectodermal organ or a cell capable of differentiating thereinto.

(43) The method of (42) above, wherein the organ cell is a cell of an endodermal organ or a cell capable of differentiating thereinto.

(44) The method of (43) above, wherein the endodermal organ is liver or pancreas.

(45) The method of any one of (39) to (44) above, wherein the organ cell is an induced pluripotent stem cell-derived cell.

(46) The method of (45) above, wherein the induced pluripotent stem cell is derived from human.

(47) The method of any one of (39) to (46) above, wherein the organ cell is cultured in a medium for culturing vascular endothelial cells, together with at least one cell and/or factor selected from the group consisting of vascular endothelial cells, mesenchymal cells, factors secreted from vascular endothelial cells, factors secreted from mesenchymal cells, and factors secreted as a result of the presence of both vascular endothelial cells and mesenchymal cells.

(48) The method of any one of (39) to (47) above, wherein the organ cell is plated on a gel and cultured together with at least one cell and/or factor selected from the group consisting of vascular endothelial cells, mesenchymal cells, factors secreted from vascular endothelial cells, factors secreted from mesenchymal cells, and factors secreted as a result of the presence of both vascular endothelial cells and mesenchymal cells.

(49) The method of any one of (39) to (48) above, wherein the vascular endothelial cell is a differentiated cell.

(50) The method of any one of (39) to (48) above, wherein the vascular endothelial cell is an undifferentiated cell.

(51) The method of any one of (39) to (50) above, wherein the mesenchymal cell is a differentiated cell.

(52) The method of any one of (39) to (50) above, wherein the mesenchymal cell is an undifferentiated cell.

(53) A method of preparing a tissue or an organ, comprising transplanting the organ bud prepared by the method of any one of (39) to (52) above into a non-human animal and differentiating the organ bud into a tissue or an organ.

(54) A method of transplanting an organ bud, comprising transplanting the organ bud prepared by the method of any one of (39) to (52) above into a human or a non-human animal.

(55) The method of (54) above, wherein the site of transplantation of the organ bud is selected from the group consisting of the intracranial space, the mesentery, the liver, the spleen, the kidney, the kidney subcapsular space, and the supraportal space.

(56) A method of regeneration or function recovery of a tissue or an organ, comprising transplanting the organ bud prepared by the method of any one of (39) to (52) above into a human or a non-human animal and differentiating the organ bud into a tissue or an organ.

(57) A method of preparing a non-human chimeric animal, comprising transplanting the organ bud prepared by the method of any one of (39) to (52) above into a non-human animal and differentiating the organ bud into a tissue or an organ.

(58) A method of evaluating a drug, comprising using at least one member selected from the group consisting of the organ bud prepared by the method of any one of (39) to (52) above, the tissue or organ prepared by the method of (53) above, and the non-human chimeric animal prepared by the method of (57) above.

Effect of the Invention

The method of the present disclosure is advantageous over the conventional method using the two types of cells, one derived from umbilical cord and the other from bone marrow, in the following points: (1) the resultant organ primordia are stable in quality because of being non-donor dependent, (2) organ primordia generated from three types of cells that are entirely derived from iPS cells are dramatically superior to conventional ones in functionality and (3) it becomes easy to secure immunocompatibility.

Further, conventionally, functional cells obtained from pluripotent stem cells by directed differentiation remained at an immature differentiation stage, compared to those functional cells that constitute biological tissues. This is because terminal differentiation of functional cells has not been achieved by the conventional directed differentiation method. According to the present disclosure, establishment of a method of inducing terminal differentiation of human functional cells based on reconstitution of three-dimensional structures is expected (for example, reconstitution of cell polarity against vasculature). This method is highly valuable as a technique for generating human functional cells.

Further, in conventional directed differentiation methods for pluripotent stem cells, it has been totally impossible to obtain tissue stem cells. When generation of tissue stem cells from iPS cells is achieved according to the present disclosure, the human liver stem cell manipulation technique developed by the present inventors in the past (WO/2009/139419) may potentially be combined with this accomplishment to provide a cell manipulation technique useful for mass generation of human liver cells.

Further, in the present disclosure, it is possible to reconstitute three-dimensional human tissue structures with vascular networks by artificially recapitulating the interactions among a plurality of cells generated in organogenesis. Therefore, the method of the present disclosure is expected to become a basic technique for generating human tissues and organs with blood flow through appropriately arranged vascular networks; generation of such tissues or organs has never been achieved by conventional techniques.

The present specification encompasses the contents disclosed in the specification and/or drawings of Japanese Patent Application No. 2017-230647 and Japanese Patent Application No. 2011-210157 based on which the present patent application claims priority.

(A) The schematic design (middle) of an omni-well-array plate for mass production. Fluorescent image analysis (right) confirms the large-scale (>20,000) production of micro liver buds (LBs) entirely from human iPSCs. (B) The appearance of 1 (omni)-well-array plate (left), and plate flatness (right) as shown by a 3D profilometer. (C) SEM image of iPSC-LBs generated from triple progenitor co-culture. (D) Confocal image of the generated iPSC-LB revealed endothelial sprouting (white arrowhead) inside. Green, iPSC-HE; red, HUVEC. (E) Gross morphologies of LBs generated from different endoderm stages (days 0-20). The x axis shows 3D culture duration (cumulative), and the y axis shows the source cell stage from 2D culture. The right two columns show low- and high-magnification images after collection at day 22. (F) Violin plot analysis of the size homogeneity in various endoderm-derived LBs. Data were collected by quantification of the morphology of over 600 LBs at cumulative day 22 relative to the first day of 3D culture.

Figure 2:
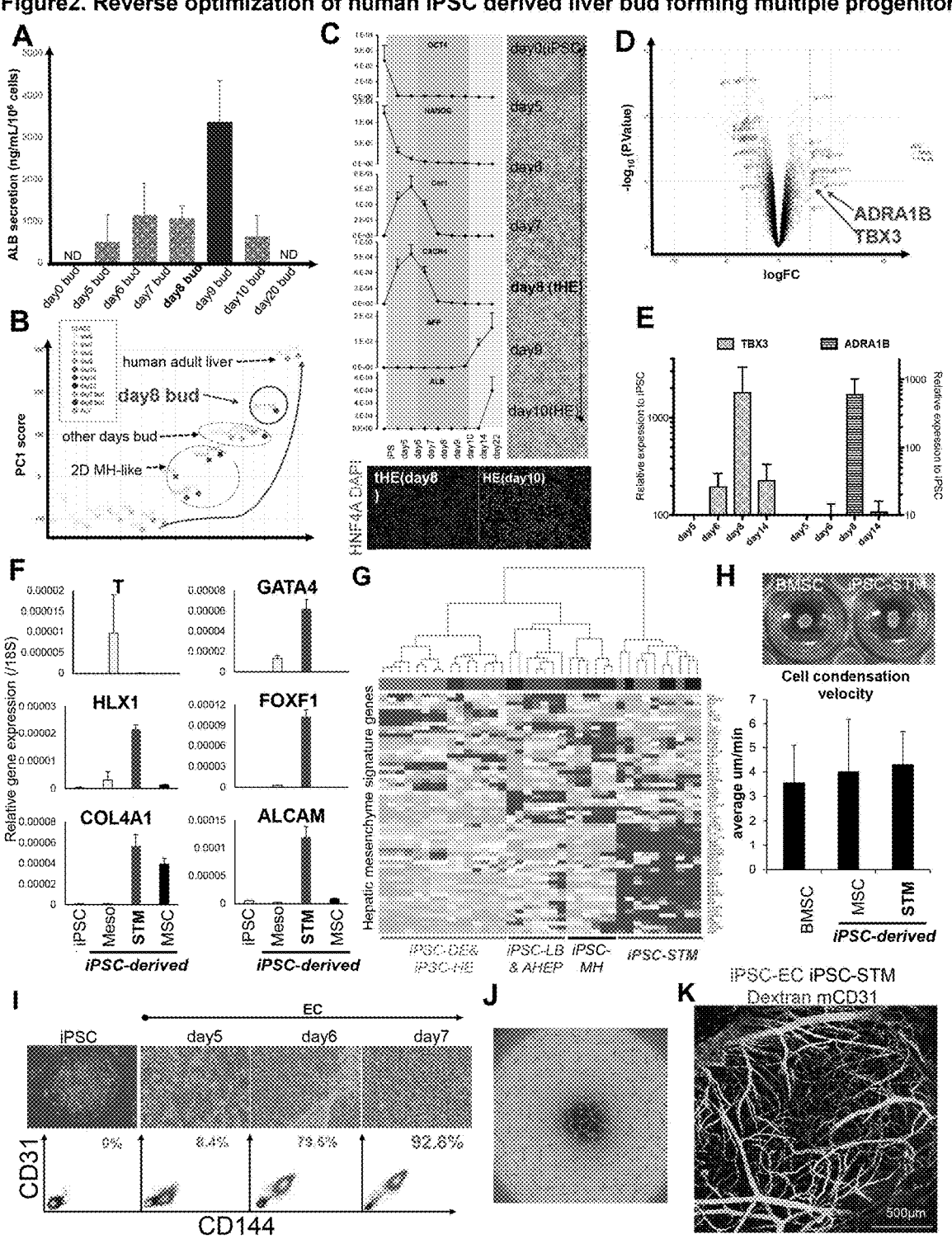

FIG. 2 Reverse optimization of human iPSC-derived liver bud-forming multiple progenitors.

(A) ELISA-based quantification of time-course-dependent AFP and ALB production per 24 hr/$2 \times 10^5$ cells at day 20. Data represent means±SD, n=4; *p<0.05. (B) Principal-component analysis of LBs generated from endodermal cells of multiple stages revealed a significant commitment toward the hepatic fate. The x axis reflects in vitro experiment-based maturity order. (C) Characterization of each differentiation-stage-specific reported marker by qRT-PCR analysis of pluripotency, definitive endoderm, and HE cell markers. The microscopic morphology of cells at various stages is presented in the right panel. The bottom panel shows immunostaining of HNF4A at the day 8 and day 10 stages. (D) Volcano plot gene expression data. Genes differentially expressed at a log2-fold change level between day 6 and day 8 stage>3 with a p value<0.05 are displayed as red circles. Cell surface proteins or nuclear proteins are indicated by red circles with each gene name in bold letter. (E) Day 8 transitional endodermal cells are marked by both TBX3 and ADRAIB and proteins by immunostaining (see FIG. 3A). Data represent the means±SD, n=3; *p<0.05. (F) qRT-PCR-based screen of the early mesoderm gene T (BRACHURY) and the STM genes HLX1, GATA4, FOXF1, COL4A1, and ALCAM. Meso, day 3 iPSC-derived lateral plate mesoderm; STM, day 10 cells after FGF2 and PDGFB co-exposure; MSC, day 20 cells maintained in MSC medium after passaging STM. Error bars represent the SD of values obtained from three independent experiments (n=4). (G) Hierarchical clustering with adult human hepatic (AdHep) mesenchymal cell signatures in iPSC-STM (Asahina et al., 2009, Asahina et al., 2011, El Taghdouini et al., 2015). (H) Time-lapse imaging analysis of the self-condensation from iPSC-STM by phase contrast microscopy. The velocity of collective cell movement is presented as an average of 3 independent experiments. Two-day-cultured tissues using BMSCs and iPSC-MSC are shown as controls. (I, J) Microscopic characterization of iPSC-EC and FACS-based quantification of CD31 and CD144 over time (I) and subsequent endothelial sprouting assay on Matrigel (J). (K) Generation of human vascular networks in vivo by co-transplantation of iPSC-STM and AAVS1::mCherry iPSC-ECs. Dextran, green; mouse-specific CD31, blue. Scale bar, 500 μm.

FIG. 3 Self-organization of human liver buds entirely from iPSC-derived multiple progenitors.

(A) Overview of the protocol used for all-iPSC LB generation from feeder-free human iPSCs. Process verification was routinely conducted by immunostaining of TBX3 (red) and ADRA1B (red) on tHE cells; WT1 (red), LHX2 (red), and myosin IIA (green) in STM; and CD144 (red) and CD31 (green) on ECs, respectively. (B) Self-organization into LBs with endothelial sprouting after 72 hr of culture was confirmed by bright field (top) and light-sheet (bottom)

4D time-lapse imaging, respectively. Green, iPSC-tHE; red, iPSC-EC; not labeled, iPSC-STM. Scale bar, 500 μm. (C) Confocal imaging of the entire all-iPSC buds confirmed the presence of an endothelial network. (D) Macroscopic lateral view of generated all-iPSC buds. The panel shows a top view. Scale bar, 1,000 μm. (E) Gross observation of trans-planted all-iPSC-LBs showing perfusion of human blood vessels at day 2. The dotted area indicates the transplanted all-iPSC-LBs. (F) Intravital imaging of transplanted all-iPSC-LBs demonstrating the formation of human blood vessels from iPSC-ECs. Red, AAVS1::mCherry iPSC-ECs. Scale bar, 500 μm. (G) Presence of iPSC-hepatic cells aligned with human-iPSC-derived vessels inside all-iPSC-LB transplants at day 28. Green, iPSC-tHEs; red, iPSC-ECs. (H) Dextran and fluorescent mouse CD31 antibody co-infusion study revealing the connections (white dotted line or arrow) among iPSC-ECs and host mouse vessels. Green, dextran; red, iPSC-ECs; blue, mouse CD31. (I) Close asso-ciation between iPSC-STM and iPSC-EC. Green, iPSC-STM; red, iPSC-EC.

FIG. 4 Functional validation of mass-produced miniatur-ized human liver buds.

(A) Strategic batch validation scheme on each $10^8$-cell-scale production cycle by assessing in vitro and in vivo function. The middle panel shows the uniformity of col-lected LB morphology. Green, iPSC-tHEs. (B) Albumin production in differentiated all iPSC-LBs. As controls, human adult hepatocytes in 2D (AdHep 2D), AdHep cocul-ture (AdHep LB), and control LB (generated from iPSC-tHEs, HUVECs, and BMSCs) are shown. Data represent means±SD, n=6. (C) Multiple-hepatocyte-derived protein production and (D) ammonia metabolism of in-vitro-cul-tured all-iPSC-LBs at day 21 of culture. Data represent means±SD, n=6 (C) and n=3 (D). (E) tSNE-based visual-ization of hepatic maturation status of LBs generated entirely from iPSC (all iPSC-LB) compared with previous approaches and human primary samples. (F) APRES profiles between human adult hepatocytes (F) and differentiated all iPSC-LB (G) shown by aster plot. (G) Kaplan-Meier sur-vival curves of transplanted and sham groups in a subacute liver failure model using alb-Tk-NOG mouse. n=114 for LB and n=39 for the sham-transplanted group. **p=0.0013. X axis indicates post-transplant day. (H) Time-dependent human serum albumin production in the all-iPSC-LB trans-plant (n=48) or human adult hepatocyte transplant (n=12). Data represent means±SEM. (I) Detection of human-specific diclofenac metabolite in iPSC-LB transplanted mice. 3'-Hy-droxy-4'-methoxydiclofenac (VI), which is a human-specific metabolite known to accumulate in the plasma, was quan-tified by liquid chromatography/tandem mass spectrometry (LC-MS/MS).

Figure 5:
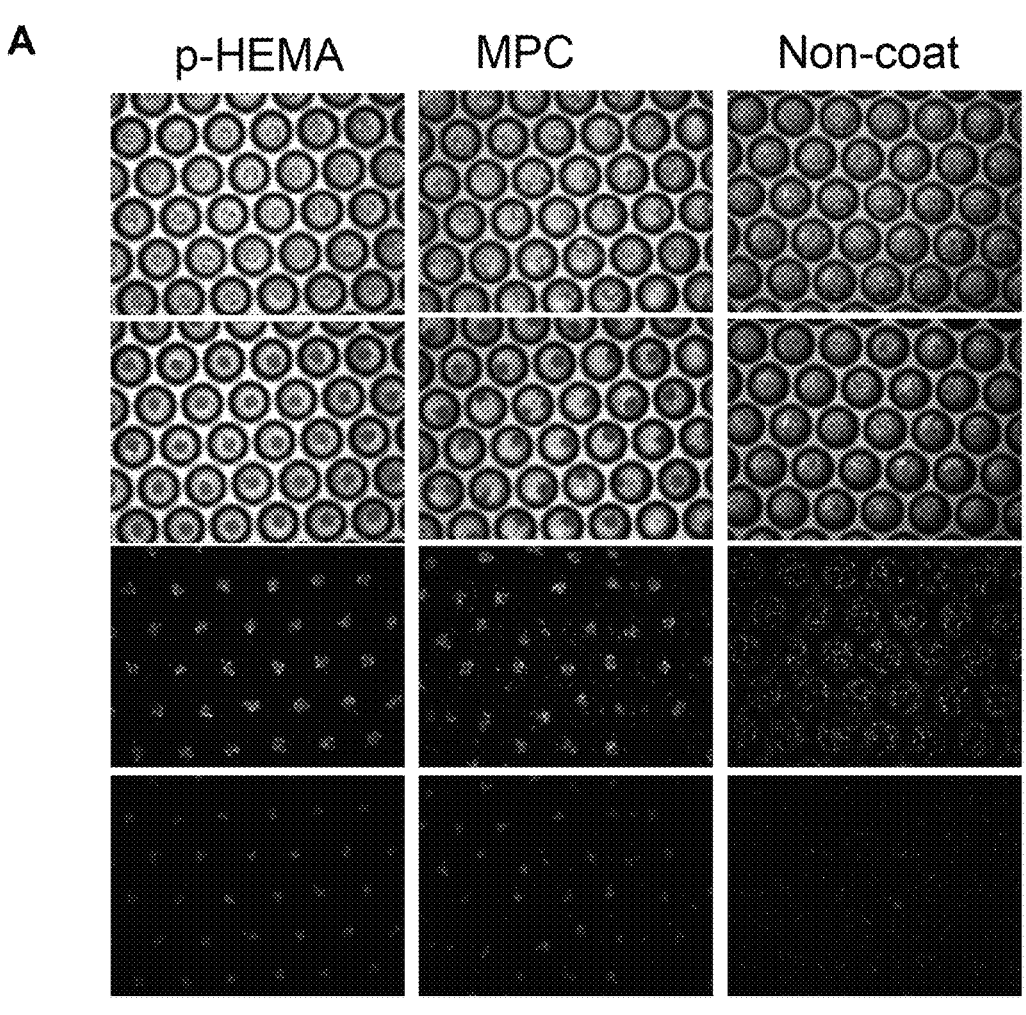
Figure 5:
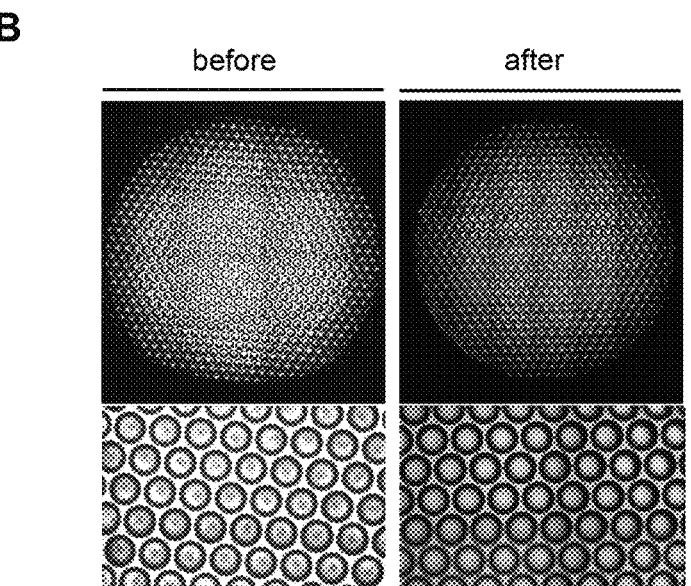

FIG. 5 (Figure S1) Coating optimization and collection of mass produced LBs. (A) Coating with pHEMA and MPC polymers prior to cell seeding. Green, HUVEC; Red, MSC. (B) Collection of LBs by pipetting. Microscopic views acquired before (left) and after (right) LB collection are shown. After collection, no remaining LBs were detected, suggesting successful collection of LBs from the plate.

Figure 6:
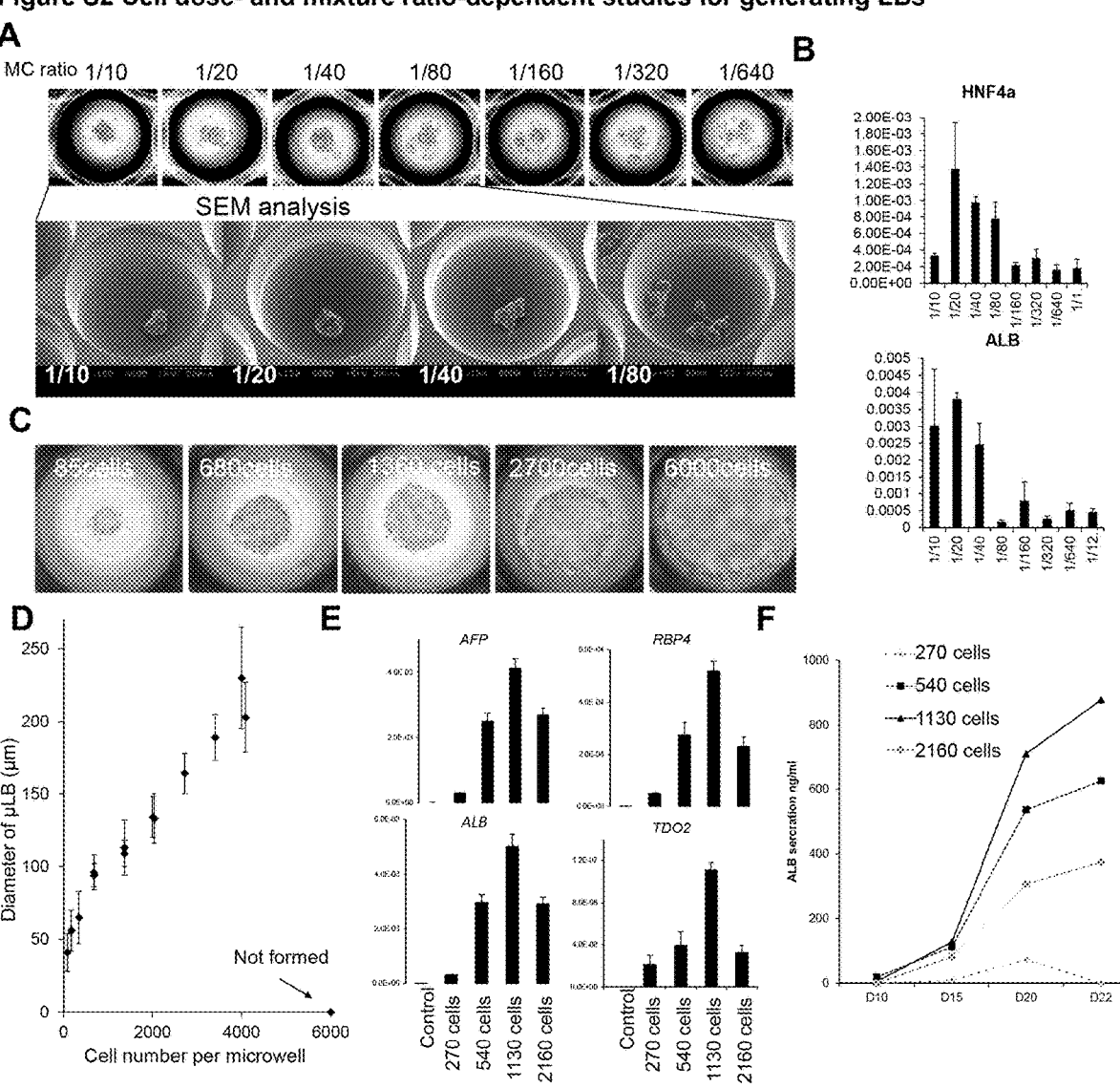

FIG. 6 (Figure S2) Studies of cell dose- and mixture ratio-dependency for generating LBs.

(A) Various proportions of mesenchymal cells (MCs) were examined for LB generation on the Elplasia platform. Microscopic and electron microscopic views are shown. A number of generated LBs were shown in the indicated MC proportions. (B) qRT-PCR analysis of HNF4A and ALB revealed that ¹⁄₂₀ of total cells is most efficient for liver bud generation. The data represent means±s.d., n=3. (C, D) Total cell-dependent increase in the diameter of LBs, up to 4000 cells per spot. Cells didn't form a tissue at 6000 cells per spot. Green, HUVEC; Red, MSC. The quantification of LB size is presented in D. (E) Gene expression and (F) protein production capacity of LBs at each indicated cell dose. The data represent means±s.d., n=3.

Figure 7:
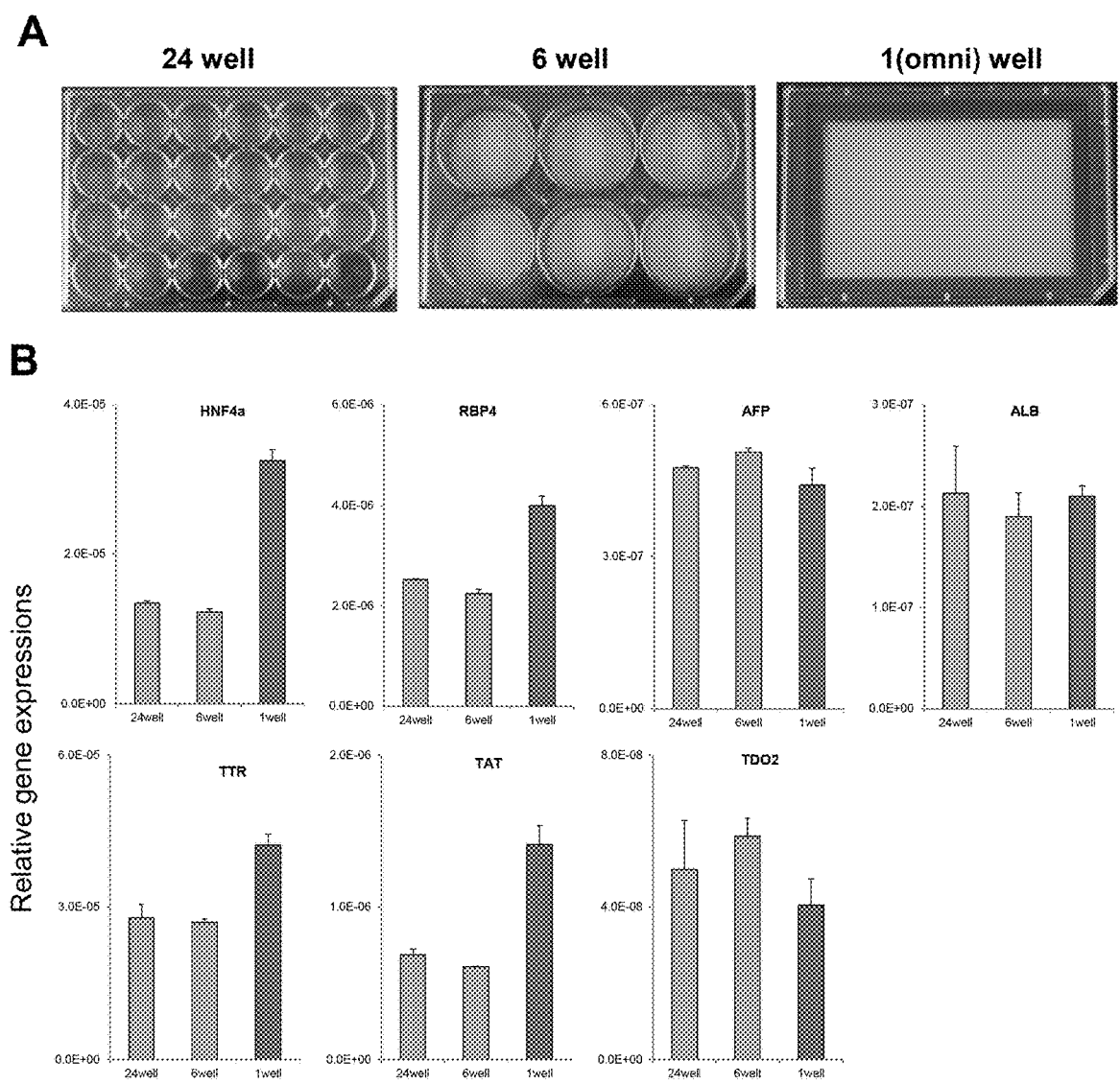

FIG. 7 (Figure S3) Establishment of the omni-well plate for large-scale production. (A) Elplasia 24 well, 6 well, and 1(omni) well plate. All the plates meet SBS footprint dimen-sions. By minimizing dead space, the number of microwells per plate increased as follows: 14,400 (600×24 well), 18,000 (3,000×6 well) and 20,000 (1 well). (B) qRT-PCR analysis of the hepatic marker genes HNF4A, RBP4, AFP, ALB, TTR, TAT, TDO2 and GLUT2 in LBs derived from 24 well, 6 well and omni (1) well plate. The data represent means±s.d., n=3.

Figure 8:
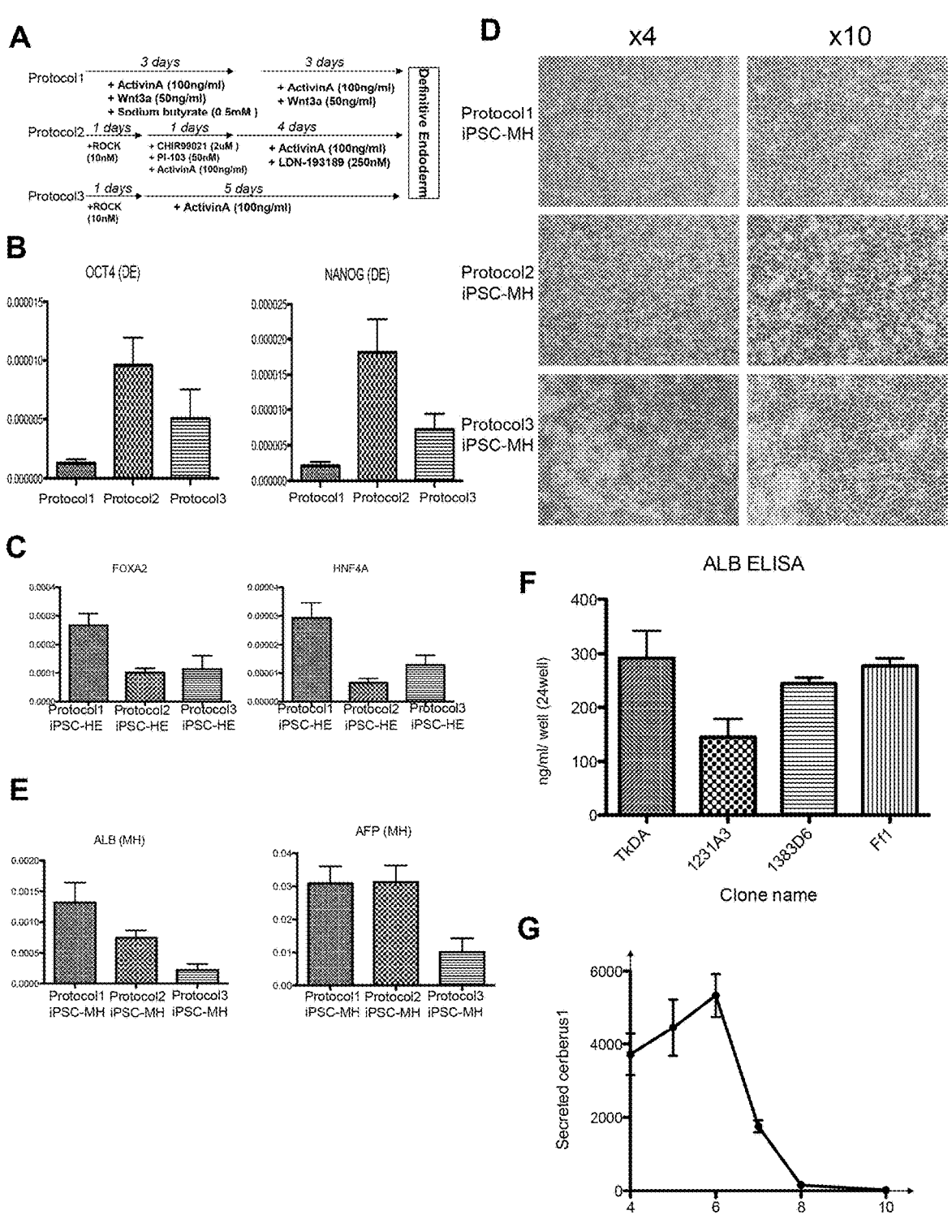

FIG. 8 (Figure S4) Optimization of the iPSC-derived endodermal cell induction protocol.

(A) Three representative protocols for generating defini-tive endoderm cells. (B, C) qRT-PCR analysis of pluripo-tency markers at the DE stage and hepatic endoderm mark-ers at the HE stage following each indicated protocol. The data represent means±s.d., n=12. (D) The microscopic mor-phology of mature hepatocyte-like cells from different pro-tocols. (E) qRT-PCR analysis of hepatocyte markers at the iPSC-MH stage. The data represent means±s.d., n=6. (F) Reproducible generation of iPSC-MH from multiple donor-derived iPSC clones. The data are shown as ng/ml/24 hour/2×10⁵ cells. n=10. (G) ELISA quantification of secreted cerberus 1 (DE marker) during the day 4 to day 10 transition.

Figure 9:
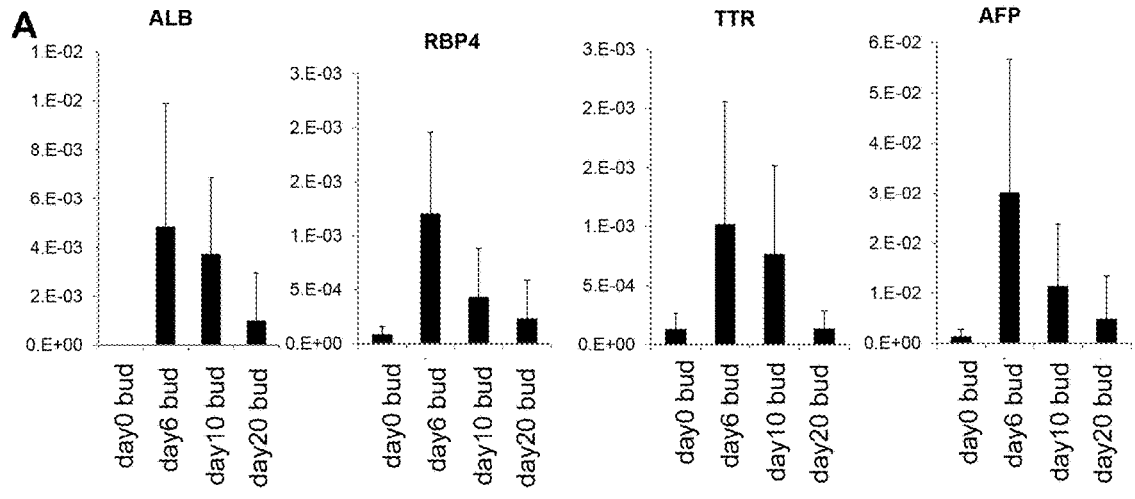
Figure 9:
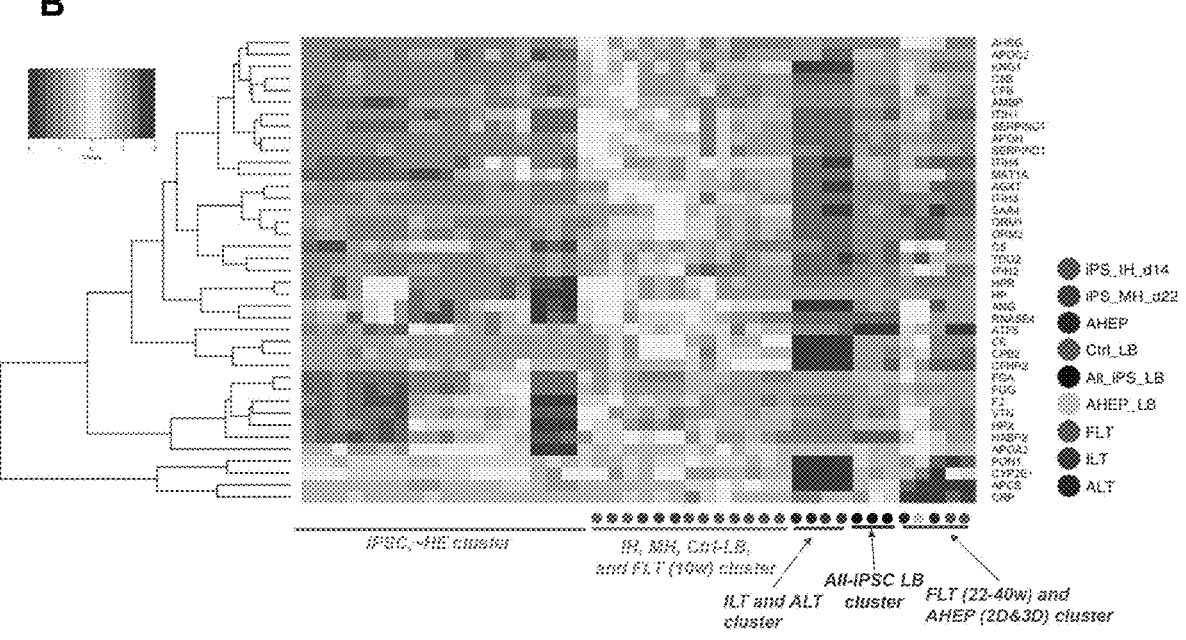
Figure 9:
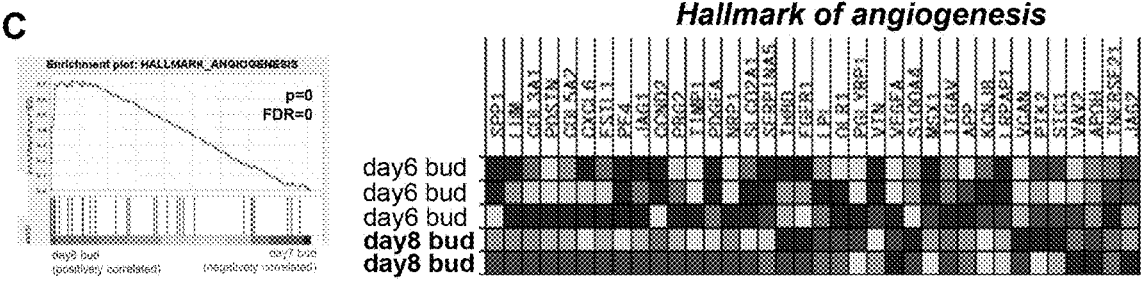

FIG. 9 (Figure S5) Optimization of iPSC-derived liver bud generation protocols.

(A) Liver buds from iPSCs (day 0), DE (day 6 or 7), HE (day 10) and MH (day 14) cells. Gene expression analyses revealed that only the day 6 and day 10 endodermal cells exhibited the highest hepatic functions after extended cul-ture. (B) Hierarchical clustering of 2-D cells: iPSC, DE, HE, IH and MH; and 3-D tissues: human iPSC-liver buds, human fetal and adult liver tissues using signatures developed by Si-Tayeb et al. (Si-Tayeb et al., 2010). FLT, 10 gwk or 22-40 gwk pool Fetal Liver Tissue; ILT, 0 yr Infant Liver Tissue; ALT, 5 yrs, 30 yrs, 44 yrs or 55 yrs old Liver Tissues; AHEP, human primary hepatocytes; AHEP-3D, 3D cultured human primary hepatocytes. (C) The GSEA analysis and heatmap visualization of angiogenesis hallmark genes between day 6 and day 8 buds.

Figure 10:
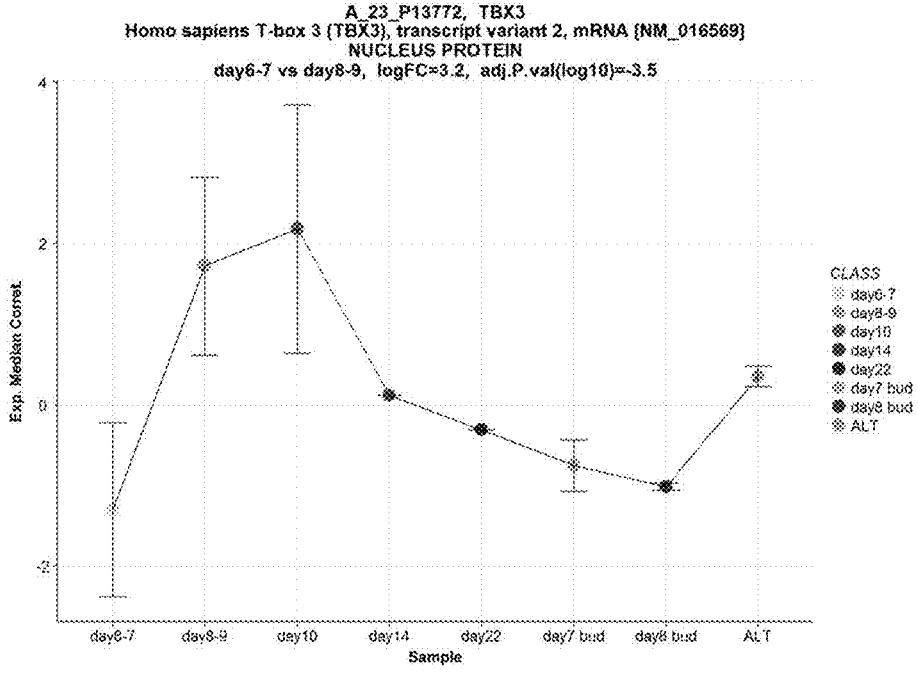
Figure 10:
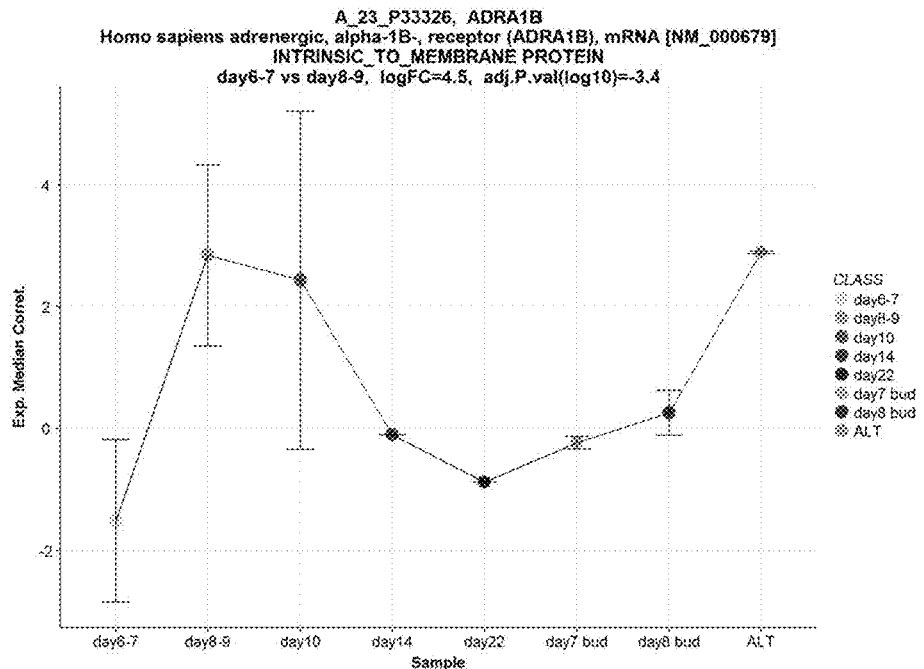

FIG. 10 (Figure S6) Identification of TBX3 and ADRA1B as markers of iPSC-tHEs. (A, B) Time-dependent expression of TBX3 in panel A and ADRAIB in panel B. The data represent means±s.d., n=3.

Figure 11:
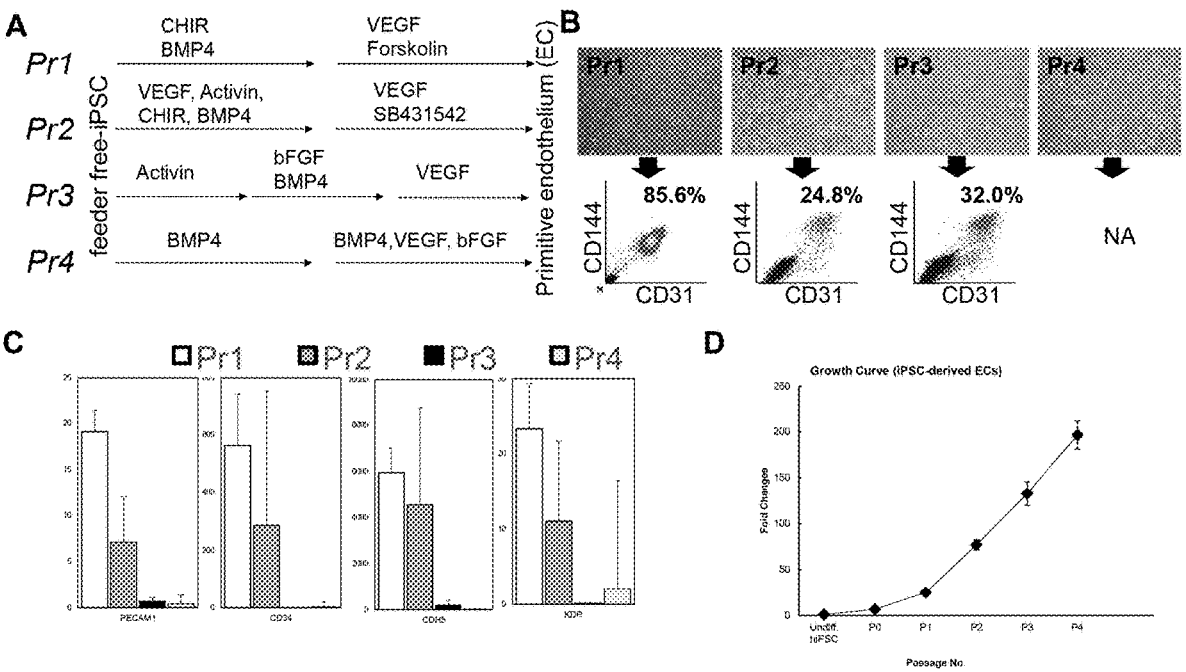

FIG. 11 (Figure S7) Highly efficient differentiation into primitive endothelial progenitors from feeder free human iPSCs.

(A) Four independent step-wise specification protocols for EC differentiation. (B) Microscopic characterization of iPSC-ECs which underwent respective differentiation, fol-lowed by FACS-based initial screen with CD31 and CD144. (C) qRT-PCR-based analysis of the EC markers. (D) Growth curve of iPSC-EC after four times of passaging.

Figure 12:
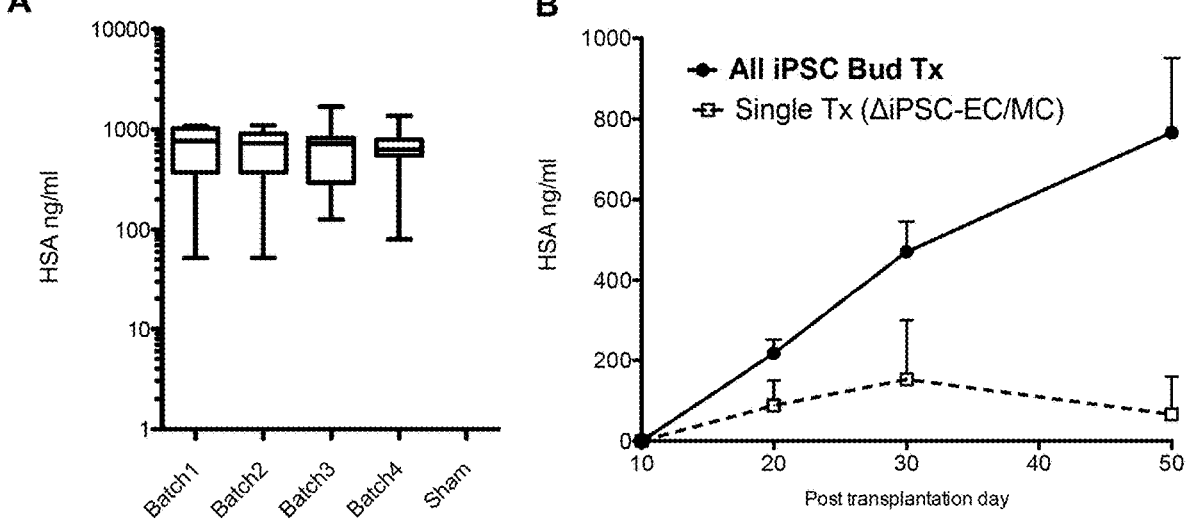

FIG. 12 (Figure S8) In vivo functionalization of human iPSC liver buds.

(A) Whisker plot comparison (5-95 percentile) of ALB levels in all iPSC-LB transplanted group at day 40. Each graph represents raw value collected from all 10 different mice. (B) Time-dependent human serum albumin production in the presence or absence of iPSC-ECs and STM. The data represent means±s.e.m., n=6. *: P=0.0356. Transplanted cell number was 3×10⁶ cell-equivalent LBs in panel A and panel B.

Figure 13:
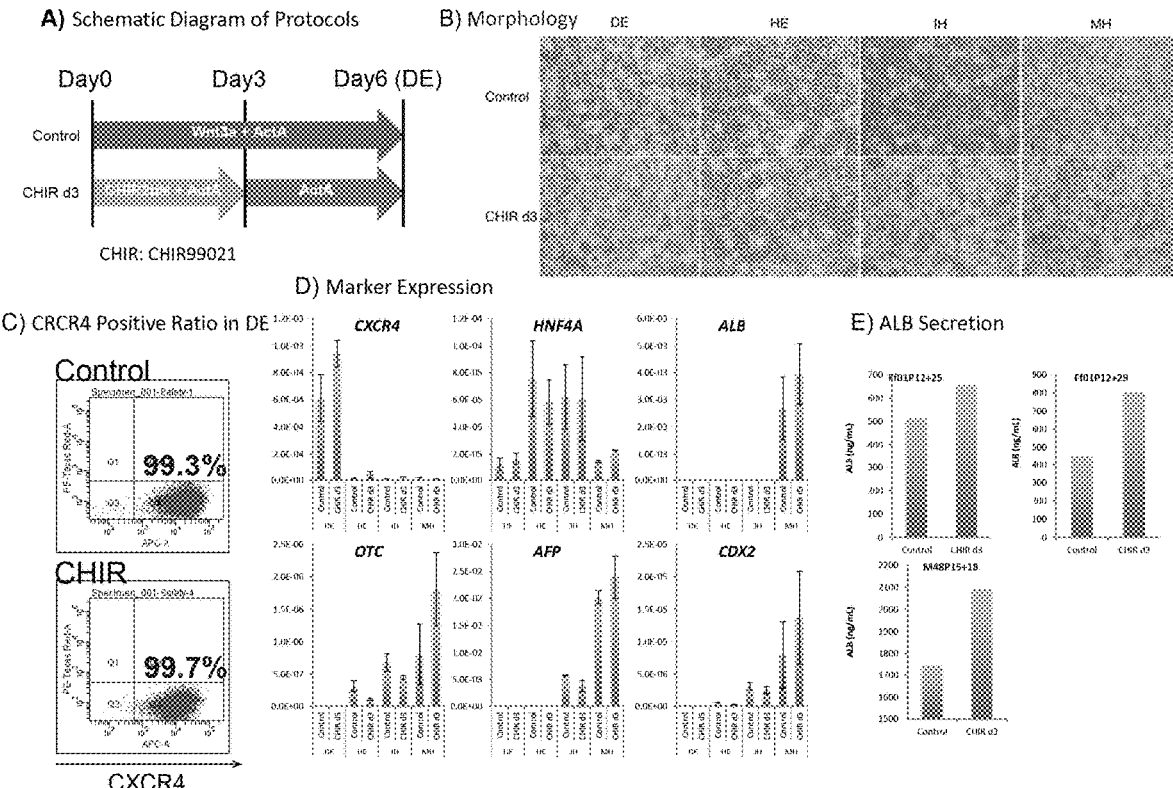

FIG. 13 In the directed differentiation from iPSC to DE, Wnt3a is replaceable with CHIR99021. FIG. 13A: Schematic diagram of a protocol using CHIR99021 as an alternative for Wnt3a. Upon studying various conditions, a condition was selected in which CHIR99021 (2 µM) is added for 3 out of the 6 days of DE directed differentiation. FIG. 13B: Cellular morphologies at respective differentiation stages of a conventional method using Wnt3a and under the condition where CHIR99021 (2 µM) is added for 3 days. No morphological changes are observed compared to the case of using Wnt3a. FIG. 13C: Analysis of positive ratios for CXCR4 (a DE marker) by flow cytometry at the DE stage of the conventional method using Wnt3a and under the condition where CHIR99021 (2 µM) is added for 3 days. The positive ratio for CXCR4 when CHIR99021 is added is comparable to the case of using Wnt3a. FIG. 13D: Expression analysis of various differentiation markers by quantitative PCR (qPCR). The results were comparable to the case of using Wnt3a. FIG. 13E: ELISA analysis of albumin secretion at the MH stage. In multiple iPSC clones with CHIR99021, albumin secretion was comparable to, or even higher than, that of the case using Wnt3a.

Figure 14:
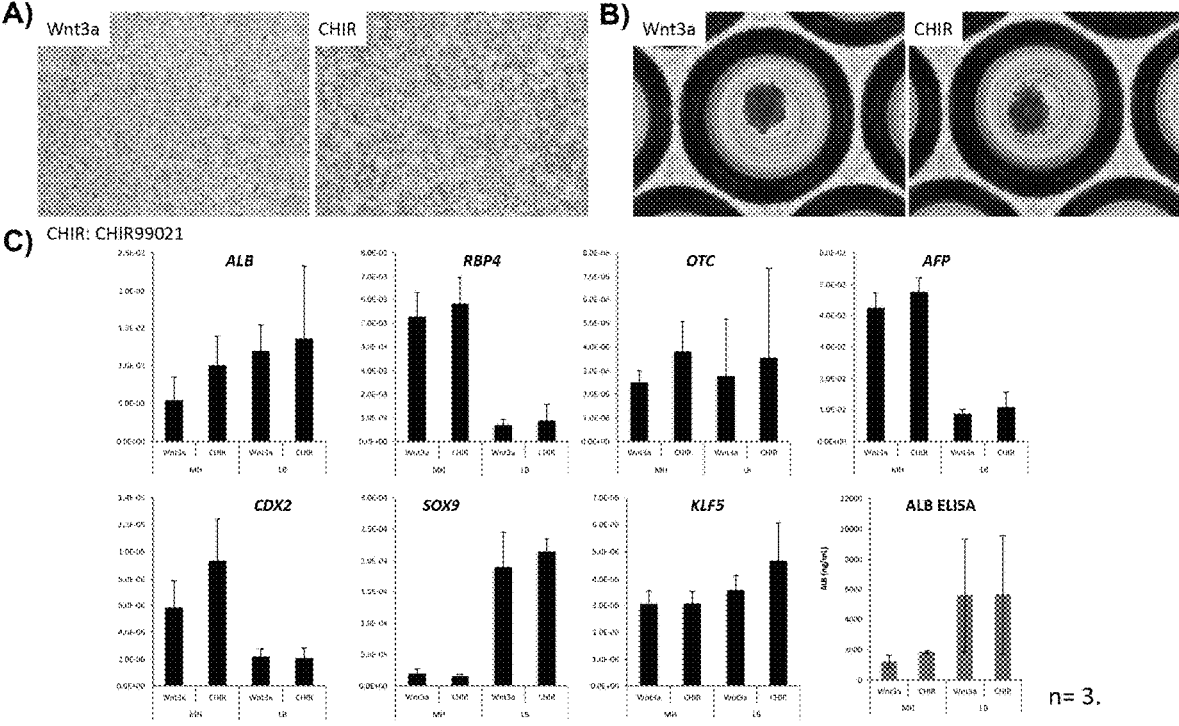

FIG. 14 Comparison of Wnt3a and CHIR99021 (in vitro MH, LB) FIGS. 14A and B: Cellular morphologies in MH (FIG. 14A) and LB (FIG. 14B). No morphological differences are observed compared to the case of using Wnt3a. FIG. 14C: Marker expression analyses in MH and LB by qPCR. Expressions with CHIR99021 are c to those of the case using Wnt3a; there is observed no increase in the expression of marker genes belonging to other cell lineages (such as intestinal markers).

Figure 15:
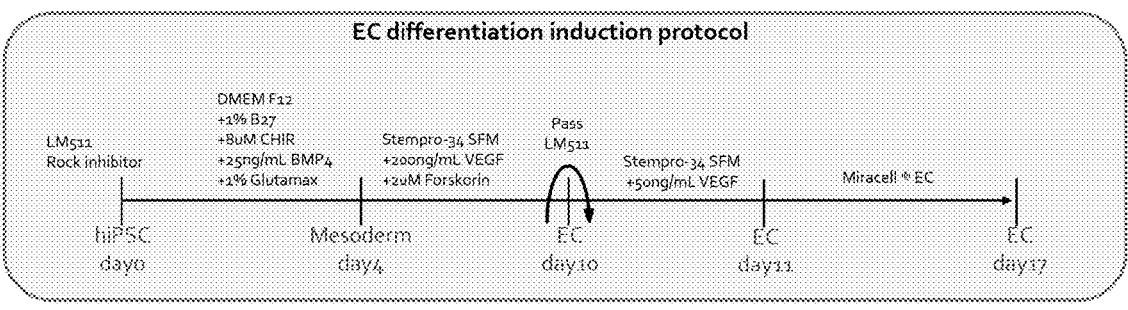

FIG. 15 EC induction. A revised protocol for directed differentiation to iPSC-derived vascular endothelial cell (iPSC-EC).

Figure 16:
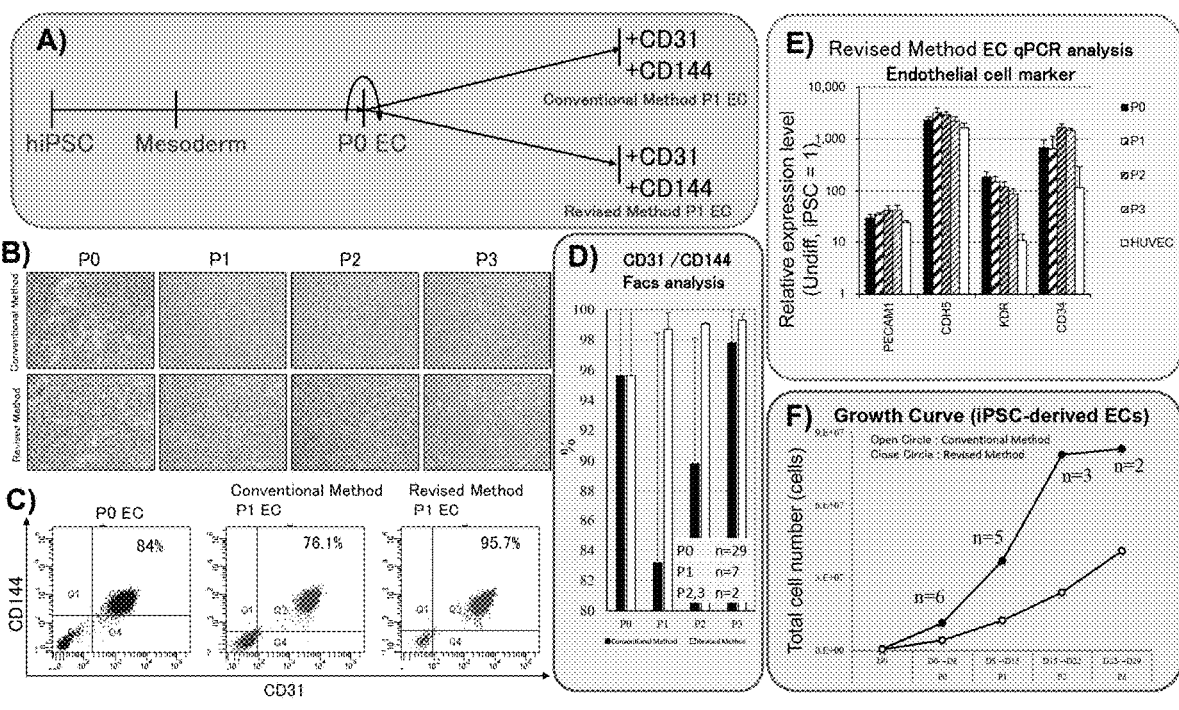

FIG. 16 Study of directed differentiation medium intended for clinical application. FIG. 16A: A schematic diagram of directed differentiation protocol. FIG. 16B: Cellular morphologies in the conventional method and the revised method. No morphological differences are observed. FIG. 16C: Analysis by flow cytometry of positive ratios for EC marker in the conventional method and the revised method. FIG. 16D: A summary of the flow cytometry analysis in FIG. 16C. High positive ratios for CD31/CD144 are obtained more stably in the revised method than in the conventional method. FIG. 16E: Expression analyses of individual differentiation markers by qPCR. Expressions of EC markers are stable in the revised method even after passages. FIG. 16F: Cell growth upon each passage. Growth capacity after passages is high in the revised method compared to the conventional method.

Figure 17:
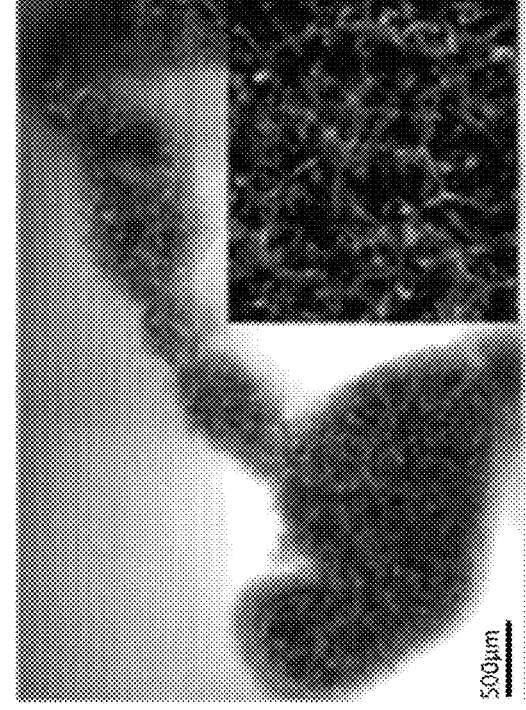
Figure 17:
Figure 17:
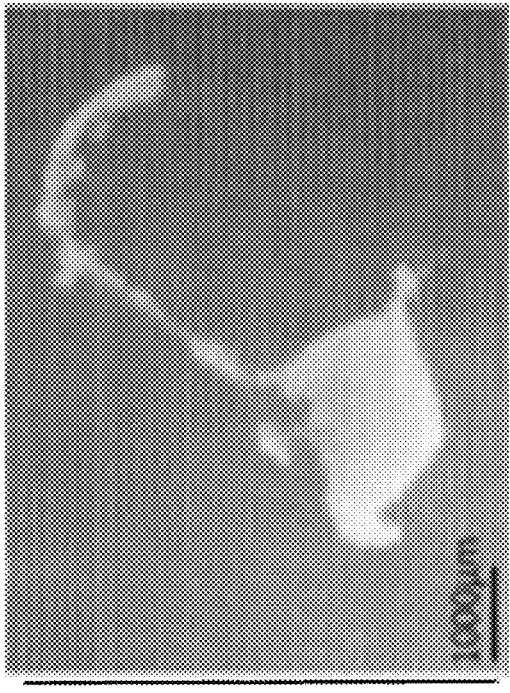
Figure 17:
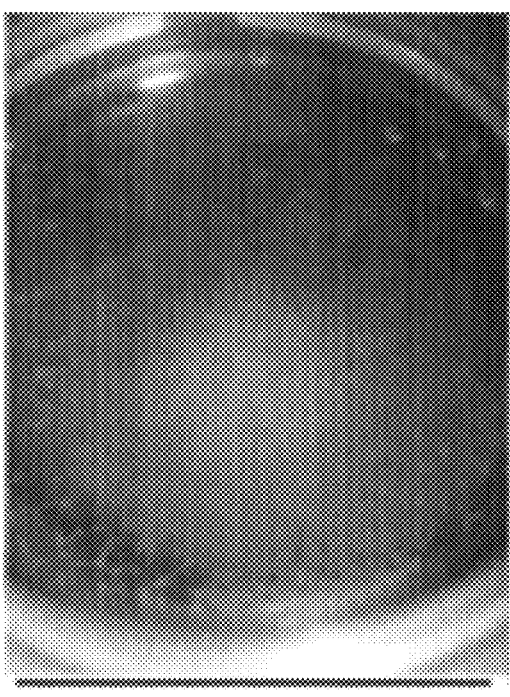

FIG. 17 This figure shows autonomous organization of human iPS cell-derived hepatic endoderm cells. Lower left panel shows human hepatic endoderm cells. Upper left panel shows a three-dimensional structure (liver bud) formed by coculture of three cell lineages of hepatic endoderm cells, vascular endothelial cells and undifferentiated mesenchymal cells (at day 4 of culturing). Upper right panel is a fluorescence microscopic photograph of the above-described three-dimensional structure. Vascular endothelial cells (HUVECs) are labeled with EGFP and undifferentiated mesenchymal cells (hMSCs) are labeled with KO but iPS cells are not labeled.

Figure 18:
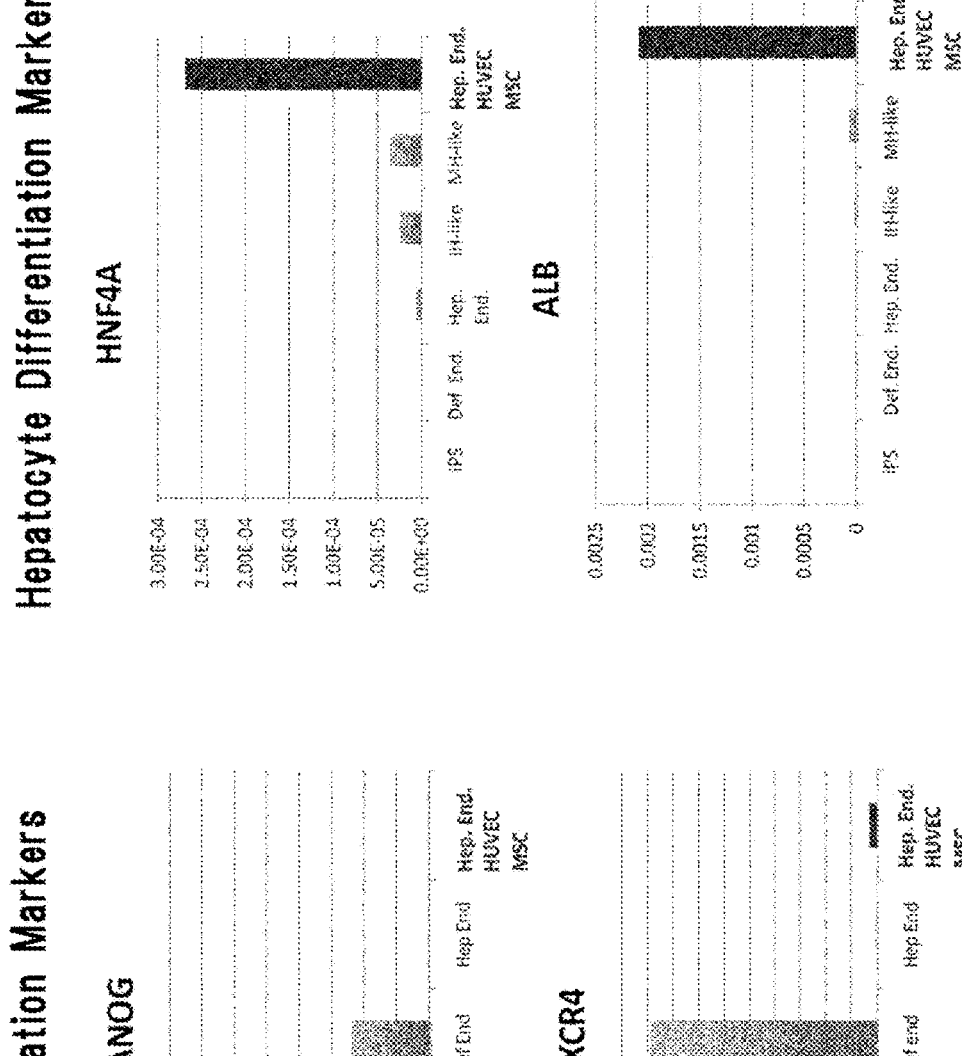

FIG. 18 This figure shows expression levels of marker proteins as for cells that constitute organ buds. "Hep. End.

HUVEC MSC" represents cells constituting organ buds; "undiff iPS" and "iPS" represent iPS cells; "Def End" represents activin-induced endoderm cells; "Hep End" represents BMP4- and FGF2-induced hepatic endoderm cells. "IH-like" represents immature hepatocyte-like cells described in K. Si-Taiyeb, et al. Hepatology, 51 (1): 297-305 (2010) and "MH-like" represents mature hepatocyte-like cells described in the same reference.

Figure 19:
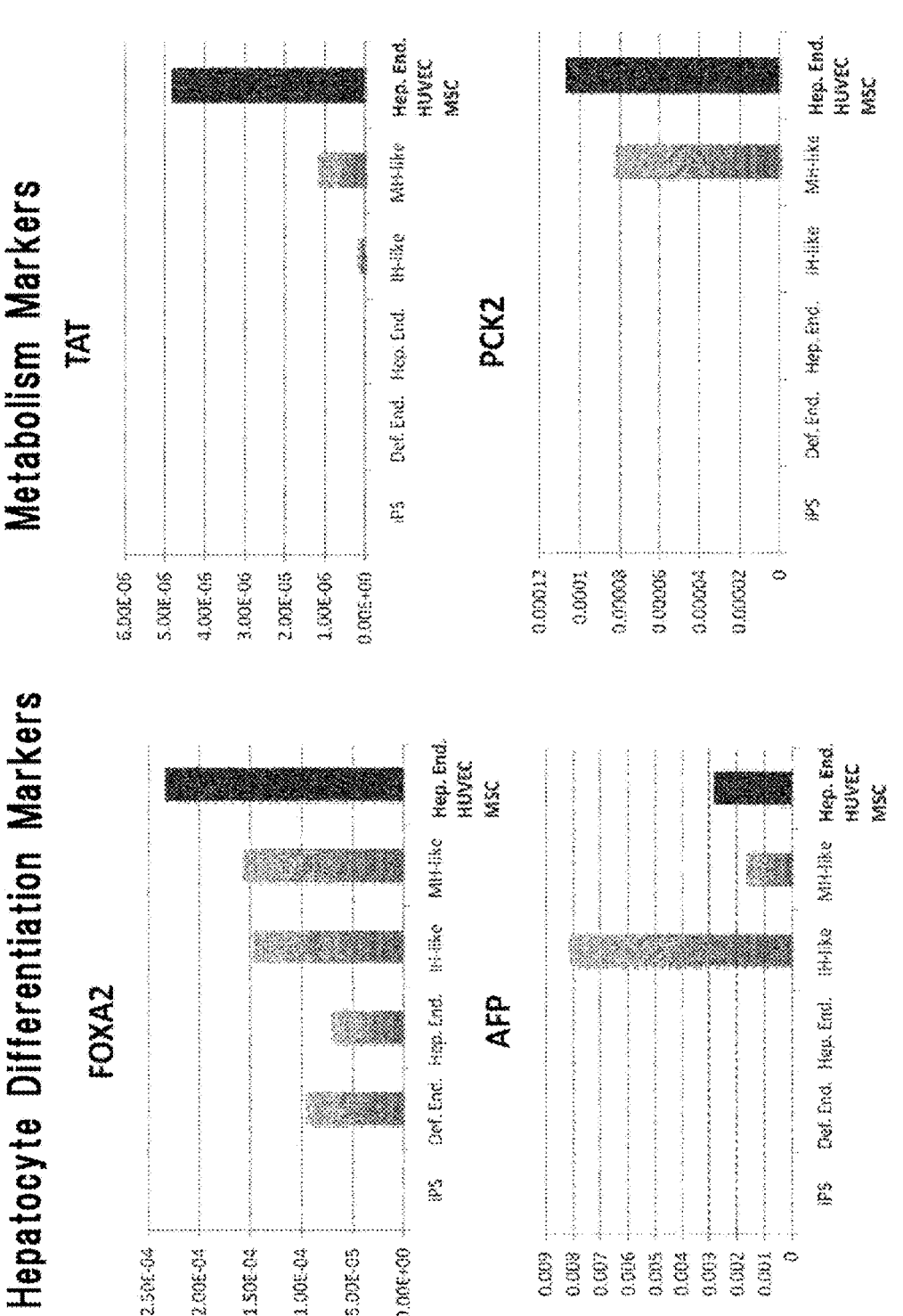

FIG. 19 This figure shows expression levels of marker proteins as for cells that constitute organ buds. "Hep. End. HUVEC MSC" represents cells constituting organ buds; "iPS" represents iPS cells; "Def End" represents activin-induced endoderm cells; "Hep End" represents BMP4- and FGF2-induced hepatic endoderm cells. "IH-like" represents immature hepatocyte-like cells described in K. Si-Taiyeb, et al. Hepatology, 51 (1): 297-305 (2010) and "MH-like" represents mature hepatocyte-like cells described in the same reference.

Figure 20:
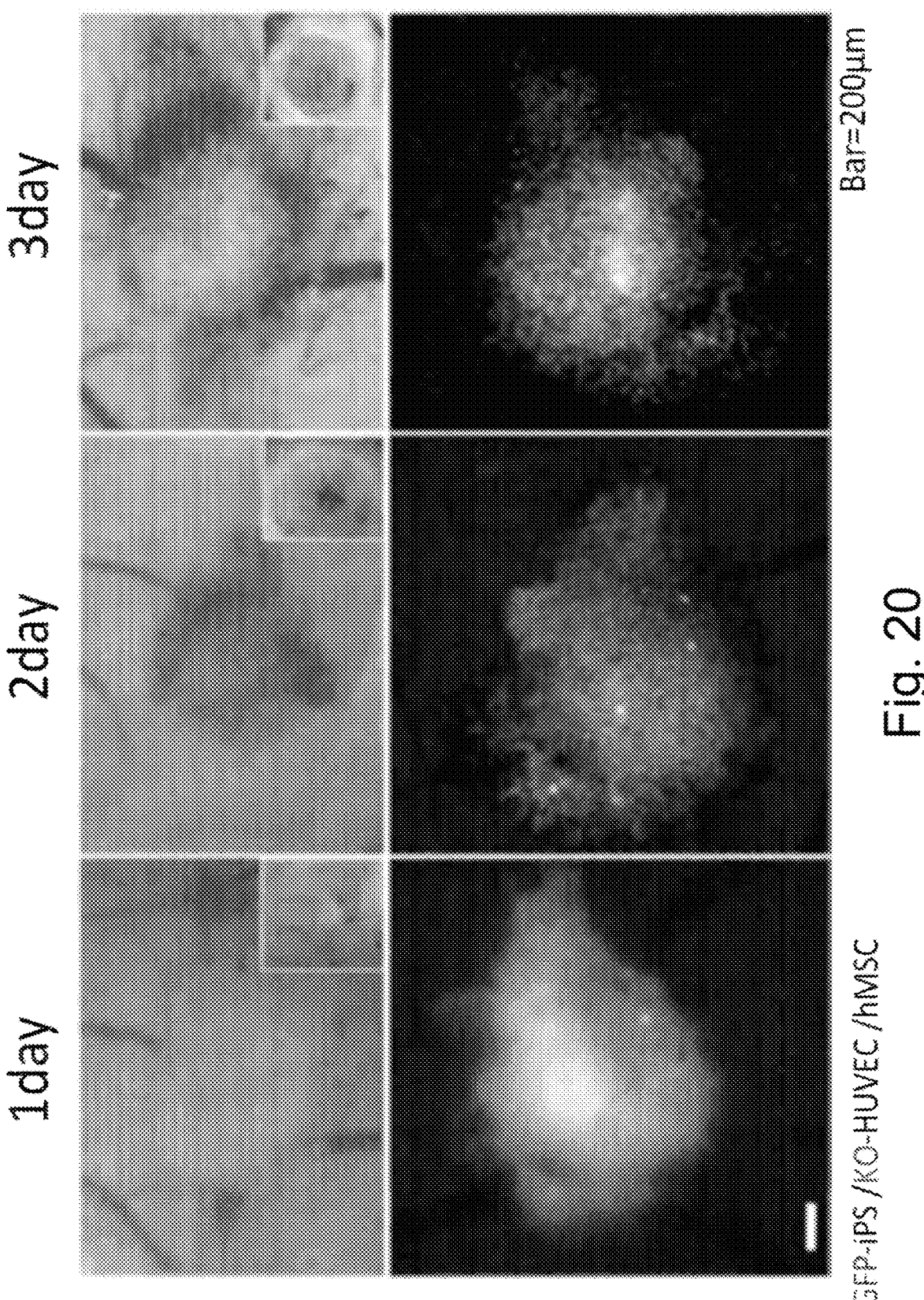

FIG. 20 This figure shows the state of a liver bud transplanted into an immunodeficient mouse. iPS cells are labeled with GFP and undifferentiated endothelial cells are labeled with KO.

Figure 21:
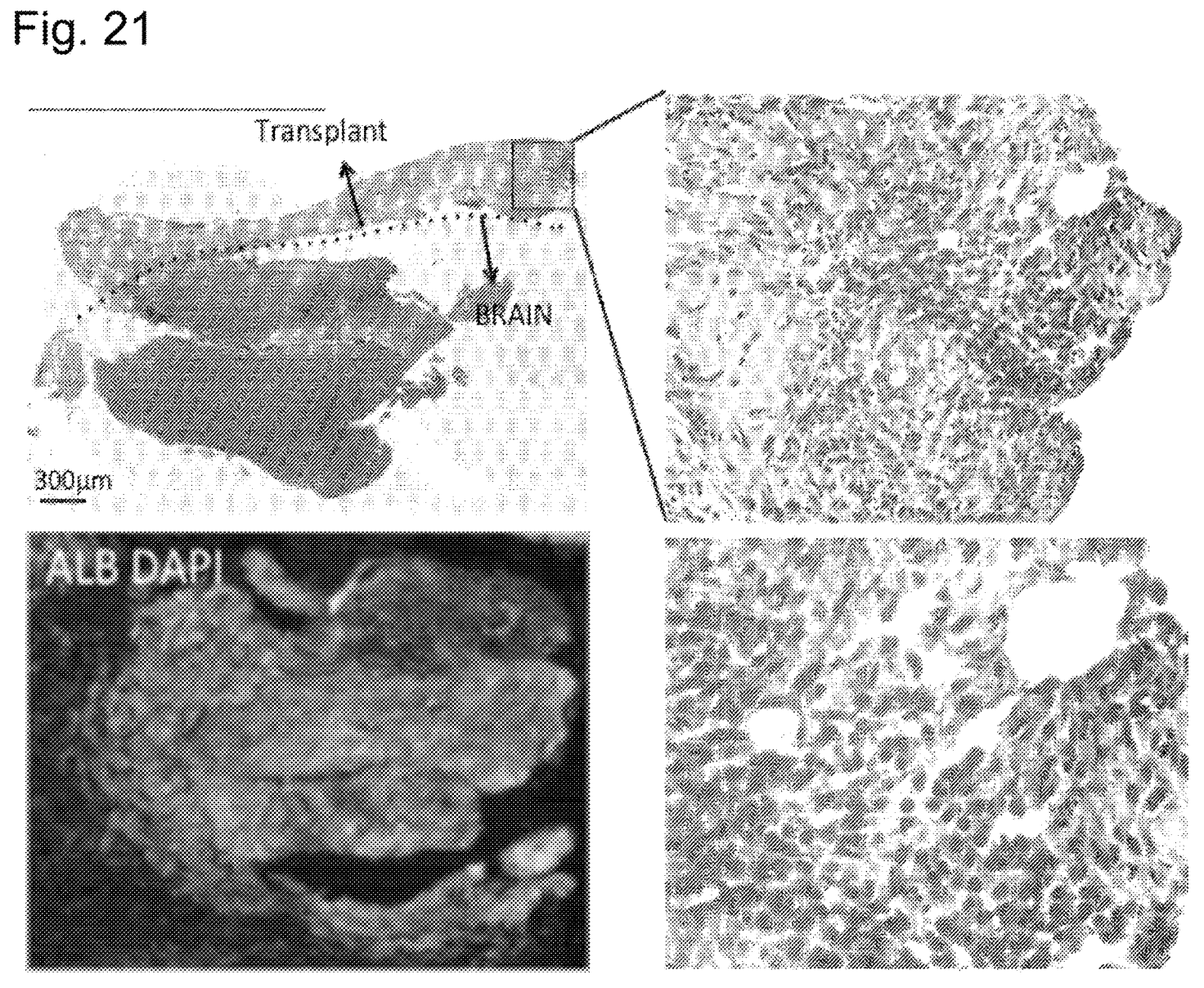

FIG. 21 This figure shows histological analysis of a liver bud 2 weeks after transplantation.

Figure 22:
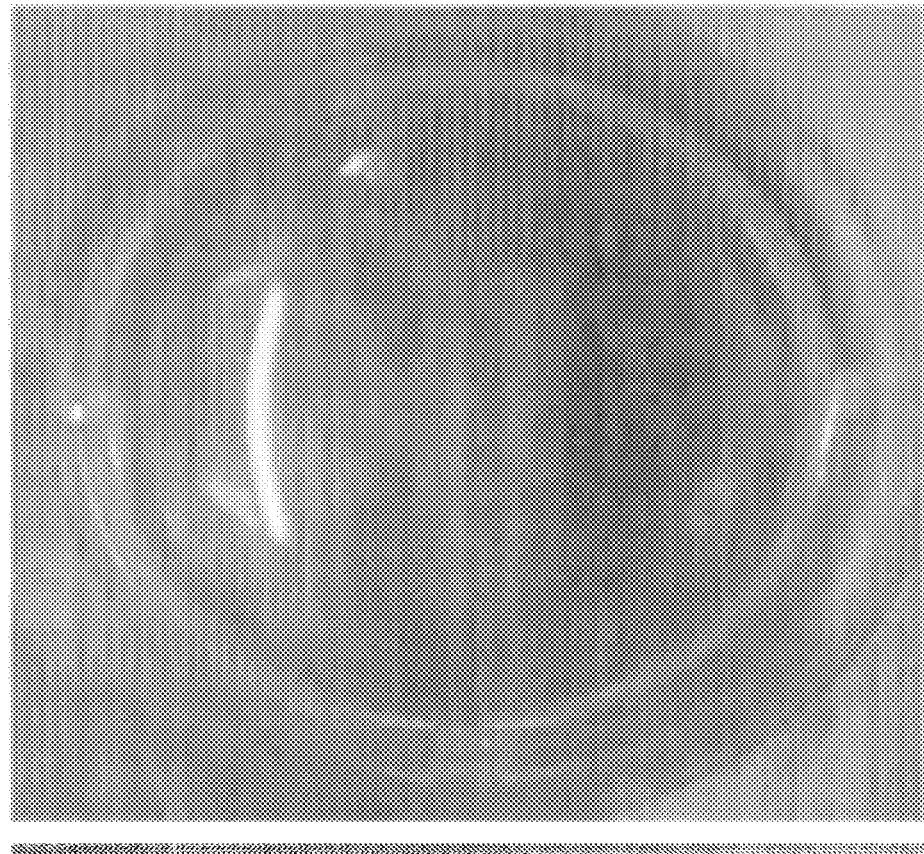
Figure 22:
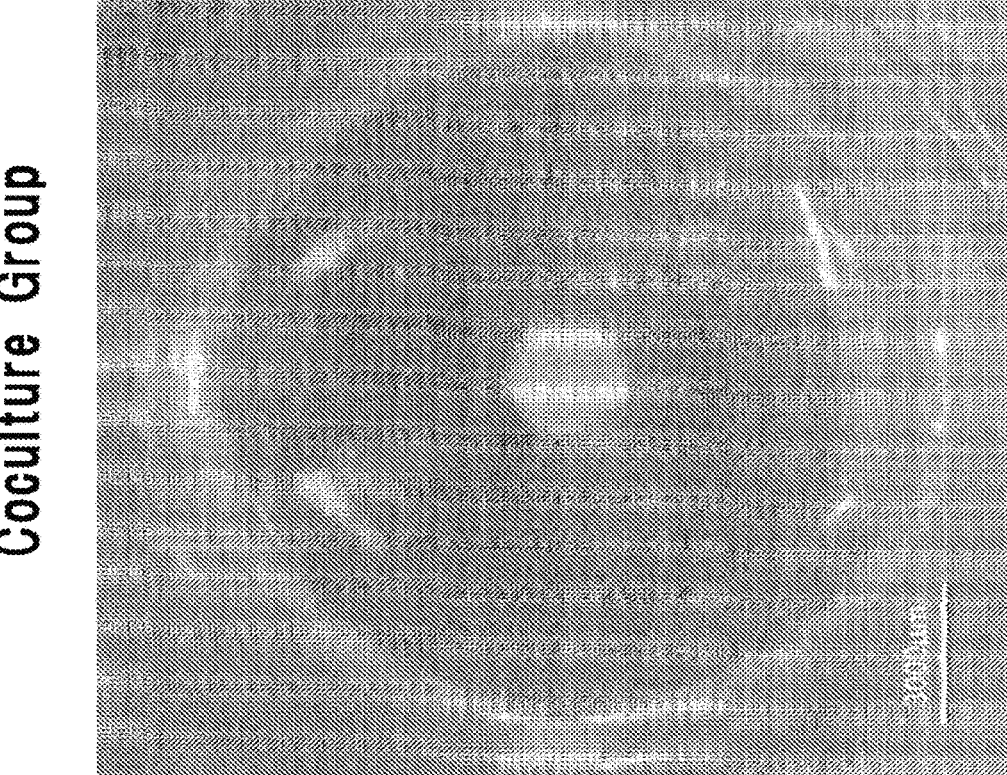

FIG. 22 This figure shows autonomous organization of pancreatic β cells. Left panel shows cocultured pancreatic β cells, and right panel shows independently cultured pancreatic β cells.

Figure 23:
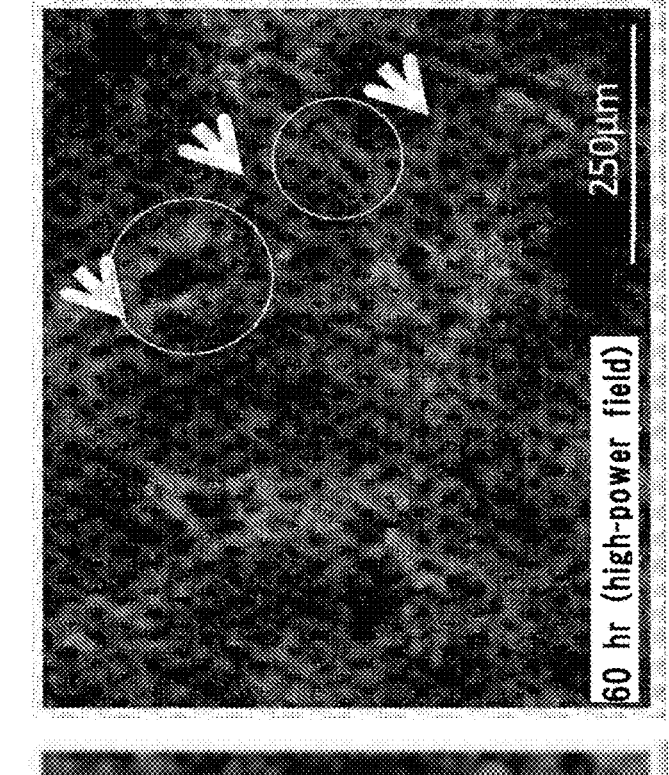
Figure 23:

FIG. 23 This figure shows masses and vessel-like luminal structures of pancreatic β cells.

Figure 24:
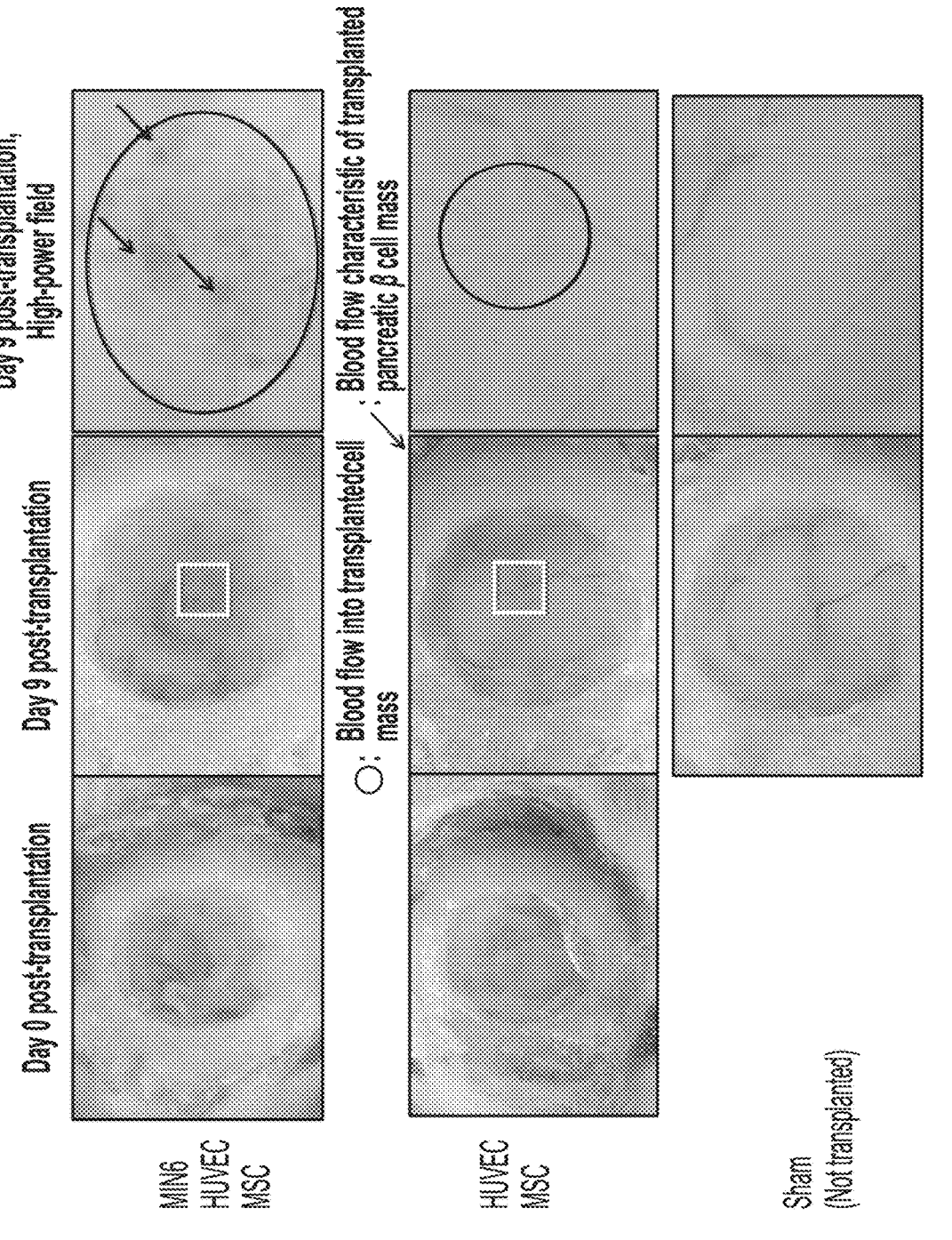

FIG. 24 This figure shows blood perfusion into transplanted cell masses.

Figure 25:
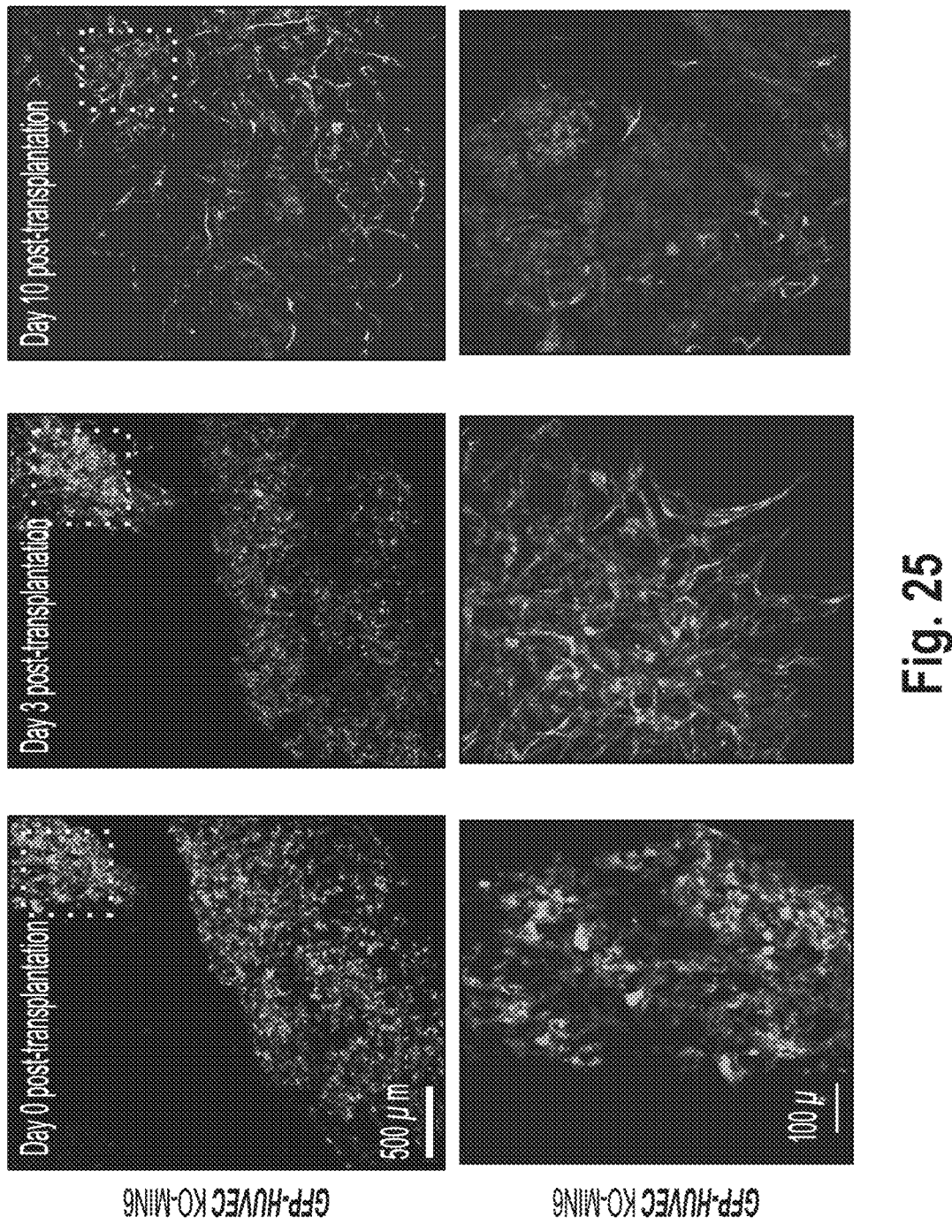

FIG. 25 This figure shows the process of spheroid formation from pancreatic β cells. Vascular endothelial cells (HUVECs) are labeled with GFP and pancreatic β cells (MIN6) are labeled with KO.

Figure 26:
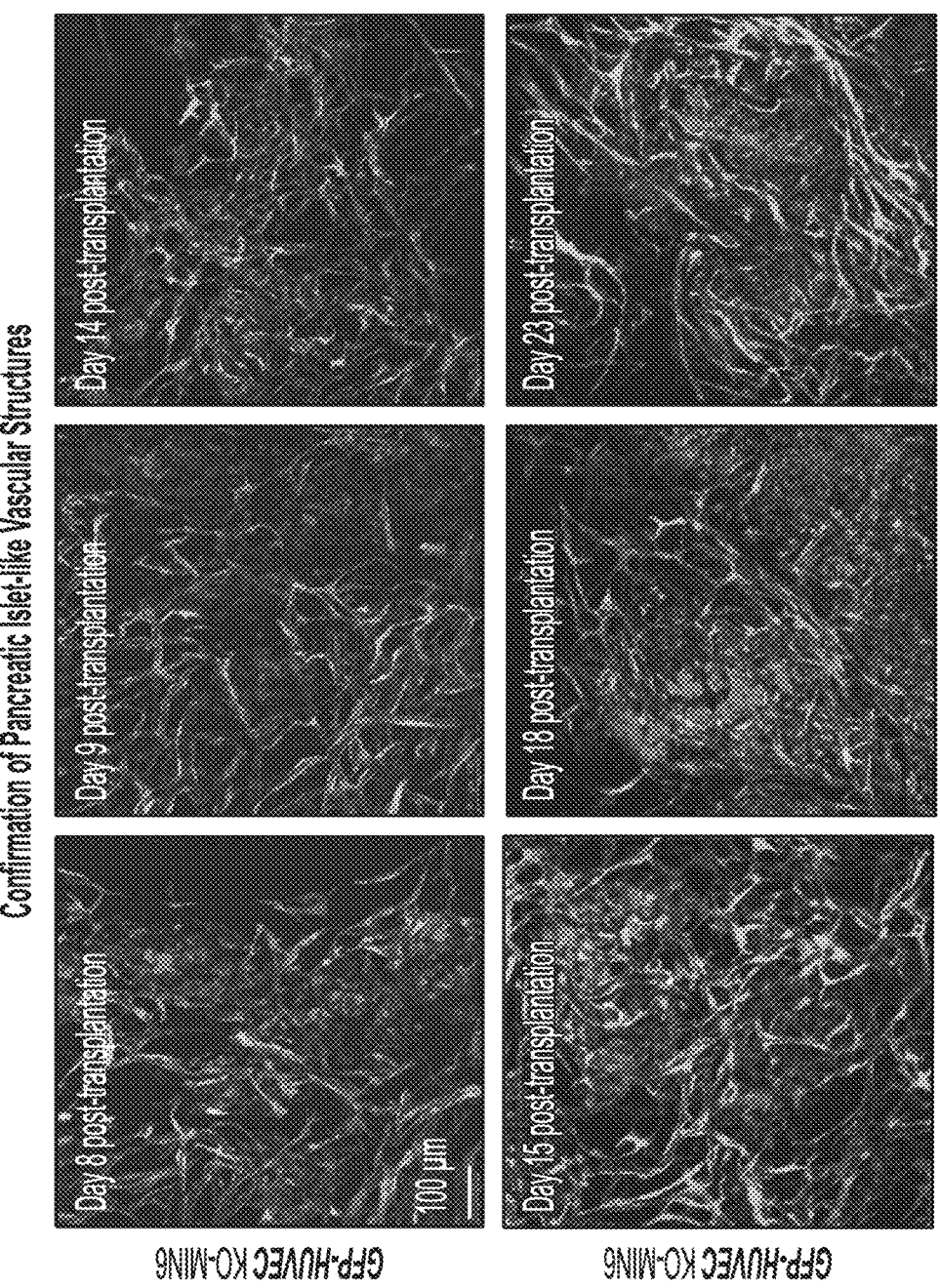

FIG. 26 This figure shows angiogenesis in pancreatic β cell populations. Vascular endothelial cells (HUVECs) are labeled with GFP and pancreatic β cells (MIN6) are labeled with KO.

Figure 27:
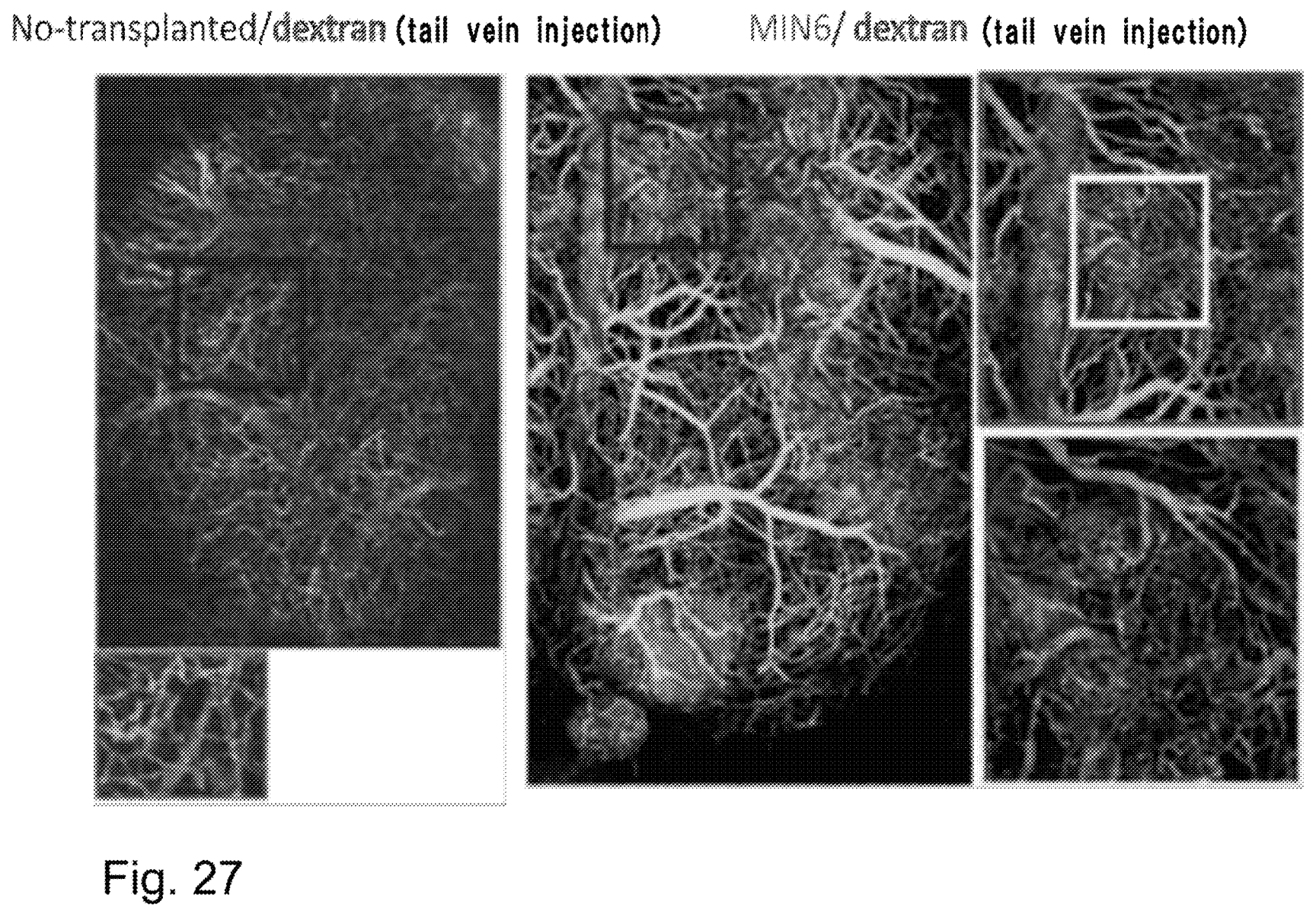

FIG. 27 This figure shows blood perfusion into pancreatic β cell populations. Blood flow is visualized with labeled dextran.

Figure 28:
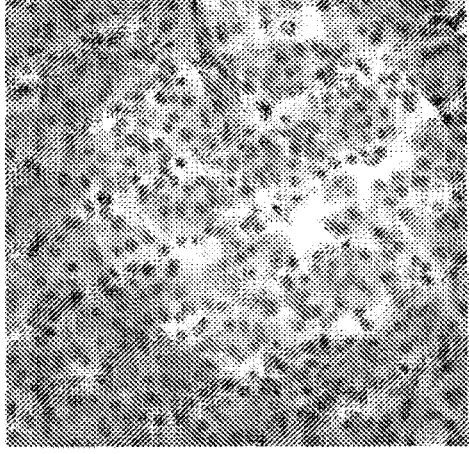

FIG. 28 This figure shows histological analysis of pancreatic β cell populations.

Figure 29E:
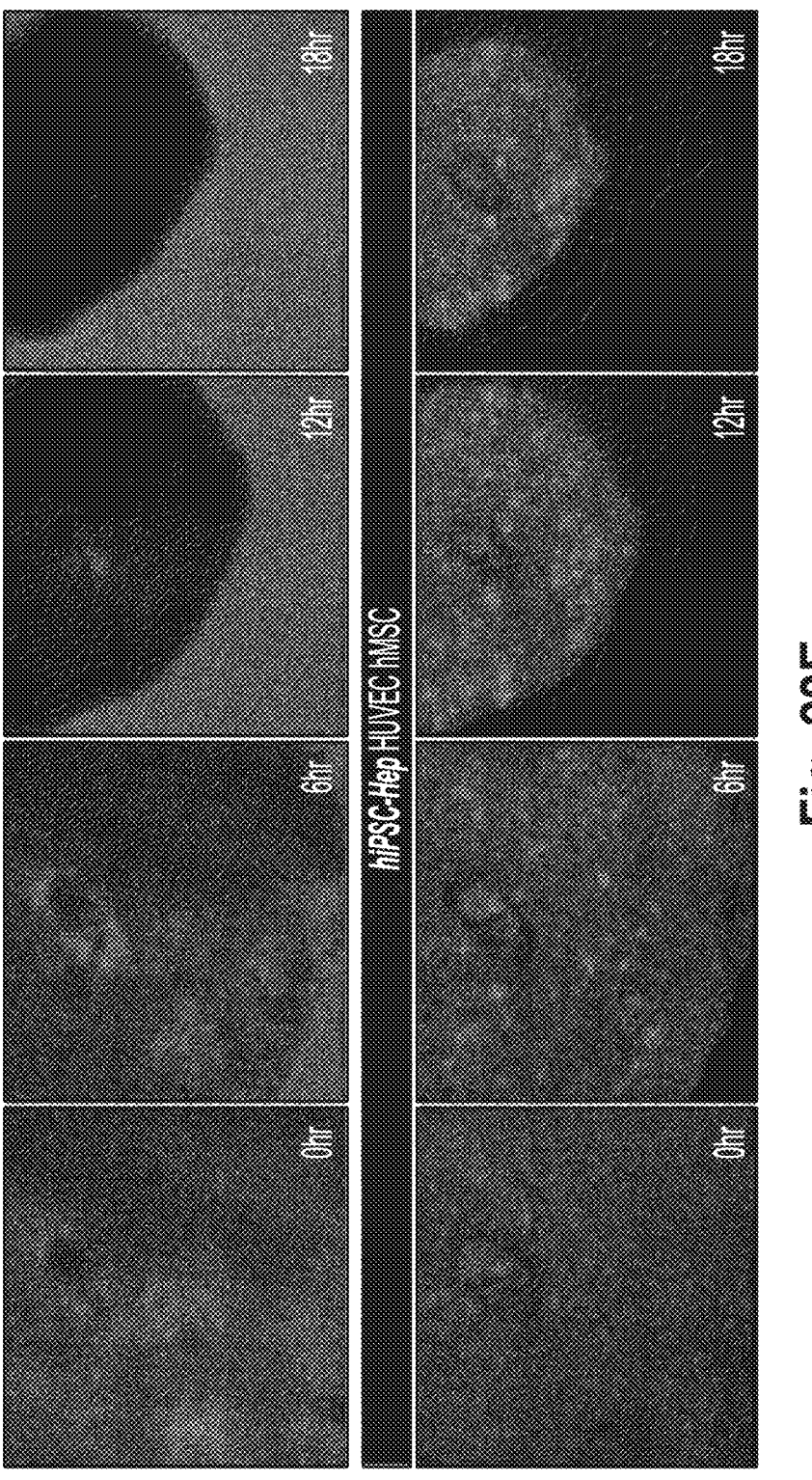
Figures 29F, 29G:
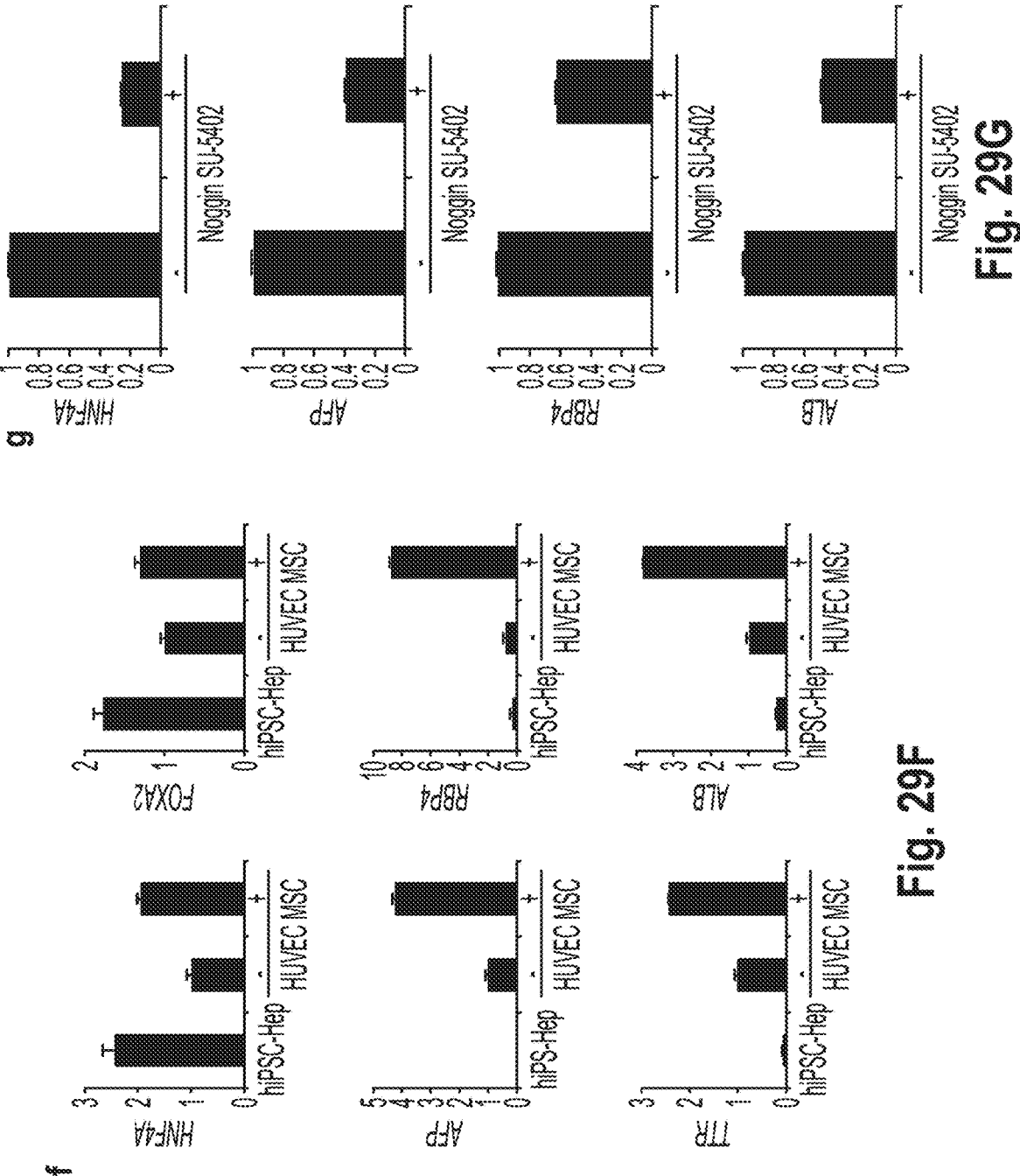
Figure 29H:
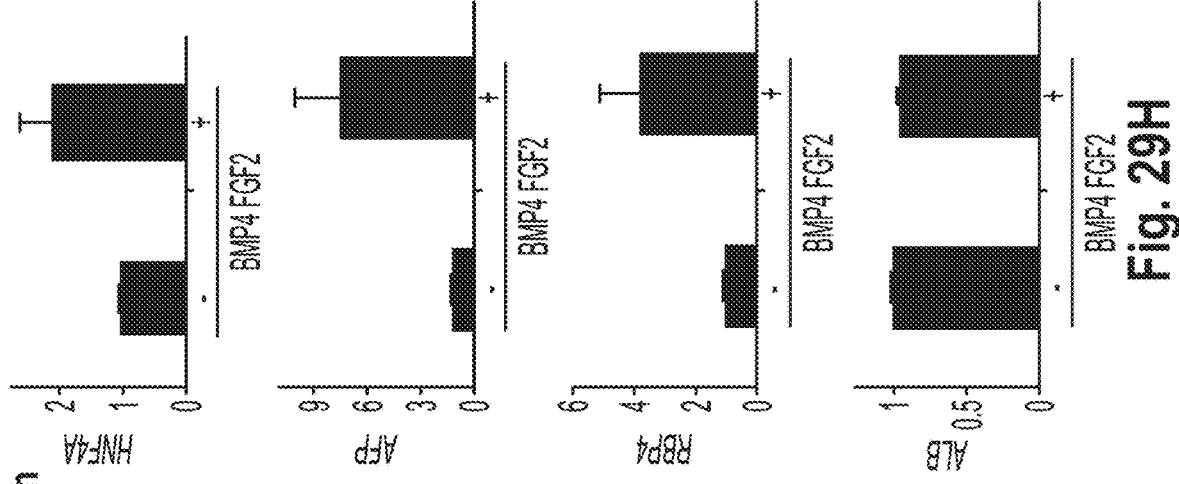

FIG. 29a-FIG. 29h Generation of human liver buds (hiPSC-LBs) from hiPSCs FIG. 29a—Schematic representation of the present technique. FIG. 29b—Liver endoderm differentiation (hiPSC-Hep) was evaluated by immunostaining for HNF4A and AFP at day 9 (results are shown as means±S.D., n=3). FIG. 29c—Three-dimensional self-organization of hiPSC-LBs as occurred when hiPSC-Heps were cocultured with HUVECs and hMSCs. Budding of endothelial cells was observed in hiPSC-LBs. Green: EGFP-labeled HUVEC; Red: KOFP (Kusabira Orange Fluorescent Protein)-labeled hMSC. Scale bar, 100 µm. FIG. 29d—Formation of hiPSC-LBs was not observed in culture systems without hMSCs. Scale bar, 1 mm. FIG. 29e—Autonomous organization of hiPSC-Heps labeled with Cell Tracker Red CMTMR (Molecular Probes) was confirmed by time-lapse imaging under confocal microscope. Images of confocal Z direction of highest power are projected. FIG. 29f—Expressions of HNF4A, FOXA2, AFP, RBP4, TTR and ALB from independent culturing of hiPSC-Heps or coculturing of the same with HUVECs and hMSCs in Transwell medium for 96 hours were analyzed by quantitative RT-PCR (qPCR) (results are shown as means±S.D., n=3). FIGS. 29g and 29h—As a result of expression analysis of hepatic differentiation marker genes, it was shown that addition of the BMP inhibitor Noggin (500 ng/ml) and the FGF inhibitor SU5402 (50 μM) inhibits the efficient hepatic maturation of hiPSC-Heps cocultured with HUVECs and hMSCs FIG. 29g. On the other hand, when BMP4 (20 ng/ml) and FGF2 (20 ng/ml) were added, it was confirmed that expressions of hepatic markers were enhanced although hiPSC-Heps were cultured independently FIG. 29h. (Results are shown as means±S.D., n=3).

FIG. 30 In vitro Characterization of hiPSC-LBs.
Panel a—Immunostaining for cytokeratin-8 and -18 (CK8. 18), AFP, PECAM1 (CD31), Flk-1, Desmin, PCNA and 5'-bromo-2'-deoxyuridine (BrdU). Scale bar, 100 μm. Panels b, c, d, e—The ratios of individual cell species are as follows: hepatoblasts, AFP positive/CK8. 18 positive; proliferating cells, (PCNA positive or BrdU positive)/CK8. 18 positive; endothelial cells, (CD31 positive or Flk1 positive)/DAPI positive; mesenchymal cells, Desmin positive/DAPI positive. The ratios of individual cell species in hiPSC-LBs were almost similar to those of E10.5 mouse LBs (mLBs). In panels b, c and d, the results are shown as means±S.D. In panel e, the results are shown as means±S.E.M. In all panels, n=3. Panel f—With respect to 83 liver-specific genes whose expressions increase gradually during both murine and human liver development, a heat map obtained from microarray data is shown. After in vitro liver bud formation, expressions of this group of liver specific genes remarkably increased. hiPSC-Def: hiPSC-derived embryonic endoderm cells; hiPSC-Hep: hiPSC-derived hepatic endoderm cells; hiPSC-IH: hiPSC-derived immature hepatocyte-like cells; hiPSC-MH: hiPSC-derived mature hepatocytes-like cells; hFLT: fetus (late pregnancy, 22-40 weeks) liver tissue; hALT: human adult (age 30) liver tissue.

Figure 31:
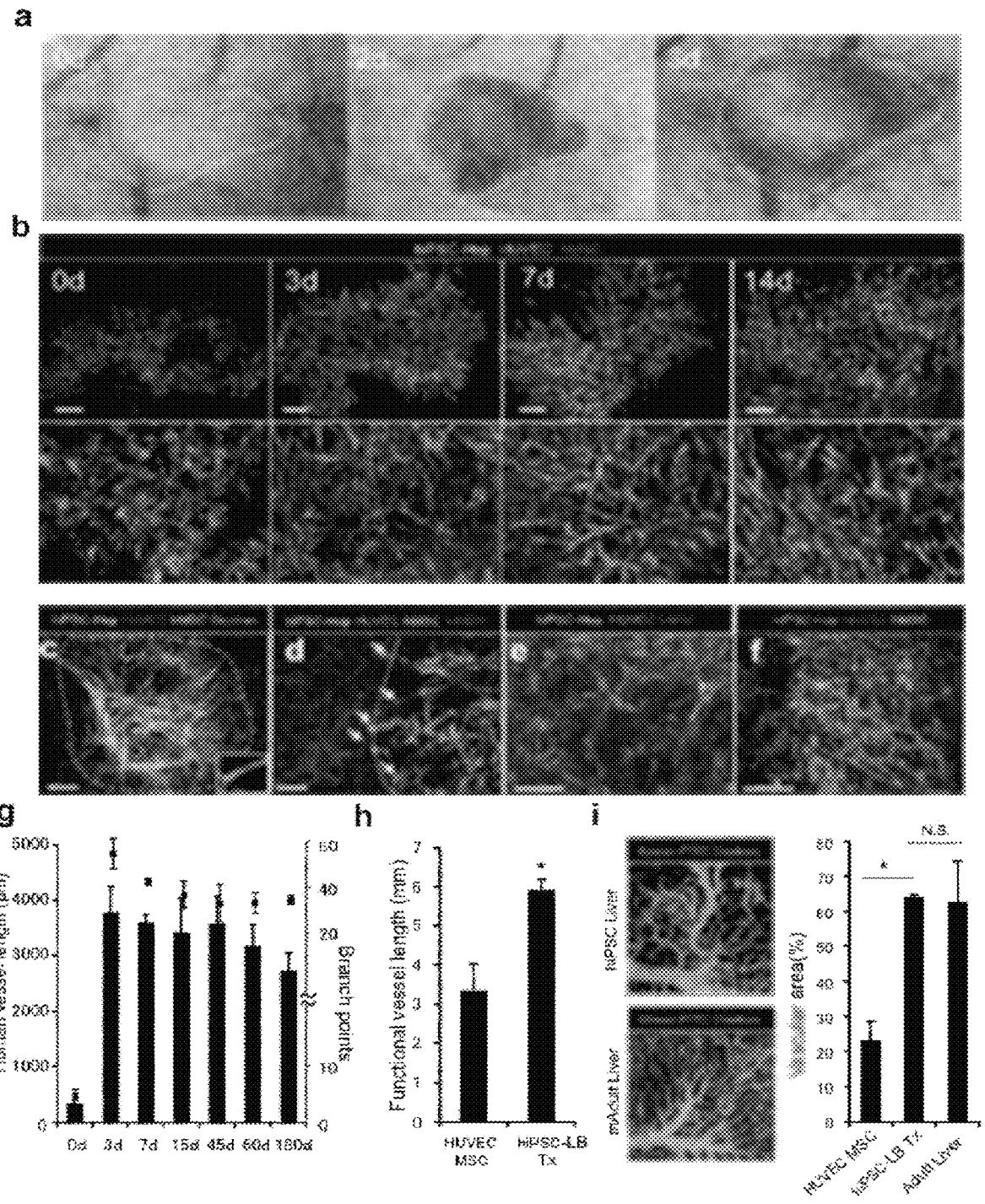

FIG. 31 Generation of human liver tissue with in vivo functional vascular networks Panel a—hiPSC-LBs were transplanted into a cranial window of NOD/SCID mouse. When the transplanted hiPSC-LBs were observed macroscopically, blood flow into human vessels was recognized within about 48 hours after transplantation. Dotted area indicates the transplanted hiPSC-LB. Scale bar, 1 mm. Panel b-Chronological live observation under confocal microscope revealed formation of vascular networks by vascular endothelial cells in the hiPSC-LBs. Panel c-Intravenous injection of dextran showed that hiPSC-LBs were completely perfused through functional human vascular networks by day 3 post-transplantation. This panel shows connections between human and mouse vessels. Dotted line indicates the end of the transplant. Scale bar, 500 μm. Panel d-Connections between HUVECs (green, GFP) and host vessels (blue, Alexa647-labeled mouse-specific CD31, intravenous injection) are directly visualized. Scale bar, 250 μm. Panels e and f—Localization of hMSCs- or hiPSC-derived cells in the formed liver tissue was observed at day 15 post-transplantation. Scale bar, 100 μm panel e and 250 μm panel f. Panel g—Quantitative analysis of human vessels in hiPSC-LB transplant in vivo (results are shown as means±S.E.M., n=3). Panel h—Lengths of functional vessels were compared between hiPSC-LB and HUVEC hMSC transplants (Tx). (Results are shown as means±S.E.M., n=5, *: P<0.01). Panel i—Intravital confocal observation after infusion of FITC-dextran. Vascularization in hiPSC-LB-derived tissue is almost equivalent to that in normal adult mouse liver. (Results are shown as means±S.E.M., n=5, *: P<0.01).

Figure 32:
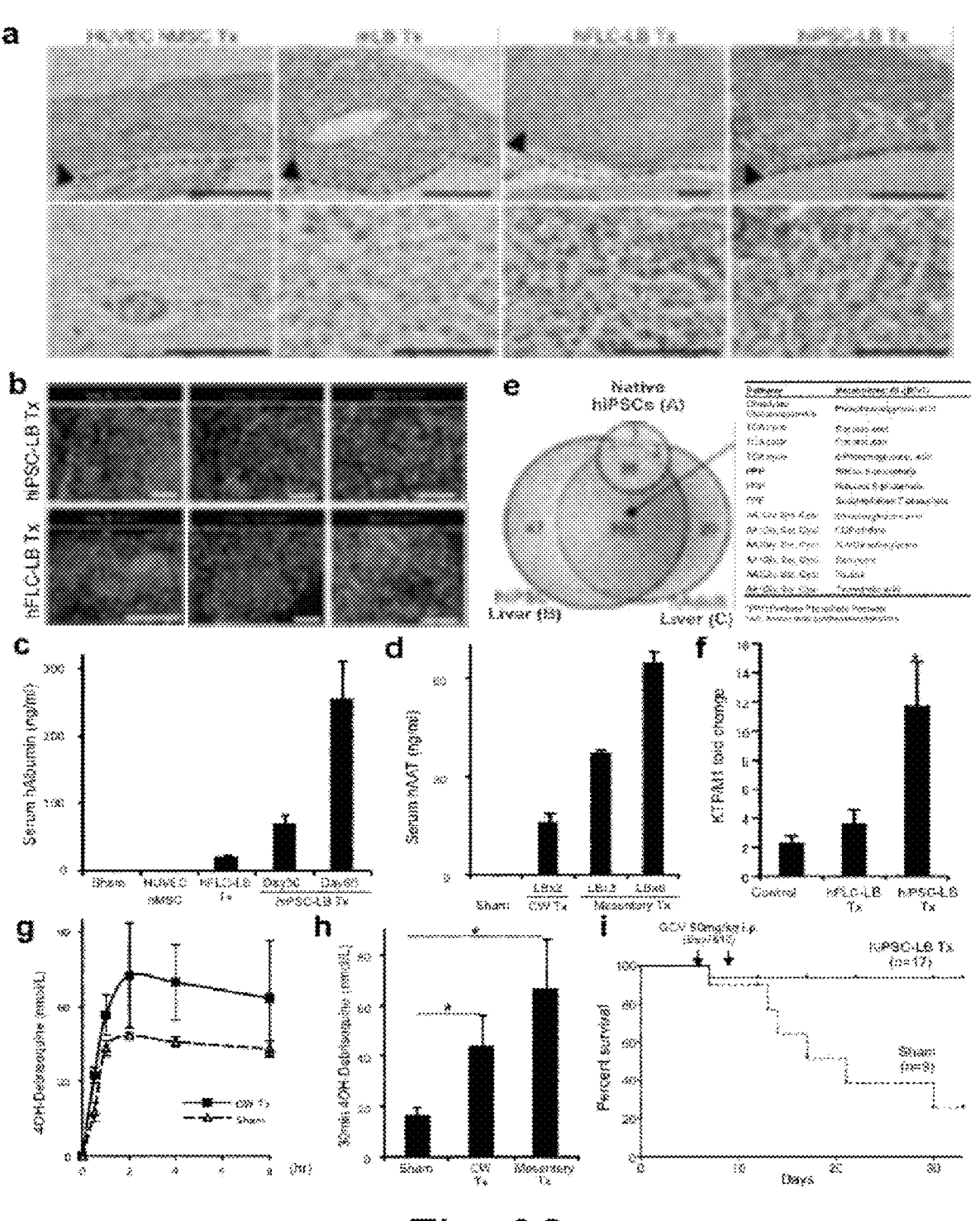

FIG. 32 Functional analysis of hiPSC-derived liver tissue. Panel a—HE staining of tissue sections at day 60 post-transplantation showed formation of hepatic cords containing sinusoid-like endothelial cells, whereas such formation was not recognized in HUVEC hMSC transplants (Tx). Dotted line indicates the border of the transplant on the brain. Scale bars, 200 μm (upper panels) and 100 μm (lower panels). Panel b—Immunostaining showing the expressions of hepatic markers in hiPSC-LB- and hFLC-LB-derived tissues. Scale bars, 100 μm (left, middle) and 25 μm (right). Panels c and d—Levels of human ALB and AAT in mouse serum over time. (Results are shown as means±S.E.M., n=6 in panel c and n=3 in panel d). ATT production was proportional to the number of hiPSC-LB transplants. Two LBs were transplanted into the cranium and 3 or 6 LBs were transplanted into the mesentery. Panel e—Venn diagram showing the metabolic profiles of hiPSC-LB transplants measured by CE-TOFMS (FIG. 31a and FIG. 31b). Of the metabolites found in hi-PSC-LB transplants, 78% was consistent with those found in adult liver. Right panel shows major metabolites which were found in both hiPSC-LB transplants and normal human adult liver, and not found in original hiPSCs. Panel f—Human-specific ketoprofen metabolite detected in mouse urine by mass-spectrometry. (Results are shown as means±S.E.M., n=3, *: P<0.05). Panel g—Formation of serum metabolite 4-OHDB in debrisoquine-administered mice (oral administration) was examined by pharmacokinetic analysis. Panel h—Formation of serum metabolite 4-OHDB was compared between intracranially transplanted (CW) and mesenterically transplanted mice. (Results are shown as means±S.E.M., n=3, *: P<0.05). Panel i—Kaplan-Meier survival curves of TK-NOG mice after hiPSC-LB transplantation. Wilcoxon statistical analysis showed a significant difference between curves of the sham-operated control group and the hiPSC-LB transplanted group (P=0.0120).

Figure 33:
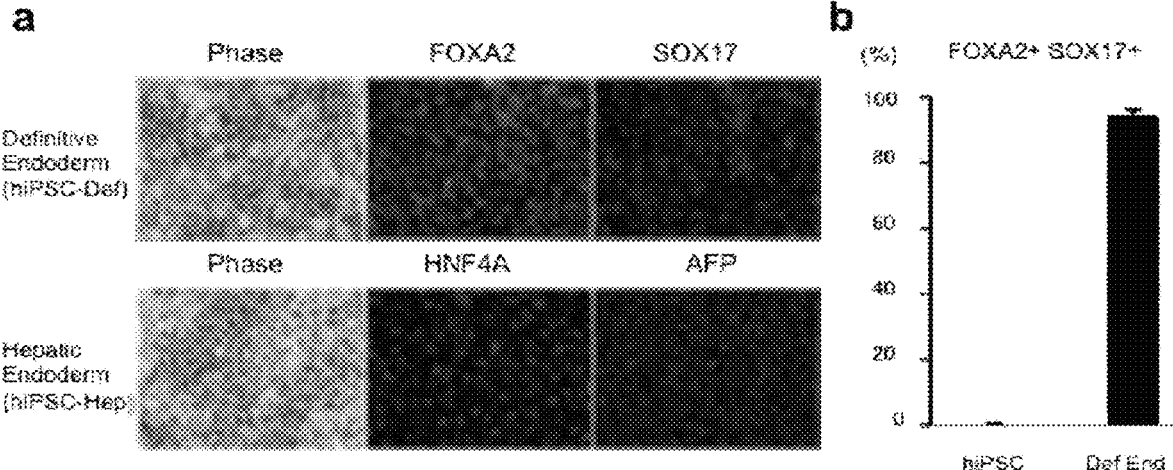

FIG. 33 Induction of early differentiation of hiPSCs into hepatic endoderm. Panel a—Differentiation into embryonic endoderm and differentiation into hepatic endoderm both from hiPSCs were monitored by immunostaining for FOXA2, SOX17, HNF4A and AFP at day 6 and 9. Panel b—Efficiency of differentiation into embryonic endoderm was assessed at day 6 of induction by immunostaining for FOXA2 and SOX17 (results are means±S.D., n=3).

Figure 34:
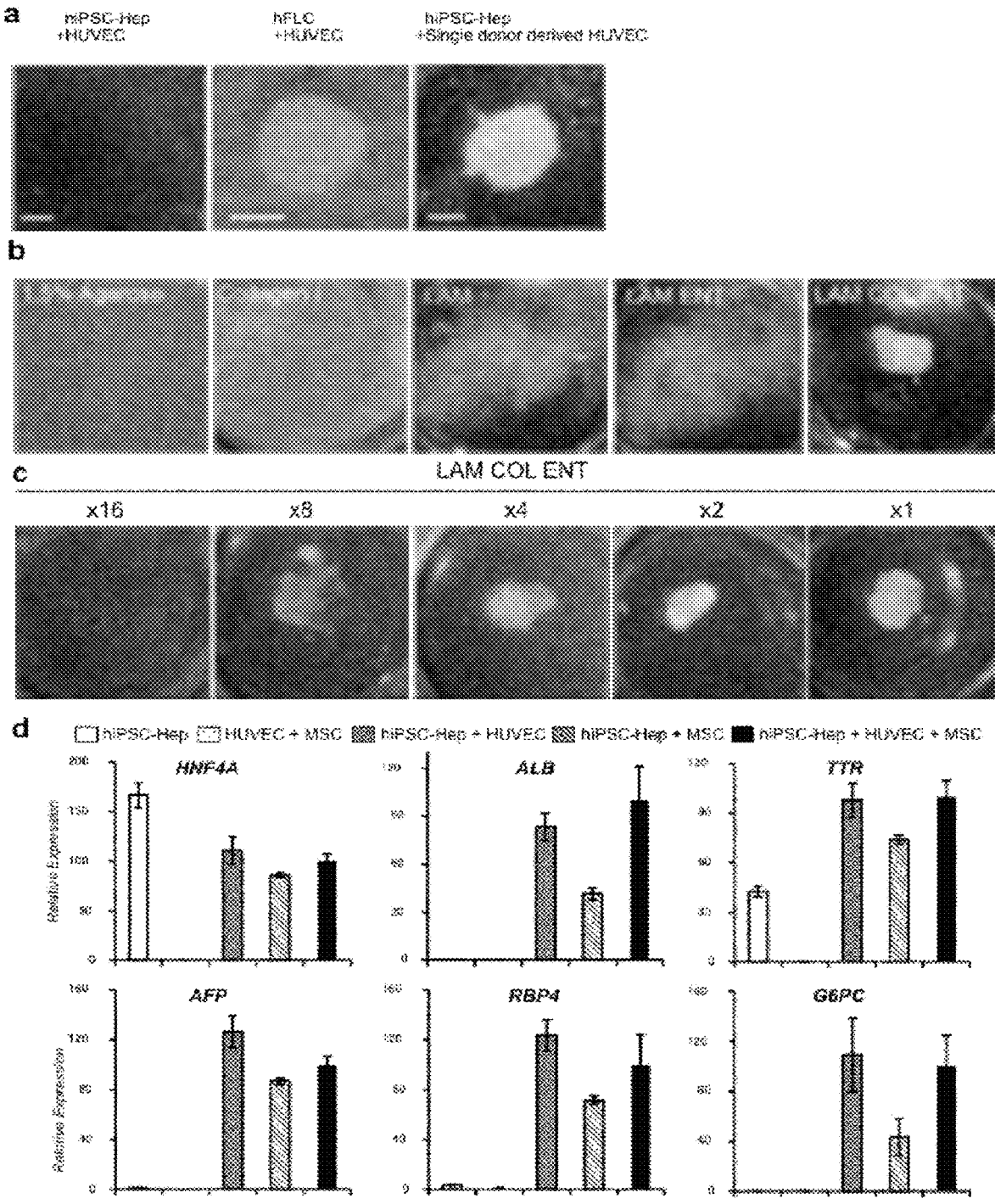

FIG. 34 Optimization of conditions for hiPSC-derived LB formation in vitro.
Panel a—Formation of liver buds (LB) by coculturing with various cell types. Bars, 1 mm. Panel b—Hepatic endoderm cells were cocultured with HUVECs and hMSCs on various matrix proteins. Formation of hiPSC-derived LBs (hiPSC-LBs) was observed when cells were seeded on Matrigel (LAM COL ENT). LAM: laminin; ENT: entactin; COL: collagen IV. Panel c—Effect of matrix protein concentrations on LB formation. Panel d—qPCR gene expression analysis of hiPSC-LBs. By coculture with endothelial cells and mesenchymal cells, significant increase was observed in the expression levels of early hepatic differentiation markers ALB, RBP4, TTR and G6PC (results are means±S.D., n=3).

Figure 35:
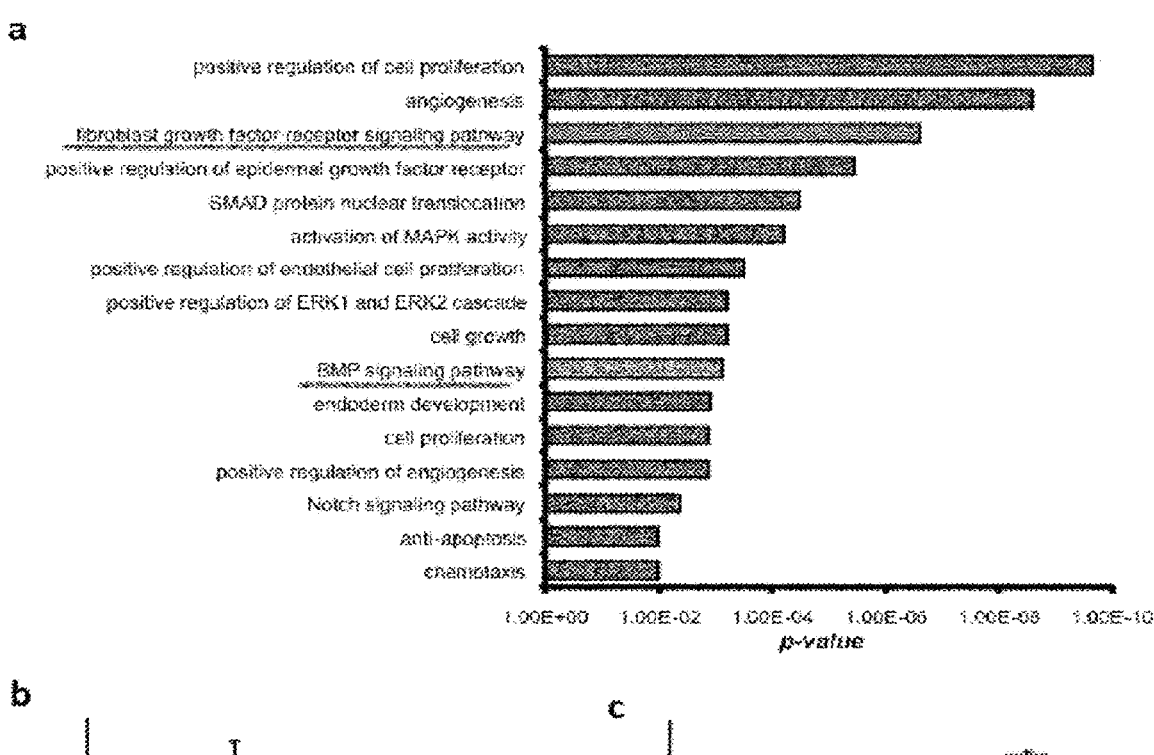
Figure 35:
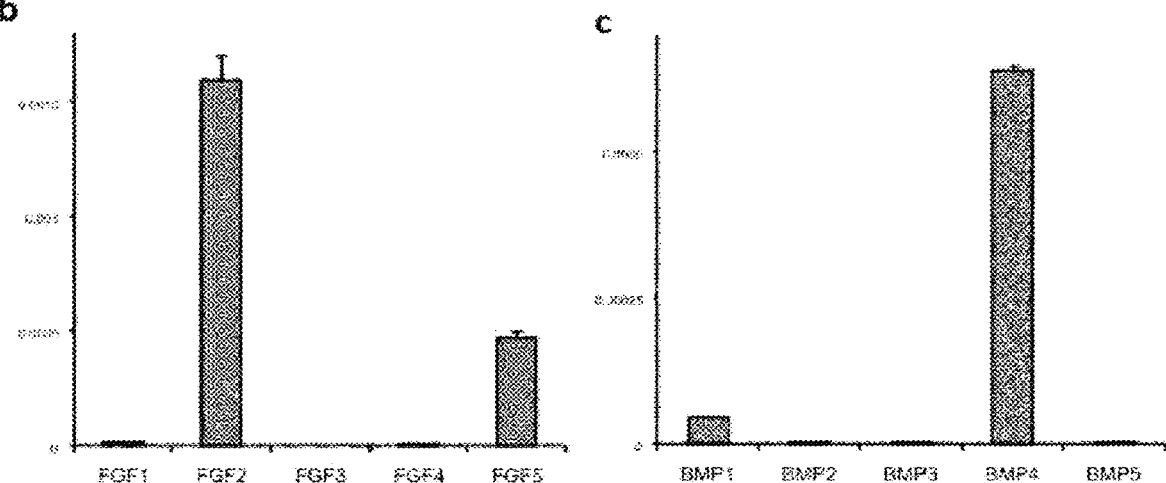
Figure 36A:
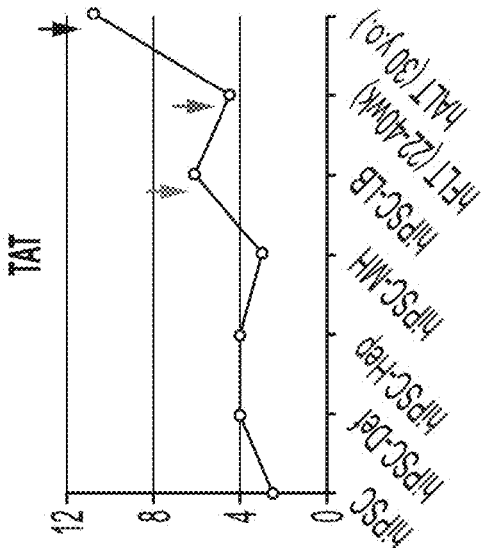
Figure 36A:
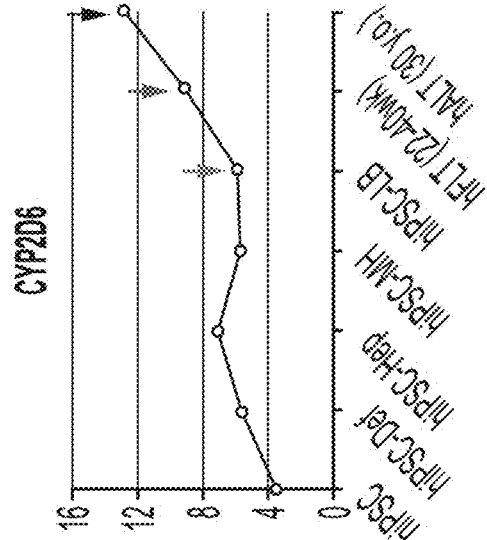
Figure 36A:
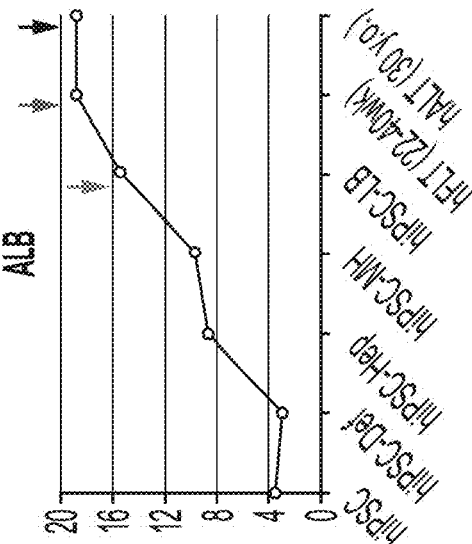
Figure 36A:
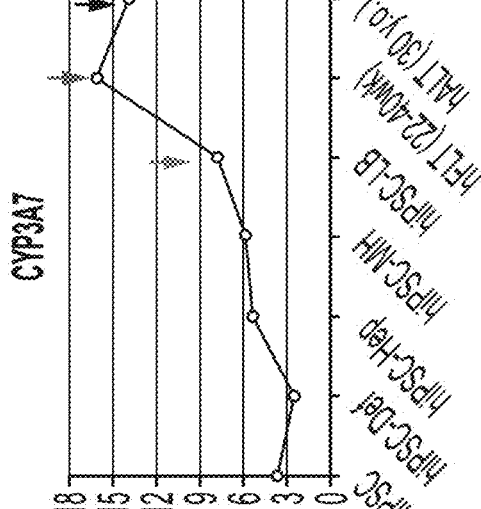
Figure 36A:
Figure 36B:
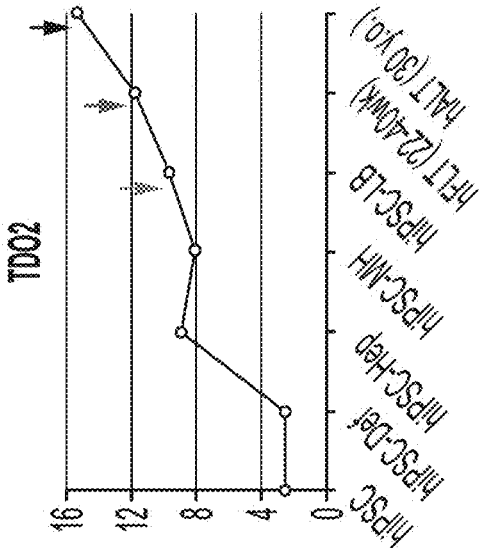
Figure 36B:
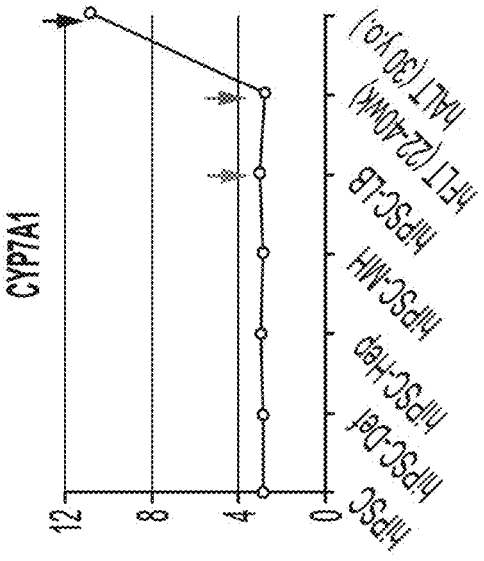
Figure 36B:
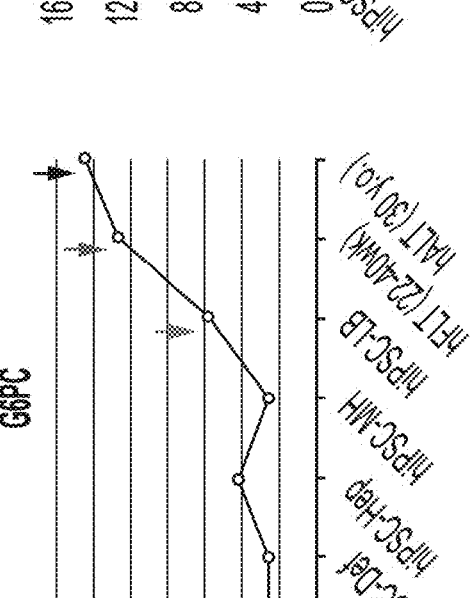
Figure 36B:
Figure 36C:
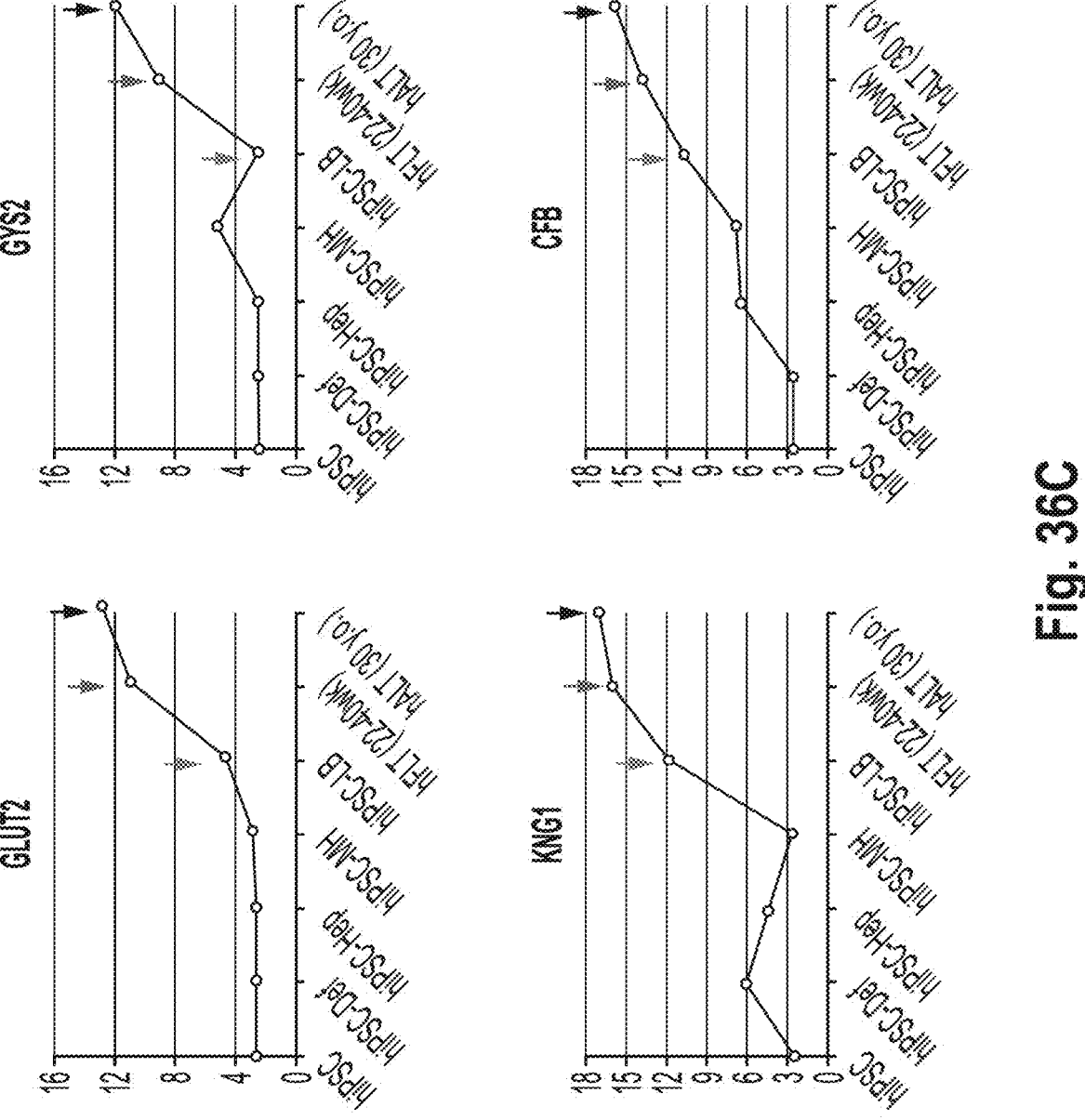
Figure 36D:
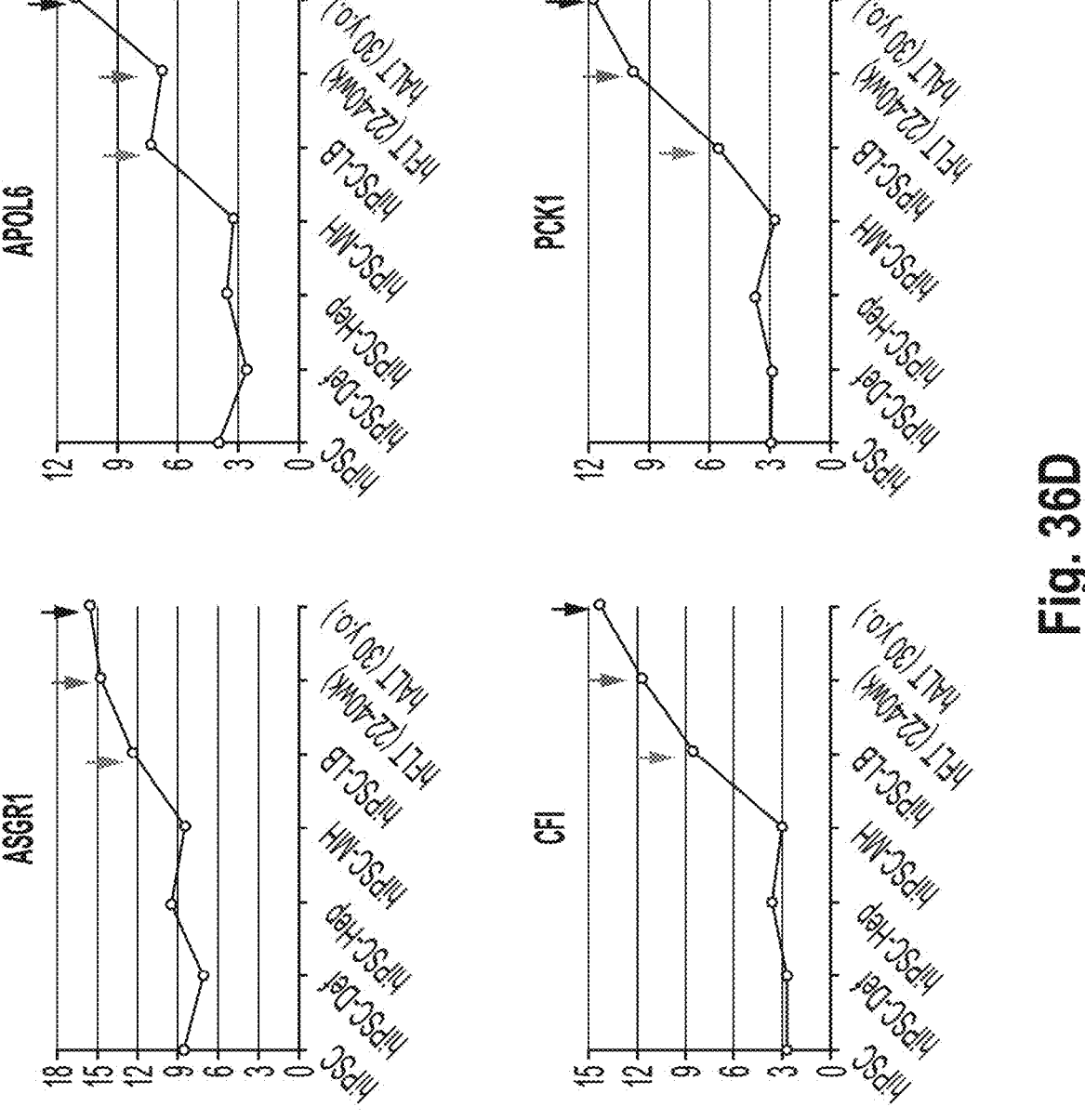
Figure 36E:
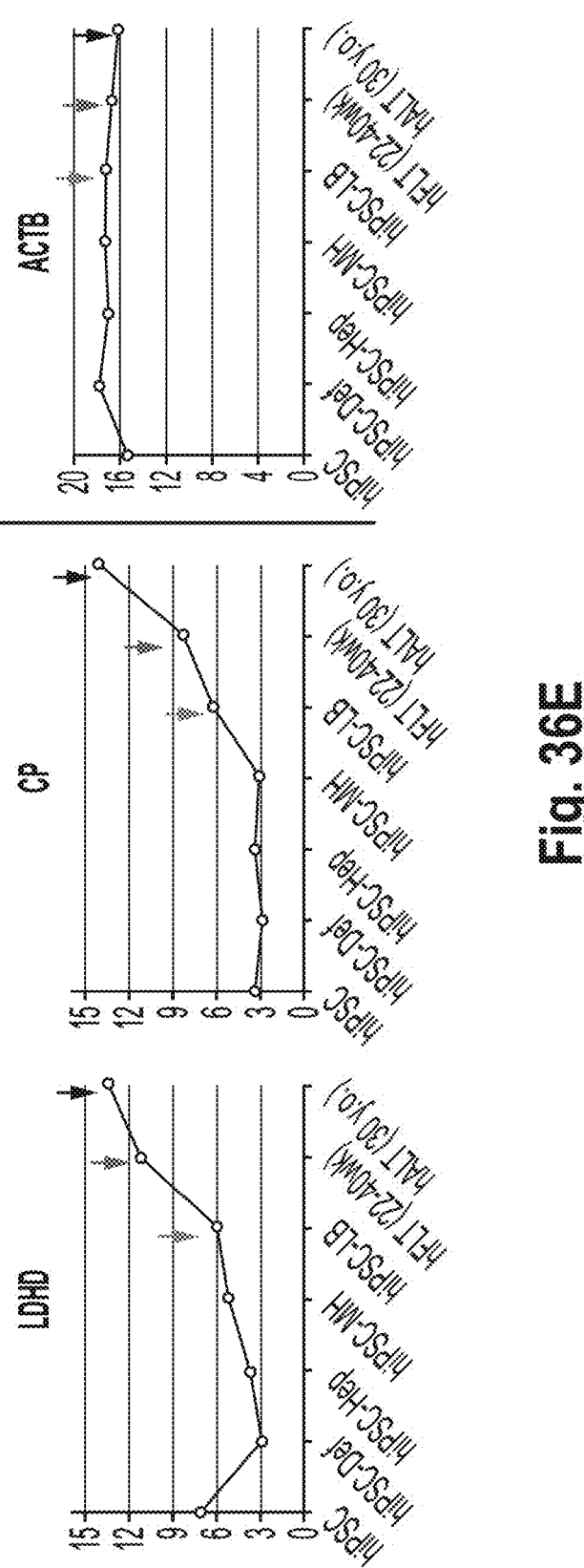

FIG. 35 Identification of humoral factors derived from cocultures with stromal cells.
Panel a—Gene ontology (GO) analyses of 5000 genes up-regulated in endothelial and mesenchymal cell coculture compared with undifferentiated hiPSCs. Bars represent the significance (P value) of a specific GO category in GO:0008083 (growth factor activity) on biological processes. Among stromal cell-specific genes, FGF signaling (red) and BMP signaling (blue) pathways were emphasized.

Panels b and c—qPCR analyses of Panel b—FGFs and Panel c—BMPs showing that FGF2 and BMP4 are highly expressed in endothelial and mesenchymal cells.

FIG. 36A-36E Expression profiling of representative hepatic marker genes by microarray analysis Gene expressions of hiPSC-LBs were in an appropriate stage, compared with those of human fetus (22-40 gestational week) and human adult (30 years old) liver tissues. TAT: tyrosine aminotransferase; G6PC: glucose-6-phosphatase; TDO2: tryptophan 2,3-dioxygenase; GLUT2: glucose transporter 2; GYS2: glycogen synthase 2; APOL6: apolipoprotein L; KNG1: kininogen 1; CFB: complement factor B; CFI: complement factor I; PCK1: phosphoenolpyruvate carboxynase; LDHD: lactate dehydrogenase D; CP: ceruloplasmin; ACTB: actin beta.

Figure 37:
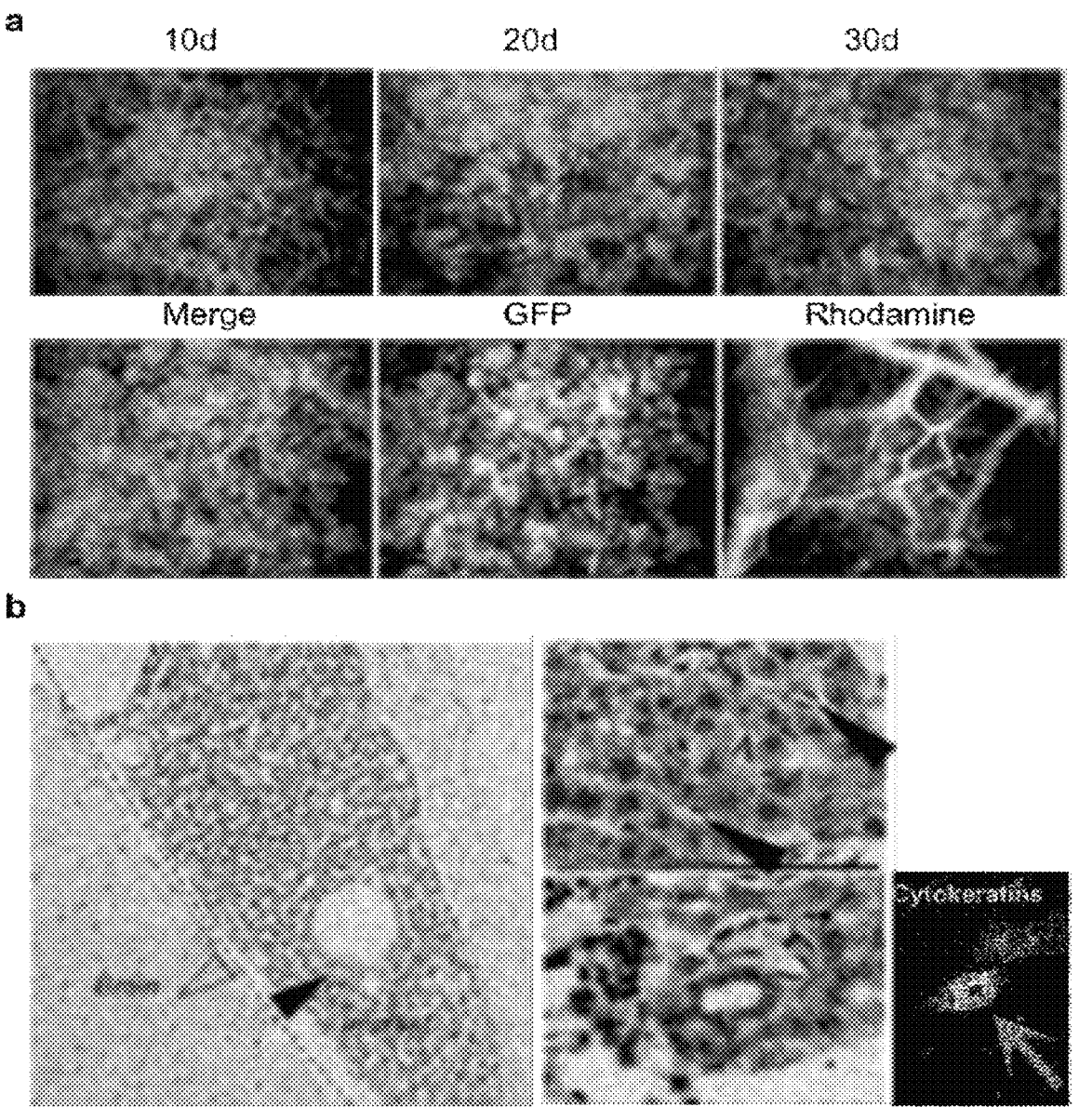

FIG. 37 Generation of murine liver tissue from mouse liver bud-derived cells.

Panel a—Chronological intravital fluorescence imaging of EGFP-labeled E13.5 mFLC transplants. At day 30 post-transplantation, tetramethylrhodamine-conjugated dextran was injected via the tail vein to reveal functional blood vessels.
Panel b—HE staining of generated murine liver tissue. Hepatocyte clusters contained sinusoidal endothelial cells (right, arrowhead). Cytokeratin immunostaining confirmed the formation of bile duct-like structures inside the clusters (right, lower panel).

Figure 38:
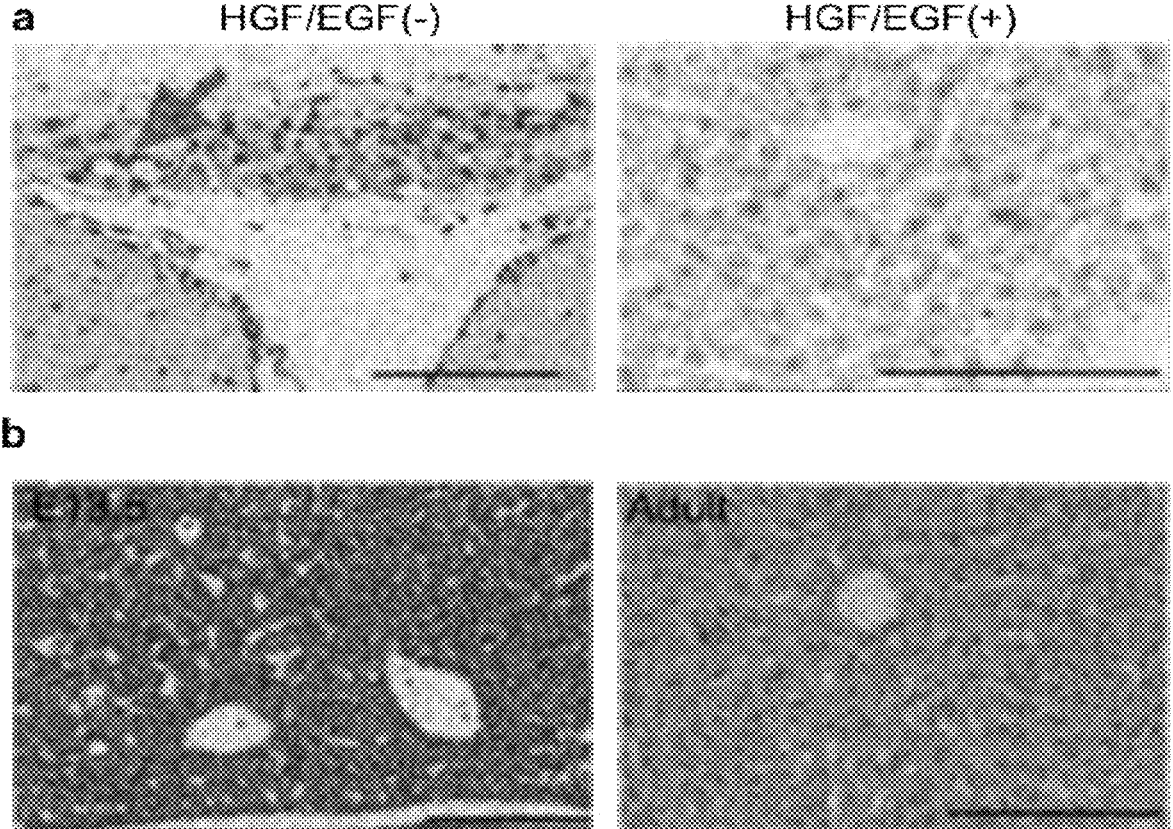

FIG. 38 Histological comparison among generated murine liver tissue, E13.5 fetal liver tissue and adult liver tissue Panel a—Addition of HGF (500 ng/ml) and EGF (200 ng/ml) enhanced the recapitulation of liver tissue.

Panel b—The generated murine liver tissue had histological characteristics similar to those of adult liver tissue rather than those of E13.5 fetal liver tissue. Bars, 200 μm.

Figure 39:
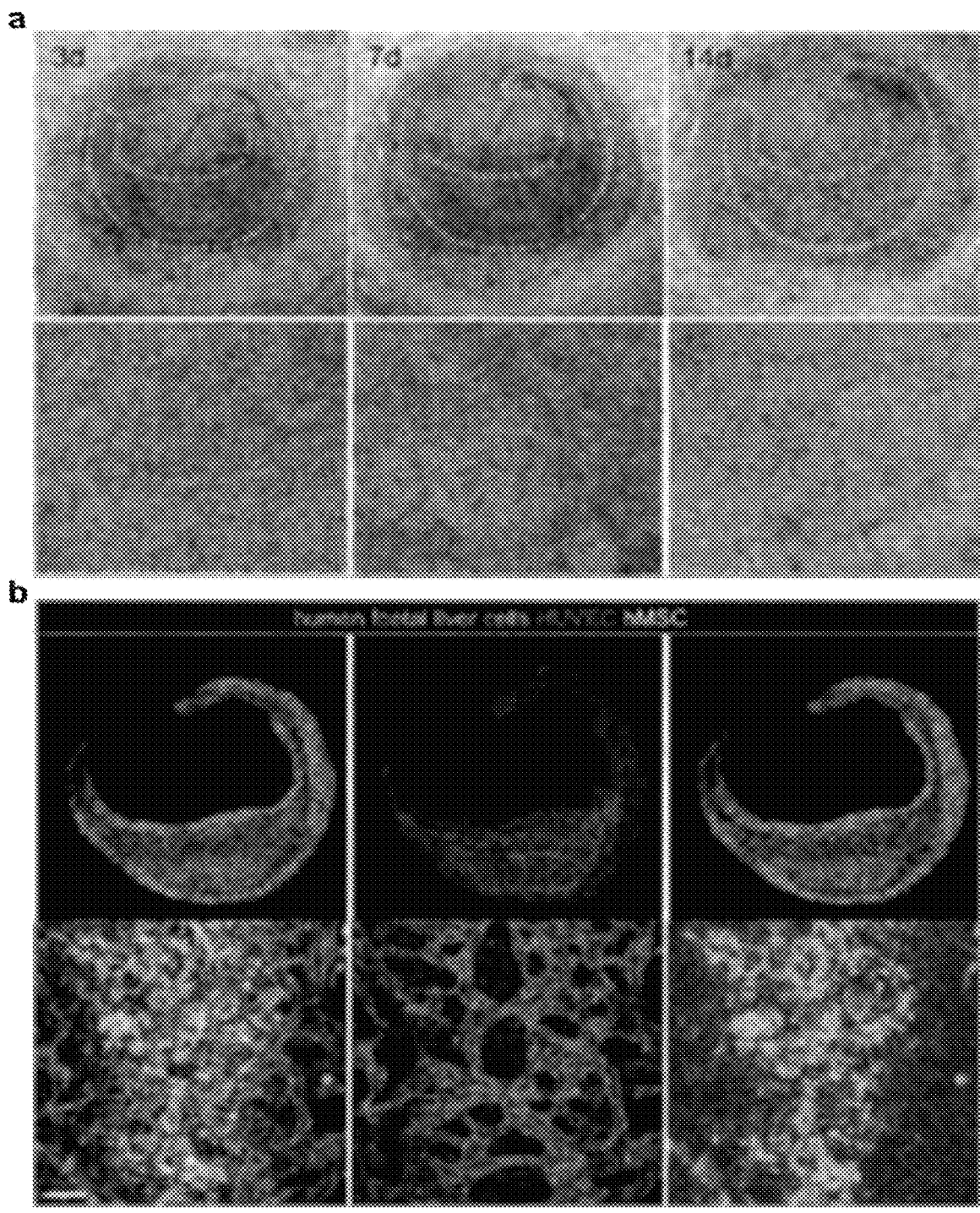

FIG. 39 In vivo transplantation of hFLC-LBs

In vivo grown hFLC-LBs were transplanted under the cranial window of NOD/SCID mice. Panel a—Chronological macroscopic images showing the progress of vascularization. Functional blood flow began at day 3, and vessels became more sophisticated and stabilized over time.

Panel b—Intravital confocal images of hFLC-LB derived tissues at day 3. Green: hFLCs expressing EGFP; red, HUVECs expressing KOFP. Bar, 100 μm.

Figure 40:
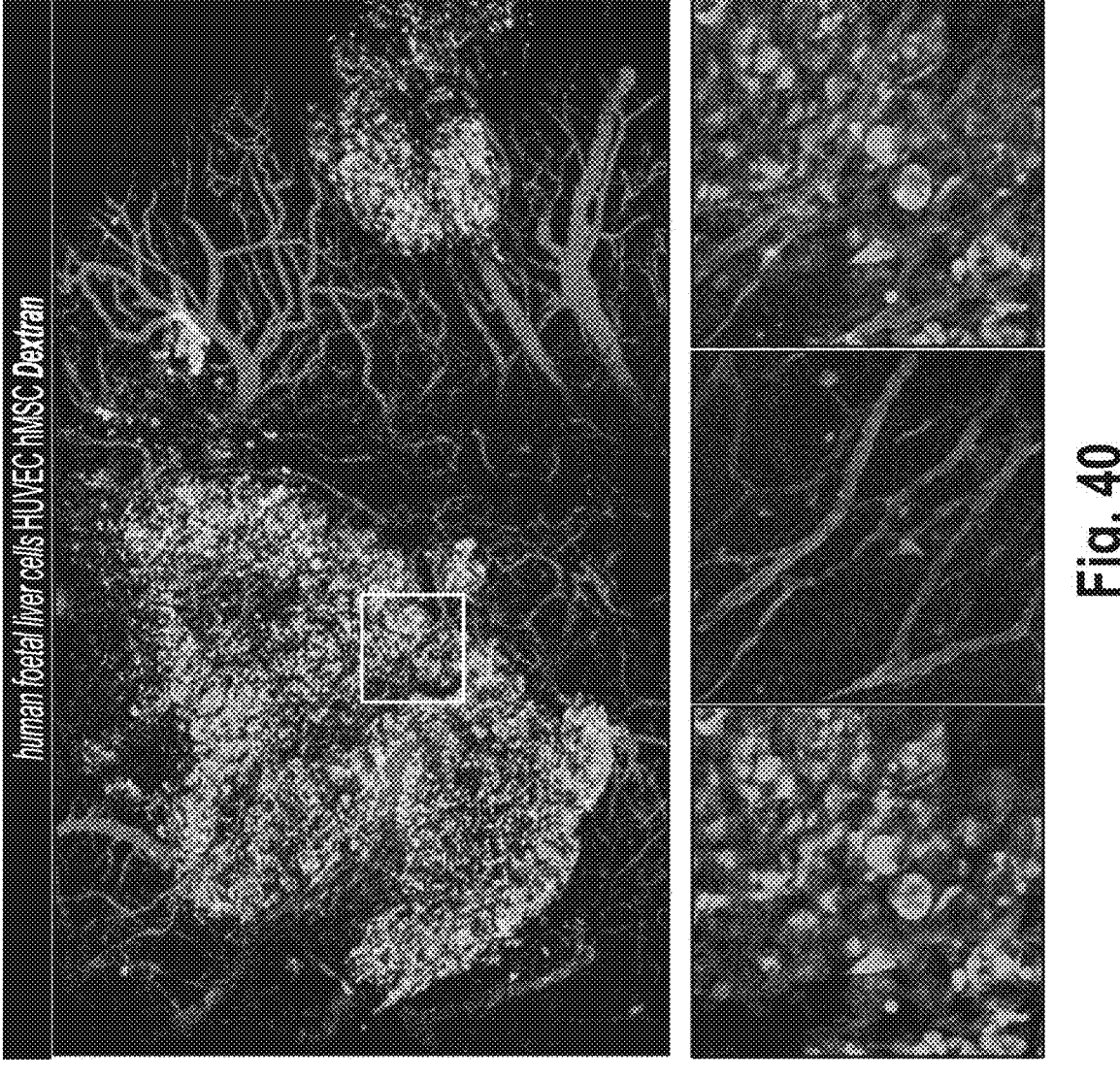

FIG. 40 In vivo formation of functional vascular networks inside the hFLC-derived liver tissue.

Patent vasculature shown by Texas Red-conjugated dextran infusion at day 3.

Figure 41:
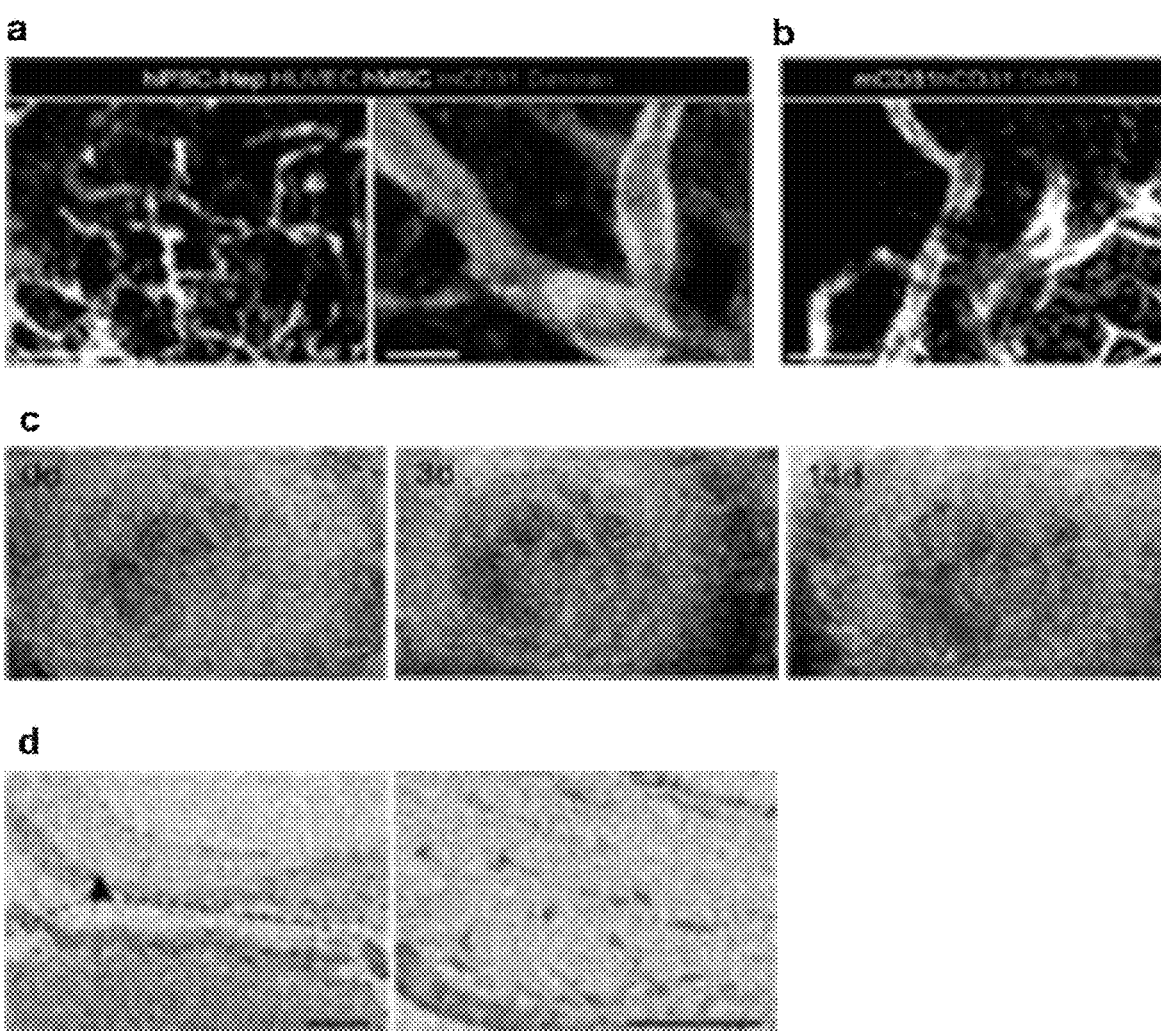

FIG. 41 Formation of human vascular networks connected with host vessels is essential for successful hiPSC-Hep engraftment.
Panel a—Direct visualization of the connections between HUVECs (green, GFP) and host vessels (blue, Alexa647-conjugated mouse-specific CD31, injected i.v.). Perfused vessels were visualized by i.v. injection of fluorescence-conjugated dextran (red) at day 10. Bar, 250 μm and 25 μm.

Panel b—Species-specific CD31 immunostaining of explanted hiPSC-LB transplants showing direct connection between human and mouse vessels in hiPSC-derived liver tissues. Bar, 100 μm.

Panel c—Macroscopic images of hiPSC-hMSC transplants without endothelial cells at multiple time points. No identifiable blood vessels are visible.

(a) Panel d—HE staining of hiPSC/hMSC transplants showed fibrotic tissue formation at day 30 post-transplantation. This result indicates the failure of hiPSC-derived hepatic cell engraftment, suggesting the necessity of endothelial cells. Bars, 100 μm.

Figure 42:
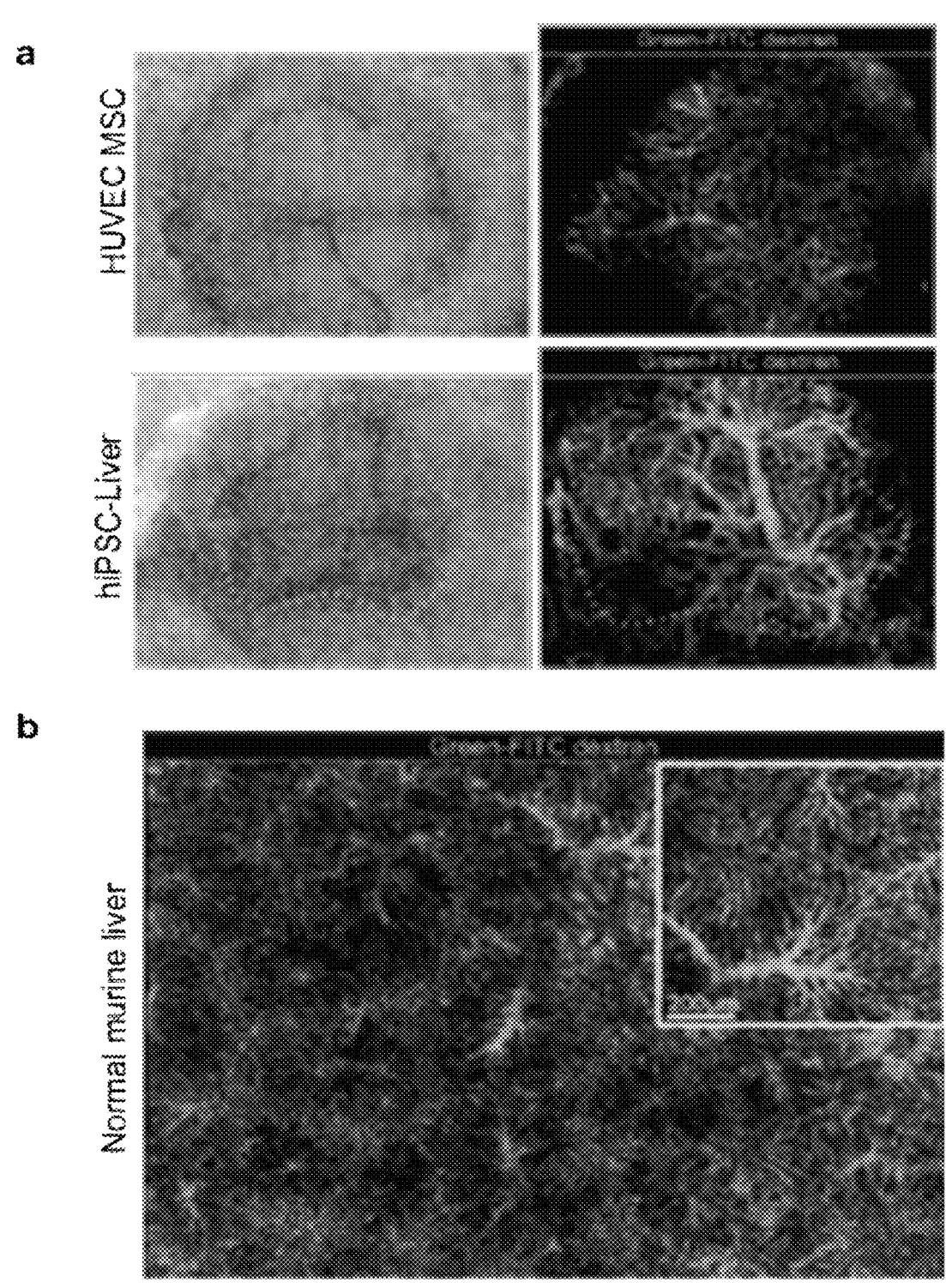

FIG. 42 Intravital imaging of generated human liver and normal murine liver vasculature in vivo.

Panel a—The vasculature of HUVEC hMSC alone (upper) or hiPSC-LB transplant (lower) visualized by FITC-conjugated dextran infusion at day 30 post-transplantation.

Panel b—Live imaging of normal murine liver where blood flow is visualized with FITC-conjugated dextran. Bar, 200 μm.

Figure 43:
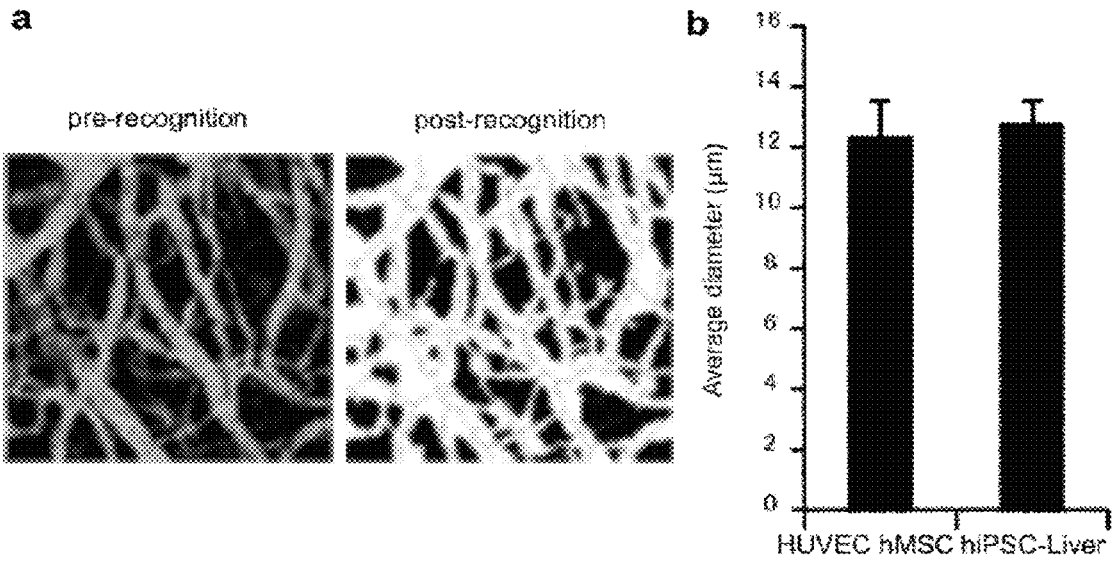
Figure 43:
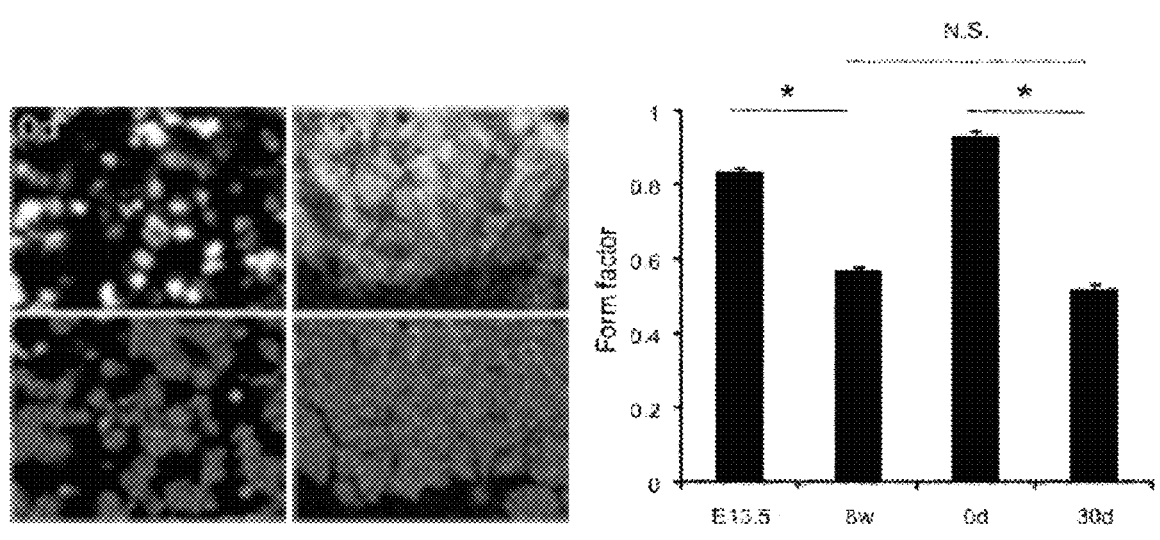

FIG. 43 Intravital evaluation of the human vascular networks and hepatocyte morphology inside liver tissue Panel a—Functional human vessels visualized by FITC-conjugated dextran infusion. Image projection (left panel) was then processed using MetaMorph Angiogenesis Module software. Right panel shows representative segmentations of each image.

Panel b—Determination of vessel diameters (means±S.D.; n=3).

Panel c—Intravital images of the hepatocyte morphology inside hiFLC-LB transplants and estimate of cell roundness (form factor). (Results are shown as means±S.E.M.; n=3; more than 100 cells were measured for each sample; *: P<0.05; N.S.: not significant.)

Figure 44:
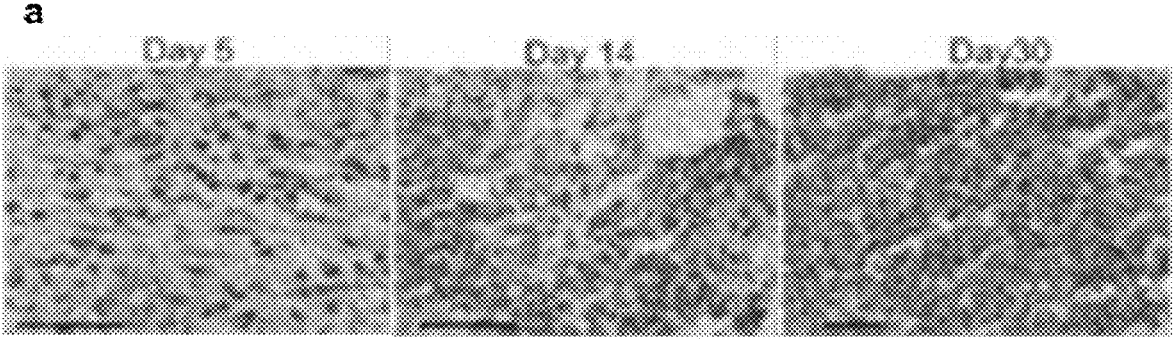
Figure 44:
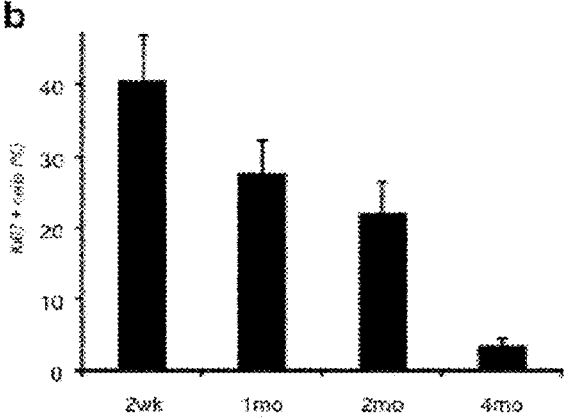

FIG. 44 Time course-dependent changes of hiPSC-LB transplants in vivo.

Panel a—Long-term HE staining of hiPSC-LB transplants. Round shaped hiPSCs-derived hepatoblasts expanded extensively and differentiated into immature hepatocytes wih enlarged cytoplasm, as observed in normal murine liver development[1]. Bars, 50 μm.

Panel b—Determination of proliferating cell count inside the hiPSC-LB transplants in vivo by Ki67 immunostaining 2 weeks and 1, 2 and 4 months post-transplantation.

Figure 45:
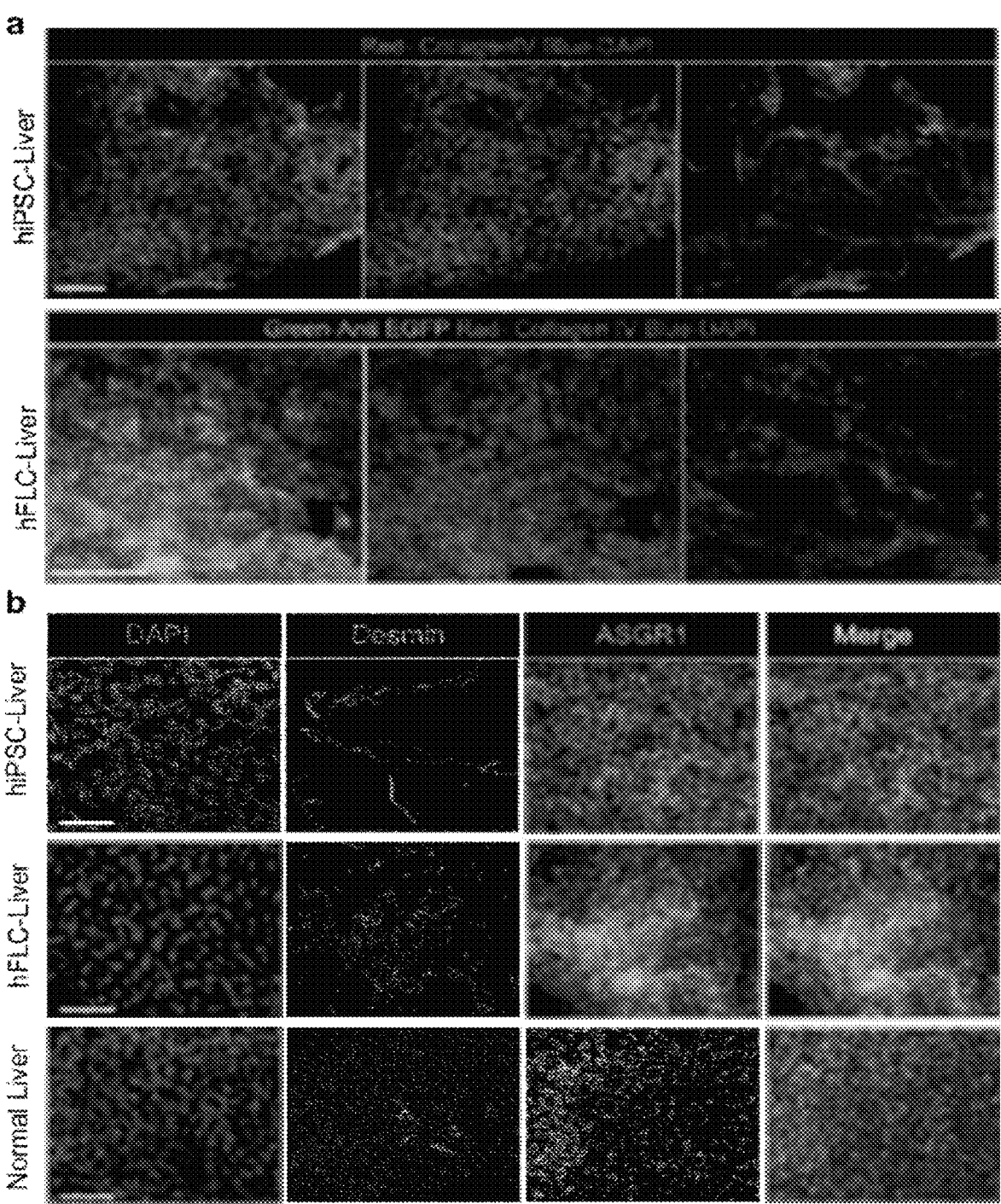

FIG. 45 Whole mount immunostaining of hiPSC-LB or hFLC-LB transplants.

Panel a-Collagen IV immunostaining showing the reconstitution of basement membrane protein inside the generated liver tissues. Bars, 100 μm and 50 μm.

Panel b—The transplant-derived human liver tissue composed of mature hepatocytes and mesenchymal cells, resembling normal murine liver tissue. Bars, 50 μm.

Figure 46:
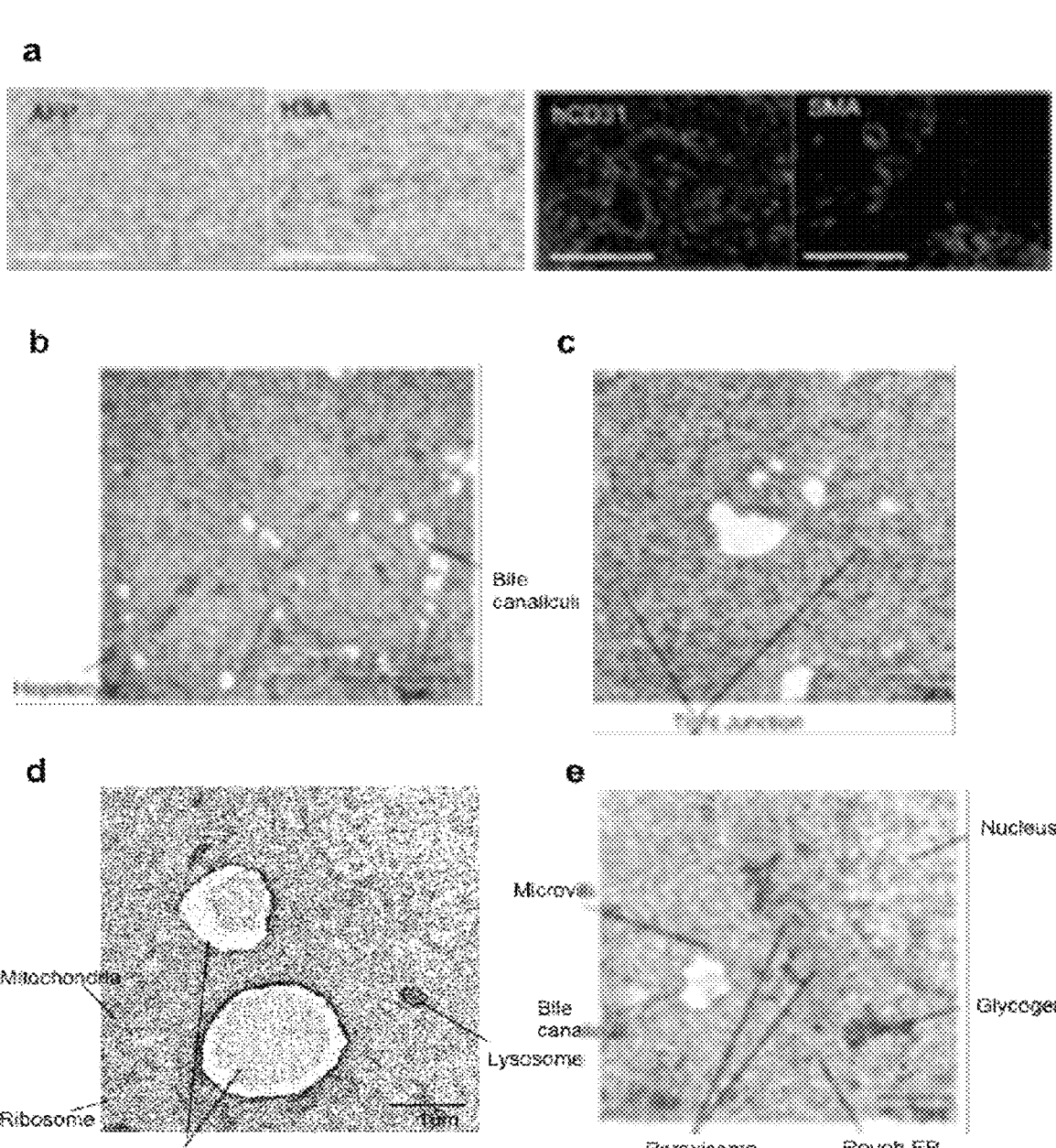

FIG. 46 Immunostaining and transmission electron microscopy analyses of hFLC-LB derived human liver tissue Panel a—Liver tissue from hFLC-LB transplants expresses hepatocyte-specific antigen (HSA) but not AFP (left). Immunostaining for human CD31 and alpha-smooth muscle actin (SMA) shows the formation of major vessels inside the liver tissue (right). Bars, 100 μm.

Panels b, c, d, and e—Electronmicroscopic images of hFLC-LB derived liver tissues. Hepatocytes with tight junctions (panel b, panel c), bile canaliculi, abundant mitochondria and glycogen & lipid accumulations (panel d, panel e) are shown.

Figure 47A:
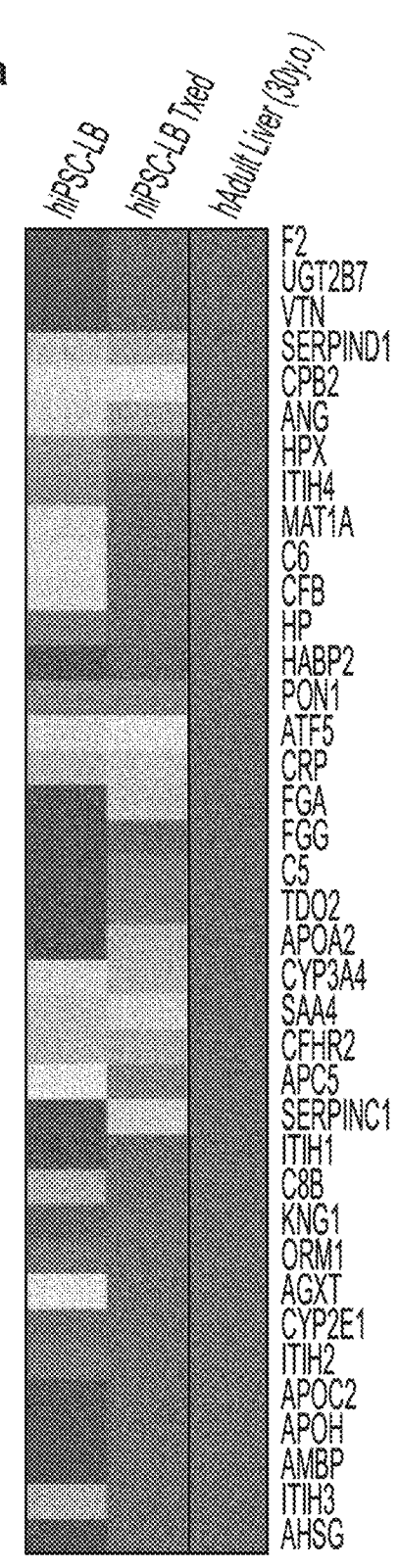
Figure 47B:
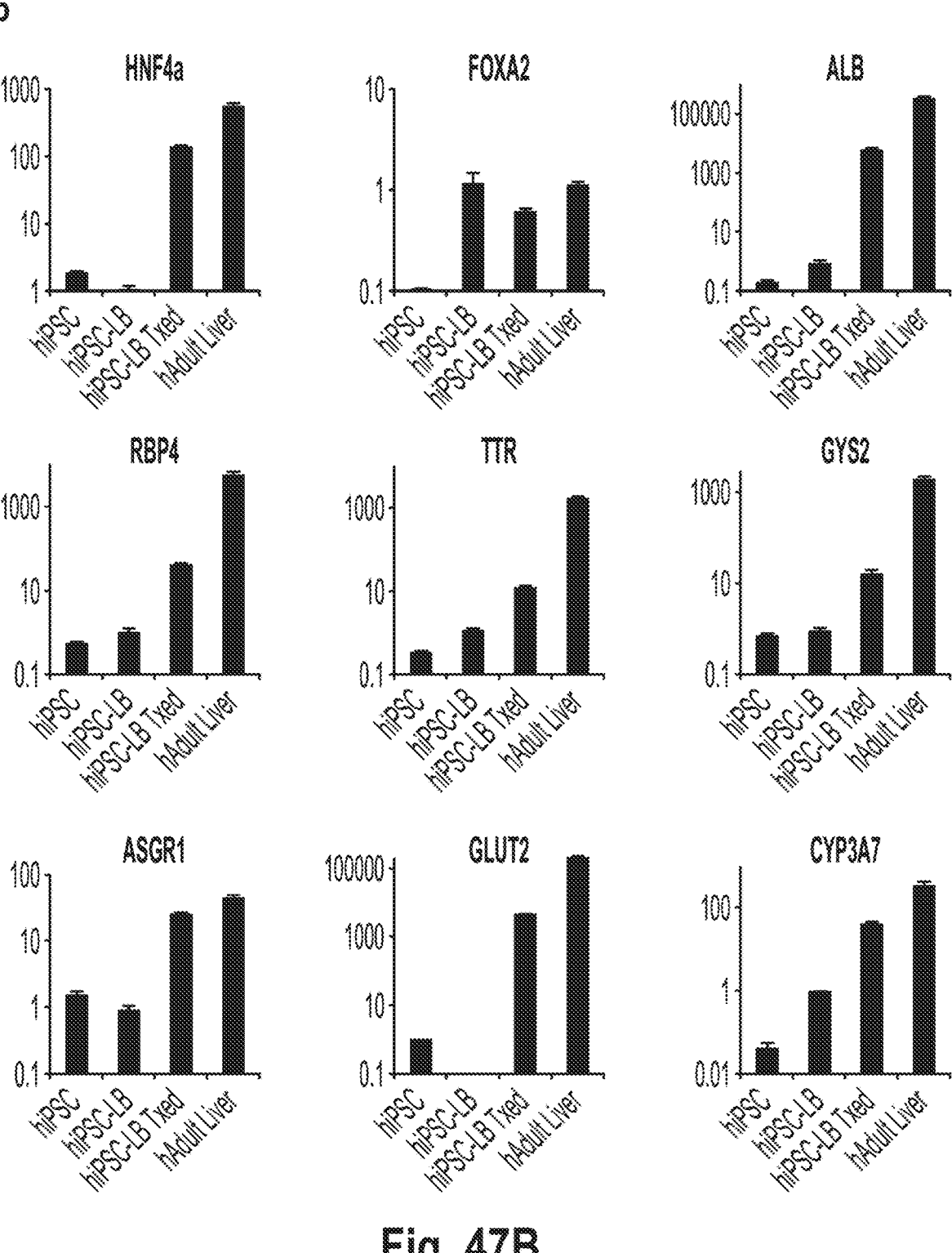

FIG. 47*a* and FIG. 47*b* Gene expression profile for hiPSC-LB transplants FIG. 47*a*—Microarray profiles and FIG. 47*b*—qPCR validations of multiple hepatic maturation marker genes at day 60 post-transplantation revealed that hiPSC-LBs mature into mature hepatocytes through transplantation.

Figure 48:
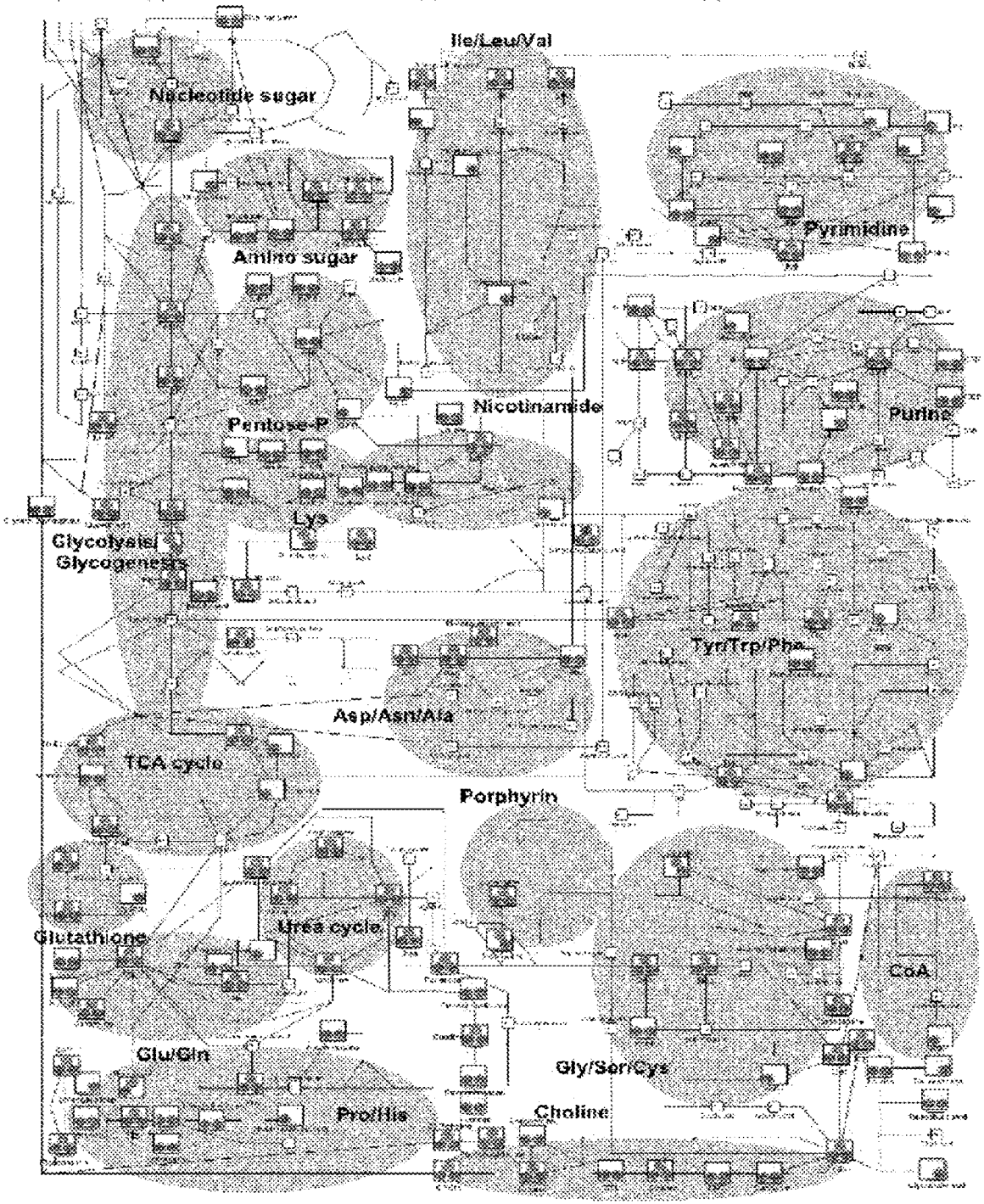

FIG. 48 Metabolic pathway maps of day 60 hiPSC-LB transplants (blue), human adult liver (red) and native hiPSCs (green).
Metabolites identified in the pathway map were indicated by different colored squares. N.D.: not detected.

Figure 49:
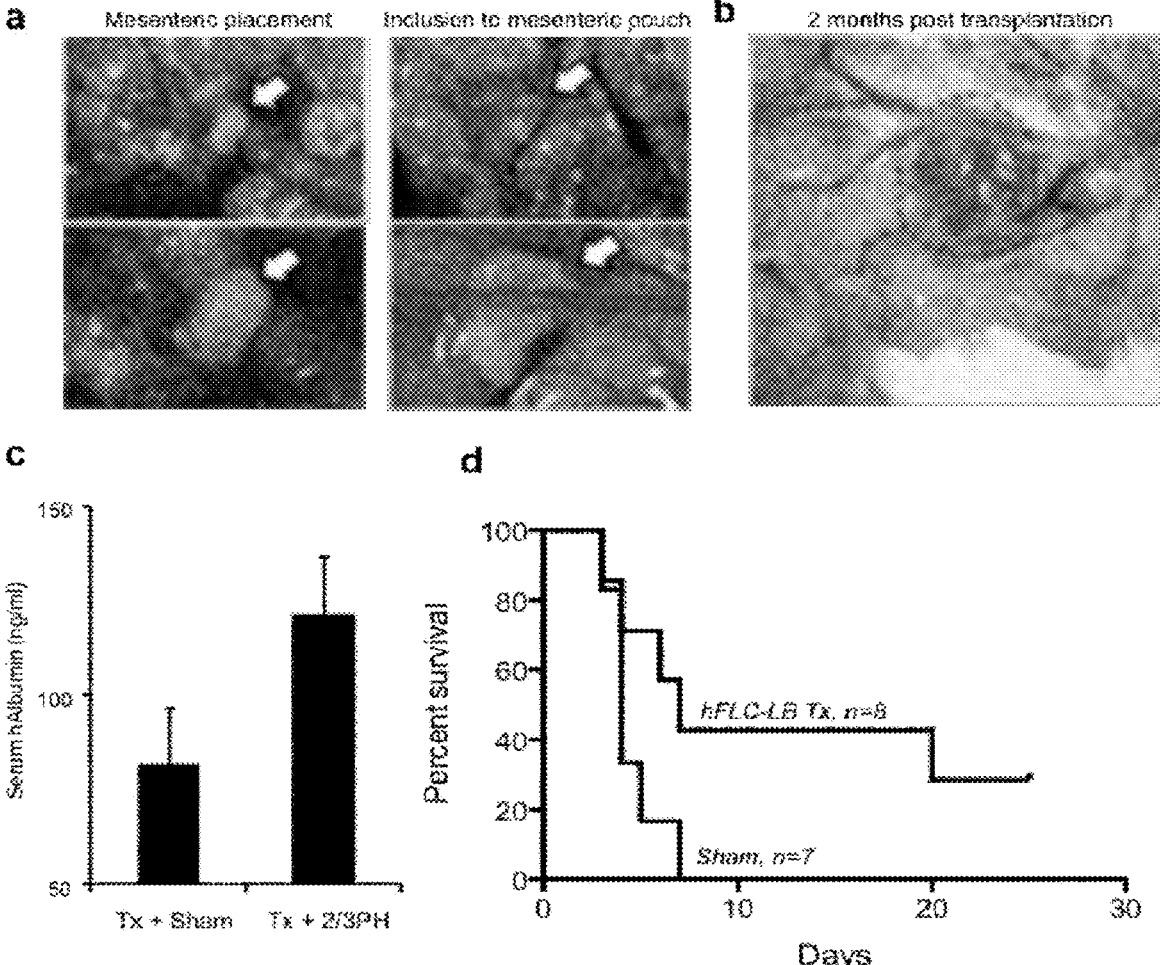

FIG. 49 Establishment of a mesenteric transplantation model towards therapeutic application.

Panel a—In vivo grown hiPSC- or FLC-derived LBs were transplanted onto the mesentery covered with fibrin glue.

Panel b—Macroscopic observation of the hiPSC-derived liver tissue at day 60 post-transplantation. Dotted area indicates the transplant.

Panel c—Production of human albumin increased at day 30 after hiPSC-LB transplantation by ⅔PH. (n=3)

Panel d-Kaplan-Meier survival curves of hFLC-LB transplanted group (n=8) and sham-operated group (n=7) in DT-infused Alb-TRECK/SCID mice.

BEST MODES FOR CARRYING OUT THE INVENTION

Hereinbelow, the present disclosure will be described in detail.

The present disclosure provides an organ bud prepared from vascular cells, mesenchymal cells and tissue or organ cells, wherein each of the vascular cell, the mesenchymal cell and the tissue or organ cell has been induced from pluripotent stem cells. Further, the method of preparing an organ bud of the present disclosure is characterized by culturing an organ cell together with at least one cell and/or factor selected from the group consisting of vascular endothelial cells, mesenchymal cells, factors secreted from vascular endothelial cells, factors secreted from mesenchymal cells, and factors secreted as a result of the presence of both vascular endothelial cells and mesenchymal cells.

In the present disclosure, the term "organ bud" means a structure capable of differentiating into an organ through maturing, the structure comprising three types of cells which are: i) vascular cells, mesenchymal cells and tissue or organ cells; or ii) organ cells, vascular endothelial cells and undifferentiated mesenchymal cells or cells differentiated therefrom. Whether a structure is an organ bud or not can be judged, for example, by transplanting the structure into an organism and examining whether or not it is capable of differentiating into an organ of interest (the structure can be judged as organ bud if it has differentiated into the organ of interest); and/or by examining whether or not the structure comprises all of the above-described three types of cells (the structure can be judged as organ bud if it comprises all of the three types of cells). The organ bud may be one which differentiates into an ectodermal organ such as brain, spinal cord, adrenal medulla, epidermis, hair/nail/dermal gland, sensory organ, peripheral nerve or lens; a mesodermal organ such as spleen, kidney, urinary duct, heart, blood, gonad, adrenal cortex, muscle, skeleton, dermis, connective tissue or mesothelium; or an endodermal organ such as liver, pancreas, digestive tract (pharynx, esophagus, stomach, intestinal tract), lung, thyroid, parathyroid, urinary tract or thymus. Preferably, the organ bud is one which differentiates into an endodermal organ; e.g., one which differentiates into liver (liver bud), one which differentiates into pancreas (pancreas bud), or one which differentiates into intestinal tract. Whether an organ bud is one which differentiates into an endodermal organ or not can be judged by examining the expression of marker proteins (if any one or a plurality of the marker proteins described later are expressed, the organ bud can be judged as the organ bud of interest). For example, HHEX, SOX2, HNF4A, AFP, ALB and the like are markers for liver buds; PDX1, SOX17, SOX9 and the like are markers for pancreas bud; and CDX2, SOX9 and the like are markers for organ buds which differentiate into intestinal tract. Among the terms used by those skilled in the art, the following are included in the organ bud of the present disclosure: liver bud, liver diverticula, liver organoid, pancreatic (dorsal or ventral) buds, pancreatic diverticula, pancreatic organoid, intestinal bud, intestinal diverticula, intestinal organoid (K. Matsumoto, et al. Science. 19; 294 (5542): 559-63 (2001)) and so on.

The organ bud of the present disclosure is prepared from vascular cells, mesenchymal cells and tissue or organ cells, all of these three types of cells being entirely derived from pluripotent stem cells.

As pluripotent cells, the following may be enumerated, for example: pluripotent cells obtained from organisms [e.g., ES cells, pluripotent cells induced by reprogramming such as iPS cells, MUSE cells (Multilineage-differentiating stress-enduring (Muse) cells are a primary source of induced pluripotent stem cells in human fibroblasts. PNAS, 2011), iMPC cells (induced multipotent progenitor cell; Mouse liver repopulation with hepatocytes generated from human fibroblasts. Nature, 2014)] and a combination thereof.

Pluripotent stem cells may be human-derived. Alternatively, pluripotent cells may also be derived from non-human animals (e.g., animals used as experimental animals, pet animals, working animals, race horses or fighting dogs; more specifically, mouse, rat, rabbit, pig, dog, monkey, cattle, horse, sheep, chicken, shark, devilfish, ratfish, salmon, shrimp, crab and the like).

The organ bud of the present disclosure may be prepared by co-culturing in vitro three types of cells (vascular cells, mesenchymal cells and tissue or organ cells) induced from pluripotent stem cells. The present disclosure provides a method of preparing an organ bud, comprising culturing vascular cells, mesenchymal cells and tissue or organ cells in vitro, wherein each of the vascular cell, the mesenchymal cell and the tissue or organ cell has been induced from pluripotent stem cells.

In the present disclosure, the term "tissue or organ cell" is a concept encompassing cells differentiated into functional cells constituting tissues or organs, or undifferentiated cells which are capable of differentiating into such functional cells. Undifferentiated cells include stem cells, progenitor cells, endoderm cells, organ bud cells, and so on. Preferably, undifferentiated cells are those cells which are destined to, but are yet to, differentiate into functional cells. Examples of "undifferentiated tissue or organ cell" include, but are not limited to, cells capable of differentiating into an organ such as kidney, heart, lung, spleen, esophagus, stomach, thyroid, parathyroid, thymus, gonad, brain or spinal cord; cells capable of differentiating into an ectodermal organ such as brain, spinal cord, adrenal medulla, epidermis, hair/nail/ dermal gland, sensory organ, peripheral nerve or lens; cells capable of differentiating into a mesodermal organ such as spleen, kidney, urinary duct, heart, blood, gonad, adrenal cortex, muscle, skeleton, dermis, connective tissue or mesothelium; and cells capable of differentiating into an endodermal organ such as liver, pancreas, digestive tract (pharynx, esophagus, stomach, intestinal tract), lung, thyroid, parathyroid, urinary tract or thymus. Whether or not a certain cell is capable of differentiating into an ectodermal organ, mesodermal organ or endodermal organ can be determined by checking for the expression of marker proteins (if any one or more of marker proteins are expressed, the cell can be judged as a cell capable of differentiating into an ectodermal organ, mesodermal organ or endodermal organ). For example, in cells capable of differentiating into liver, HHEX, SOX2, HNF4A, AFP, ALB and the like are markers; in cells capable of differentiating into pancreas, PDX1, SOX17, SOX9 and the like are markers; in cells capable of differentiating into intestinal tract, CDX2, SOX9 and the like are markers; in cells capable of differentiating into kidney, SIX2 and SALL1 are markers; in cells capable of differentiating into heart, NKX2-5, MYH6, ACTN2, MYL7 and HPPA are markers; in cells capable of differentiating into blood, C-KIT, SCA1, TER119 and HOXB4 are markers; and in cells capable of differentiating into brain or spinal cord, HNK1, AP2, NESTIN and the like are markers. Among the terms used by those skilled in the art, the following are included in the "undifferentiated tissue or organ cell" of the present disclosure: hepatoblast, hepatic progenitor cells, hepatic precursor cells, pancreatoblast, pancreatic progenitors, pancreatic progenitor cells, pancreatic precursor cells, endocrine precursors, intestinal progenitor cells, intestinal precursor cells, intermediate mesoderm, metanephric mesenchymal precursor cells, multipotent nephron progenitor, renal progenitor cells, cardiac mesoderm, cardiovascular progenitor cells, cardiac progenitor cells (J R. Spence, et al. Nature.; 470(7332): 105-9.(2011); Self, et al. EMBO J.; 25(21): 5214-5228.(2006); J. Zhang, et al. Circulation Research.; 104: e30-e41(2009); G. Lee, et al. Nature Biotechnology 25, 1468-1475 (2007)) and so on. Undifferentiated cells may be prepared from pluripotent stem cells such as induced pluripotent stem cells (iPS cells) or embryonic stem cells (ES cells) by known methods. For example, cells capable of differentiating into liver may be prepared as previously described (K. Si-Taiyeb, et al. Hepatology, 51 (1): 297-305(2010); T. Touboul, et al. Hepatology. 51 (5):1754-65 (2010)); cells capable of differentiating into pancreas may be prepared as previously described (D. Zhang, et al. Cell Res.; 19(4):429-38 (2009)); cells capable of differentiating into intestinal tract may be prepared as previously described (J. Cai, et al. J Mol Cell Biol.; 2(1): 50-60 (2010); R. Spence, et al. Nature.; 470 (7332):105-9 (2011)); cells capable of differentiating into heart may be prepared as previously described (J. Zhang, et al. Circulation Research.; 104: e30-e41(2009); and cells capable of differentiating into brain or spinal cord may be prepared as previously described (G. Lee, et al. Nature Biotechnology 25, 1468-1475 (2007)). Examples of functional cells constituting organs or tissues include, but are not limited to, endocrine cells of pancreas, pancreatic duct epithelial cells of pancreas, hepatocytes of liver, epithelial cells of intestinal tract, tubular epithelial cells of kidney, podocytes of kidney, cardiomyocytes of heart, lymphocytes and granulocytes of blood, erythrocytes, neurons and glial cells of brain, and neurons and Schwann cells of spinal cord.

In the preparation of the organ bud of the present disclosure, tissue or organ cells prepared (induced by directed differentiation) from pluripotent stem cells are used.

With respect to directed differentiation from pluripotent stem cells (e.g., iPS cells) into hepatic endoderm cells (iPSC-HE), hepatic function has been greatly improved by using day 7 TBX3 and ADR1AB co-positive cells based on comparison of differentiation stages (see Example described later).

In the present specification, expressions such as "positive" or "+" used with respect to cell surface markers refer to a state in which expression of the relevant cell surface marker on the cell can be confirmed by immunostaining or the like. On the other hand, expressions such as "negative" or "−" refer to a state in which expression of the relevant marker cannot be confirmed by immunostaining or the like.

TBX3 and ADR1AB co-positive hepatic endoderm cells (iPSC-HE) may be prepared according to the method described in Example provided later (Protocols 1 to 3 of FIG. 8A, and FIG. 13A).

According to Protocol 1 of FIG. 8A, pluripotent stem cells may be cultured in the presence of a ROCK inhibitor, a factor belonging to the transforming growth factor β family, a factor belonging to the Wnt family and a class I histone deacetylase (HDAC) inhibitor (which may not be added) (e.g., for 1 to 2 days) and then cultured in the presence of a factor belonging to the transforming growth factor β family, a factor belonging to the Wnt family and a class I histone deacetylase (HDAC) inhibitor (which may not be added) (e.g., for 1 to 2 days). Subsequently, cells obtained through a step of further culturing in the presence of a factor belonging to the transforming growth factor β family and a factor belonging to the Wnt family (e.g., for 0 to 3 days) (definitive endoderm) are cultured in the presence of an FGF and a factor belonging to the TGF-β superfamily (e.g., for 1 to 4 days) for directed differentiation into TBX3 and ADR1AB co-positive cells.

According to Protocol 2 of FIG. 8A, pluripotent stem cells may be cultured in the presence of a ROCK inhibitor (e.g., for 1 to 2 days) and then cultured in the presence of a β catenin activator, a PI3K inhibitor and a factor belonging to the transforming growth factor β family (e.g., for 1 to 2 days). Subsequently, cells obtained through a step of further culturing in the presence of a factor belonging to the transforming growth factor β family and a BMP inhibitor (e.g., for 2 to 4 days) (definitive endoderm) are cultured in the presence of an FGF and a factor belonging to the TGF-β superfamily (e.g., for 1 to 4 days) for directed differentiation into TBX3 and ADR1AB co-positive cells.

According to Protocol 3 of FIG. 8A, pluripotent stem cells may be cultured in the presence of a ROCK inhibitor (e.g., for 1 to 2 days) and then cultured in the presence of a factor belonging to the transforming growth factor β family (e.g., for 2 to 5 days). Cells obtained through the above step (definitive endoderm) are cultured in the presence of an FGF and a factor belonging to the TGF-β superfamily (e.g., for 1 to 4 days) for directed differentiation into TBX3 and ADR1AB co-positive cells.

According to the protocol of FIG. 13A, pluripotent stem cells may be cultured in the presence of a ROCK inhibitor, a factor belonging to the transforming growth factor β family, a β catenin activator and a class I histone deacetylase (HDAC) inhibitor (which may not be added) (e.g., for 1 to 2 days) and then cultured in the presence of a factor belonging to the transforming growth factor β family, a β catenin activator and a class I histone deacetylase (HDAC) inhibitor (which may not be added) (e.g., for 1 to 2 days). Subsequently, cells obtained through a step of further culturing in the presence of a factor belonging to the transforming growth factor β family (e.g., for 0 to 4 days) (definitive endoderm) are cultured in the presence of an FGF and a factor belonging to the TGF-β superfamily (e.g., for 1 to 4 days) for directed differentiation into TBX3 and ADR1AB co-positive cells.

An additional culture step may be included before or after each of the above-described culture steps of directed differentiation from pluripotent stem cells into TBX3 and ADR1AB co-positive cells.

In the present disclosure, the term "vascular cell" is a concept encompassing cells differentiated into blood-constituting cells or undifferentiated cells which are capable of differentiating into such cells. Undifferentiated cells include stem cells, progenitor cells, mesodermal cells, and the like. Preferably, undifferentiated cells are those cells which are destined to, but are yet to, differentiate into vascular cells. Examples of vascular cells include, but are not limited to, vascular endothelial cells, vascular endothelial progenitor cells, endocardial progenitor cells and angioblasts. Among them, vascular endothelial cells are preferable. Whether or not a certain cell is a vascular endothelial cell can be determined by checking for the expression of marker proteins such as TIE2, VEGFR-1, VEGFR-2, VEGFR-3 or CD41 (if any one or more of the above marker proteins are expressed, the cell can be judged as a vascular endothelial cell). Vascular endothelial cells used in the present disclosure may be either differentiated or undifferentiated. Whether or not a certain vascular endothelial cell is differentiated can be determined with CD31 and CD144. Among the terms used by those skilled in the art, the following are included in the vascular endothelial cell of the present disclosure: endothelial cells, umbilical vein endothelial cells, endothelial progenitor cells, endothelial precursor cells, vasculogenic progenitors, hemangioblast (H J. joo, et al. Blood. 25; 118(8): 2094-104 (2001)) and so on.

In the preparation of the organ bud of the present disclosure, vascular cells prepared (induced by direct differentiation) from pluripotent stem cells are used.

Directed differentiation from pluripotent stem cells (e.g., iPS cells) into vascular endothelial cells (iPSC-EC) may be performed as follows. Briefly, pluripotent stem cells are dissociated and seeded in the presence of Rho kinase, and then cultured in Medium 1 (DMEM/F12 medium supplemented with 1-2% B27, 1% Glutamax, 25 ng/ml BMP4 and 8 μM CHIR 99021) for 3 days and in Medium 2 (StemPro34-SFM supplemented with 200 ng/ml VEGF and 2 μM Forskolin) for 3 to 4 days. Alternatively, culture may be performed in Medium 3 (StemPro34-SFM supplemented with 50 ng/mL VEGF) for up to 7 days. The thus prepared vascular endothelial cells (iPSC-EC) are subjected to immunostaining or FACS for examining the expression of a vascular endothelial marker CD31 (PECAM1). They are suitable for use in the present disclosure if 90% or more of them are found to express CD31. Gene expression analyses revealed high-yield expression of vascular endothelial markers PECAM1, CDH5, KDR, CD34, etc., with a 10- to more than 100-fold increase as compared to their expressions in iPS cells before directed differentiation (see Example 3 described later). In addition to the expression of vascular endothelial marker CD31, expressions of CD144 and CD309 proteins can be confirmed by immunostaining (see Example 3 described later).

The present disclosure provides a method of preparing CD31 and CD144 co-positive cells, comprising culturing pluripotent stem cells in the presence of a ROCK inhibitor, a β catenin activator and a factor belonging to the TGF-β superfamily (e.g., for 1 to 2 days), then culturing the cells in the presence of a β catenin activator and a factor belonging to the TGF-β superfamily (e.g., for 2 to 3 days), and further culturing the cells in the presence of a vascular endothelial growth factor receptor (VEGFR) agonist and an adenylate cyclase activator (e.g., for 4 to 8 days) (Pr1 of FIG. 11A). The CD31 and CD144 co-positive cells may be iPSC-EC. The CD31 and CD144 co-positive cells may be used in the preparation of organ buds.

The present disclosure also provides a method of preparing CD31 and CD144 co-positive cells, comprising culturing pluripotent stem cells in the presence of a ROCK inhibitor, a VEGFR agonist, a factor belonging to the transforming growth factor β family, a β catenin activator and a factor belonging to the TGF-β superfamily (e.g., for 1 to 2 days), then culturing the cells in the presence of a VEGFR agonist, a factor belonging to the transforming growth factor β family, a β catenin activator and a factor belonging to the TGF-β superfamily (e.g., for 2 to 4 days)

and further culturing the cells in the presence of a VEGFR agonist and an inhibitor of TGF-β type I receptor (e.g., for 4 to 7 days) (Pr2 of FIG. 11A). The CD31 and CD144 co-positive cells may be iPSC-EC. The CD31 and CD144 co-positive cells may be used in the preparation of organ buds.

The present disclosure also provides a method of preparing CD31 and CD144 co-positive cells, comprising culturing pluripotent stem cells in the presence of a ROCK inhibitor and a factor belonging to the transforming growth factor β family (e.g., for 1 to 2 days), then culturing the cells in the presence of a factor belonging to the transforming growth factor β family (e.g., for 1 to 3 days), further culturing the cells in the presence of an FGF and a factor belonging to the TGF-superfamily (e.g., for 1 to 3 days), and subsequently culturing the cells in the presence of a VEGFR agonist (e.g., for 2 to 7 days) (Pr3 of FIG. 11A). The CD31 and CD144 co-positive cells may be iPSC-EC. The CD31 and CD144 co-positive cells may be used in the preparation of organ buds.

The present disclosure also provides a method of preparing CD31 and CD144 co-positive cells, comprising culturing pluripotent stem cells in the presence of a ROCK inhibitor and a factor belonging to the TGF-B superfamily (e.g., for 1 to 2 days), then culturing the cells in the presence of a factor belonging to the TGF-β superfamily (e.g., for 2 to 4 days), and further culturing the cells in the presence of a factor belonging to the TGF-β superfamily, a VEGFR agonist and an FGF (e.g., for 2 to 7 days) (Pr4 of FIG. 11A). The CD31 and CD144 co-positive cells may be iPSC-EC. The CD31 and CD144 co-positive cells may be used in the preparation of organ buds.

An additional culture step may be included before or after each of the above-described culture steps of directed differentiation from pluripotent stem cells into CD31 and CD144 co-positive cells.

Further, it is also possible to raise the positive ratio(s) for CD31 and/or CD144 by re-seeding the CD31 and CD144 co-positive cells and culturing them in an extension medium (Example 3 described later). The extension medium may be exchanged with one of a different type after lapse of a specific time period. As the extension medium to be used at the time of re-seeding, StemPro-34SFM supplemented with VEGF-A is preferable. As a medium with which this medium is to be exchanged, Miracell™ EC (Takara Bio) is preferable. However, extension medium is not limited to these media. Preferably, a ROCK inhibitor is added for 1 day at the time of re-seeding.

In the preparation of the organ bud of the present disclosure, vascular cells are preferably CD31 and CD144 co-positive. Further, the vascular cells are preferably such that at least one gene selected from the group consisting of PECAM1, CDH5, KDR and CD34 is expressed in a higher yield than in pluripotent stem cells that are yet to undergo directed differentiation.

In the present disclosure, the term "mesenchymal cell" is a concept that encompasses cells differentiated into connective tissue cells that are mainly located in mesoderm-derived connective tissues and which form support structures for cells that function in tissues or undifferentiated cells which are capable of differentiating into such cells. Examples of the undifferentiated cell include, but are not limited to, stem cells, progenitor cells and mesodermal cells. Undifferentiated cells are preferably those cells which are destined to, but are yet to, differentiate into mesenchymal cells. Mesenchymal cells used in the present disclosure may be either differentiated or undifferentiated. Whether a certain cell is an undifferentiated mesenchymal cell or not may be determined by checking for the expression of marker proteins such as Stro-1, CD29, CD44, CD73, CD90, CD105, CD133, CD271 or Nestin (if any one or more of the above-listed marker proteins are expressed, the cell can be judged as undifferentiated mesenchymal cell). A mesenchymal cell in which none of the above-listed markers are expressed can be judged as a differentiated mesenchymal cell. Among the terms used by those skilled in the art, the following are included in the mesenchymal cell of the present disclosure: Septum Mesenchyme, Septum Transversum Mesenchyme, mesenchymal stem cells, mesenchymal progenitor cells, mesenchymal cells (R. Peters, et al. PLOS One. 30; 5(12): e15689 (2010)) and so on.

In the preparation of the organ bud of the present disclosure, mesenchymal cells prepared (induced by directed differentiation) from pluripotent stem cells are used.

Directed differentiation of pluripotent stem cells (e.g., iPS cells) into mesenchymal cells (iPSC-MC) may be performed as follows. Briefly, pluripotent stem cells are dissociated and seeded in the presence of Rho kinase, and then cultured in Medium 1 (DMEM/F12 medium supplemented with 1-2% B27, 1% Glutamax, 8 µM CHIR 99021 and 25 ng/ml BMP4) for 3 days and in Medium 2 (DMEM/F12 medium supplemented with 1-2% B27, 1% Glutamax, 10 ng/ml PDGFBB and 2 ng/ml Activin A) for 2 days. The cells cultured further in Medium 3 (DMEM/F12 medium supplemented with 1-2% B27, 1% Glutamax, 10 ng/ml bFGF and 12 ng/mL BMP4) for 2 days may be used. Alternatively, the resultant cells may further be subjected to maintenance culture in a medium for mesenchymal cells (such as MSCGM). The thus prepared mesenchymal cell (iPSC-MC) may be a cell that is CD166 positive and which does not express a vascular endothelial marker CD31 (PECAM1).

The present disclosure also provides a method of preparing CD166 positive but CD31 negative cells, comprising culturing pluripotent stem cells in the presence of a ROCK inhibitor, a β catenin activator and a factor belonging to the TGF-β superfamily (e.g., for 1 to 2 days), then culturing the cells in the presence of a β catenin activator and a factor belonging to the TGF-β superfamily (e.g., for 3 to 5 days), culturing the cells in the presence of a PDGF receptor agonist and a factor belonging to the transforming growth factor β family (e.g., for 1 to 4 days), further culturing in the presence of an FGF and a factor belonging to the transforming growth factor β family (e.g., for 2 to 6 days), and subjecting the resultant cells to maintenance culture in a medium for mesenchymal cells (e.g., for 3 to 20 days). An additional culture step may be included before or after each of the above-described culture steps of directed differentiation from pluripotent stem cells into CD166 positive but CD31 negative cells. The CD166 positive but CD31 negative cells may be mesenchymal cells (iPSC-MC). The CD166 positive but CD31 negative cells may be used in the preparation of organ buds.

Specific examples of medium for mesenchymal cells include, but are not limited to, MSCGM.

In the preparation of the organ bud of the present disclosure, mesenchymal cells may be septum transversum mesenchyme (STM) cells. STM cells may be LHX2 and WT1 co-positive. Transcription of FOXF1, HLX1, COL4A and ALCAM is activated in STM cells, and the cells may be LHX2 positive, WT1 positive and MIIA positive.

The present disclosure also provides a method of preparing LHX2 and WT1 co-positive cells, comprising culturing pluripotent stem cells in the presence of a ROCK inhibitor, a β catenin activator and a factor belonging to the TGF-β superfamily (e.g., for 1 to 2 days), then culturing the cells in the presence of a β catenin activator and a factor belonging to the TGF-β superfamily (e.g., for 3 to 5 days), further culturing the cells in the presence of a PDGF receptor agonist and a factor belonging to the transforming growth factor β family (e.g., 1 to 4 days), and culturing the cells in the presence of an FGF and a factor belonging to the transforming growth factor β family (e.g., for 2 to 6 days). An additional culture step may be included before or after each of the above-described culture steps of directed differentiation from pluripotent stem cells into LHX2 and WT1 co-positive cells. The LHX2 and WT1 co-positive cells may be septum transversum mesenchyme (STM) cells. The LHX2 and WT1 co-positive cells may be used in the preparation of organ buds.

Hereinbelow, factors which may be used in the above-described method of directed differentiation from pluripotent stem cells into three types of cells (organ cells, vascular cells and mesenchymal cells) will be described.

As ROCK inhibitors, Y-27632, GSK429286A, SR3677, Ripasudil (K-115), Fasudil, Thiazovivin or the like may be enumerated. Among them, Y-27632 is preferable.

As factors belonging to the transforming growth factor β family, Activin A, Nodal or the like may be enumerated. Among them, Activin A is preferable.

As factors belonging to the Wnt family, Wnt3a, Wnt3a-AFM, CHIR99021, R-Spondin-1, BIO (6-bromoindirubin-3'-oxime) or the like may be enumerated. Among them, Wnt3a is preferable. The factor belonging to the Wnt family may be one which is capable of activating β catenin.

As class I histone deacetylase (HDAC) inhibitors, butyrates (such as sodium butyrate), Valproic Acid, Panobinosta (LBH589), Apicidin, BML-210, Depudecin, HC Toxin, M344, Oxamflatin, Scriptaid, Splitomicin, Suberoyl bis-hydroxamic acid, Trichostatin A, Vorinostat (SAHA, MK0683), Entinostat (MS-275), Panobinostat (LBH589), Mocetinostat (MGCD0103), Biphenyl-4-sulfonyl chloride, ACY-738, Belinostat (PXD101), Romidepsin (FK228, Depsipeptide), MC1568, Tubastatin A, Givinostat (ITF2357), Dacinostat (LAQ824), CUDC-101, Quisinostat (JNJ-26481585), Pracinostat (SB939), PCI-34051, Droxinostat, Abexinostat (PCI-24781), RGFP966, AR-42, Rocilinostat (ACY-1215), Tacedinaline (CI994), CUDC-907, Curcumin, Tubacin, RG2833 (RGFP109), Resminostat, Divalproex Sodium, Sodium Phenylbutyrate, Tubastatin A, TMP269, Santacruzamate A (CAY10683), TMP195, Tasquinimod, BRD73954, Citarinostat (ACY-241), HPOB, LMK-235, Nexturastat A, Tucidinostat (Chidamide), (−)-Parthenolide, CAY10603, 4SC-202, BG45, ITSA-1 (ITSA1) or the like may be enumerated. Among them, sodium butyrate is preferable.

As FGF (fibroblast growth factor), basic FGF (also expressed as bFGF or FGF2), FGF4, FGFC (chimeric fibroblast growth factor) or the like may be enumerated. Among them, basic FGF is preferable.

As factors belonging to the TGF-B superfamily, BMP4, BMP2, BMP or the like may be enumerated. Among them, BMP4 is preferable.

As β catenin activators, CHIR99021, Wnt3a, Wnt3a-AFM, R-Spondin-1, BIO (6-bromoindirubin-3'-oxime) or the like may be enumerated. Among them, CHIR99021 is preferable. CHIR99021 can be an alternative for Wnt3a in the directed differentiation from iPSC into DE (Example 2 described later; CHIR d3 of FIG. 13A).

As PI3K inhibitors, PI-103, ZSTK474, NVP-BEZ235, LY294002, Wortmannin or the like may be enumerated.

Among them, PI-103 is preferable. PI3K inhibitor may be PI3K, Akt and mTOR inhibitor.

As BMP inhibitors, LDN-193189, Galunisertib (LY2157299), LY2109761, SB525334, SB505124, Pirfenidone, GW788388, LY364947, RepSox, K02288, SD-208, LDN-214117, SIS3 HCl, Vactosertib (TEW-7197), DMH1, LDN-212854, ML347, Kartogenin, Hesperetin, Alantolactone or the like may be enumerated. Among them, LDN-193189 is preferable. BMP inhibitor may be an ALK2 and ALK3 inhibitor.

As vascular endothelial growth factor receptor (VEGFR) agonists, VEGF, VEGF-A, VEGF-B, VEGF-C, VEGF-D, VEGF-E, PIGF or the like may be enumerated. Among them, VEGF is preferable.

As adenylate cyclase activators, Forskolin, HJC0350, 8-Br-CAMP, Adenosine 3',5'-cyclic monophosphate (cAMP), Dibutyryl-cAMP (Bucladesine) or the like may be enumerated. Among them, Forskolin is preferable. Adenylate cyclase activator may be one that increases intracellular cAMP levels.

As inhibitors of TGF-β type I receptor, SB431542, LDN-193189, Galunisertib (LY2157299), LY2109761, SB525334, SB505124, GW788388, LY364947, RepSox, LDN-193189, K02288, LDN-214117, SD-208, Vactosertib (TEW-7197), ML347, LDN-212854, DMH1, Pirfenidone, Alantolactone, SIS3, Hesperetin or the like may be enumerated. Among them, SB431542 is preferable. Inhibitor of TGF-B type I receptor may be an ALK4, ALK5 and ALK7 inhibitor and an activin inhibitor as well.

As PDGF receptor agonists, PDGFBB, PDGF-AA, PDGF-AB, PDGF-CC, PDGF-DD or the like may be enumerated. Among them, PDGFBB is preferable.

Culture ratios of the three cell types in coculture are not particularly limited as long as the ratio enables the formation of organ buds. A preferable cell count ratio is as follows. Tissue or organ cell:vascular endothelial cell:mesenchymal cell=10:10-5:2-1.

Either one or both of vascular endothelial cell and mesenchymal cell may be substituted by substances such as factors secreted by vascular endothelial cells, factors secreted by mesenchymal cells, factors secreted as a result of the presence of both vascular endothelial cells and mesenchymal cells, and so forth.

Examples of the substances such as factors secreted by vascular endothelial cells, factors secreted by mesenchymal cells, factors secreted as a result of the presence of both vascular endothelial cells and mesenchymal cells, and so forth include, but are not limited to, FGF2, FGF5, BMF4, BMP6 and CTGF.

With respect to the amount of addition of these substances, FGF2 may be added at 10-100 ng/ml, preferably at about 20 ng/ml, per $1 \times 10^6$ cells; and BMF4 may be added at 10-100 ng/ml, preferably at about 20 ng/ml, per $1 \times 10^6$ cells.

The medium used for culturing is not particularly limited. Any medium may be used as long as it enables the formation of organ buds. Preferably, a medium for culturing vascular cells (e.g., vascular endothelial cells), a medium for culturing tissue or organ cells or a mixture of these two media may be used. As a medium for culturing vascular endothelial cells, any medium may be used but, preferably, a medium containing at least one of the following substances may be used: hEGF (recombinant human epidermal growth factor), VEGF (vascular endothelial growth factor), hydrocortisone, bFGF, ascorbic acid, IGF1, FBS, antibiotics (e.g., gentamycin or amphotericin B), heparin, L-glutamine, phenol red and BBE. Specific examples of this medium which may be used in the present disclosure include, but are not limited to, EGM-2 BulletKit (Lonza), EGM BulletKit (Lonza), Vascu-Life EnGS Comp Kit (LCT), Human Endothelial-SFM Basal Growth Medium (Invitrogen) and human microvascular endothelial cell growth medium (TOYOBO). As a medium for culturing tissue or organ cells, any medium may be used but, when the organ cell is hepatocyte, a medium containing at least one of the following substances may be preferably used: ascorbic acid, BSA-FAF, insulin, hydrocortisone and GA-1000. As a medium for culturing hepatocyte, HCM BulletKit (Lonza) from which hEGF (recombinant human epidermal growth factor) has been removed and RPMI1640 (Sigma-Aldrich) to which 1% B27 Supplements (GIBCO) and 10 ng/ml hHGF (Sigma-Aldrich) have been added may typically be used. With respect to formation of human liver buds, use of a medium prepared as described below has been found effective for maturation of liver buds. Briefly, GM BulletKit (Lonza) and HCM BulletKit (Lonza) from each of which hEGF has been removed are mixed at 1:1 and to the resultant mixture, dexamethasone, oncostatin M and HGF are added.

Preferably, organ cells are plated on a gel and cultured. The gel used for this purpose is not particularly limited. For example, BD Matrigel (BD Pharmingen) may be used.

The temperature at the time of culture is not particularly limited. The temperature is preferably 30-40° C., more preferably 37° C.

Although scaffold materials need not be used for culturing cells, a mixture of three types of cells may advantageously be cultured on a gel-like support that allows mesenchymal cells to contract.

Contraction of mesenchymal cells may be confirmed, for example, by noting the formation of a 3D tissue morphologically (either under microscope or with the naked eye) or by showing that the tissue is strong enough to retain its shape as it is collected with a spatula or the like (Takebe et al. Nature 499 (7459), 481-484, 2013).

The support may advantageously be a gel-like substrate having an appropriate stiffness [e.g., a Young's modulus of 200 kPa of less (in the case of a Matrigel-coated gel of a flat shape); however, the appropriate stiffness of the support may vary depending on the coating and shape]. Examples of such substrates include, but are not limited to, hydrogels (such as acrylamide gel, gelatin and Matrigel). The stiffness of the support need not be uniform and may vary with the shape, size and quantity of a cell condensate of interest so that it can be provided with a spatial/temporal gradient or can be patterned. In the case where the stiffness of the support is uniform, it is preferably 100 kPa or less, more preferably 1-50 kPa. The gel-like support may be planar, or alternatively, the side on which culture is to be performed may have a U- or V-shaped cross section. If the side of the gel-like support on which culture is to be performed has a U- or V-shaped cross section, cells tend to gather on the culture surface and a cell condensate can advantageously be formed from a smaller number of cells and/or tissues. Moreover, the support may be modified chemically or physically. Examples of modifying substances include, but are not limited to, Matrigel, laminin, entactin, collagen, fibronectin and vitronectin.

One example of the gel-like culture support that is provided with a spatial gradient of stiffness is a gel-like culture support that is stiffer in the central part than in the peripheral part. The stiffness of the central part is appropriately 200 kPa or less and it suffices that the peripheral part is softer than the central part. Appropriate values for the stiffness of the central and peripheral parts of the substrate are variable with the coating and the shape. Another example of the gel-like culture support that is provided with a spatial gradient of stiffness is a gel-like culture support that is stiffer in the peripheral part than in the central part.

One example of the patterned, gel-like culture support is a gel-like culture support having one or more patterns in which the central part is stiffer than the peripheral part. The stiffness of the central part is appropriately, 200 kPa or less and it suffices that the peripheral part is softer than the central part. Appropriate values for the stiffness of the central and peripheral parts of the substrate are variable with the coating and the shape. Another example of the patterned, gel-like culture support is a gel-like culture support having one or more patterns in which the peripheral part is stiffer than the central part. The stiffness of the peripheral part is appropriately 200 kPa or less and it suffices that the central part is softer than the peripheral part. Appropriate values for the stiffness of the central and peripheral parts of the substrate are variable with the coating and the shape.

The temperature during culture is not particularly limited but it is preferably 30-40° C. and more preferably 37° C.

The culture period is not particularly limited but it is preferably 3-10 days and more preferably 6 days.

In the present disclosure, the three types of cell species used for organ bud preparation are entirely derived from pluripotent stem cells, whereby the differentiation stages of the three types of cell species can be synchronized. By preparing organ buds from these cells, it is possible to improve the function of organ buds. Further, it becomes possible to reduce the costs and labor required for quality evaluation or production of the three types of cell species.

The organ bud of the present disclosure may be transplanted into a non-human animal, in which it is allowed to mature, whereby a tissue or organ can be prepared. Briefly, the present disclosure also provides a method of preparing a tissue or an organ, comprising transplanting the above-described organ bud into a non-human animal and differentiating the organ bud into a tissue or an organ. Examples of the non-human animal that may be used include animals that are used, for example, as experimental animals, pet animals, working animals, race horses or fighting dogs, more specifically, mouse, rat, rabbit, pig, dog, monkey, cattle, horse, sheep, chicken, shark, devilfish, ratfish, salmon, shrimp, crab and the like. Moreover, the non-human animal to be used herein is preferably an immunodeficient animal in order to avoid immunorejection.

Therefore, the present disclosure also provides a method of transplanting an organ bud, comprising transplanting the above-described organ bud prepared by the above-described method into a human or a non-human animal. The site of transplantation of the organ bud may be any site as long as transplantation is possible. Specific examples of the transplantation site include, but are not limited to, the intracranial space, the mesentery, the liver, the spleen, the kidney, the kidney subcapsular space, and the supraportal space. For intracranial transplantation, about 1 to 3 organ buds of 5 mm in size, prepared in vitro, may be transplanted. For intramesenteric transplantation, about 1 to 6 organ buds of 5 mm in size, prepared in vitro, may be transplanted. For transplantation into the supraportal space, about 1 to 20 organ buds of 5 mm in size, prepared in vitro, may be transplanted. For transplantation into the kidney subcapsular space, about 1 to 5 organ buds of 5 mm in size, prepared in vitro, may be transplanted. For transplantation into the liver, spleen or kidney, about 100 to 200 organ buds of 100 μm in size, prepared in vitro, may be transplanted.

The thus prepared tissue or organ may be used in drug discovery screening or regenerative medicine.

Therefore, the present disclosure provides a method of regeneration or function recovery of a tissue or an organ, comprising transplanting the above-described organ bud into a human or a non-human animal and differentiating the organ bud into a tissue or an organ. As non-human animals, animals used for such purposes as experimental animal, pet animal, working animal, race horse or fighting dog, more specifically, mouse, rat, rabbit, pig, dog, monkey, cattle, horse, sheep, chicken, shark, devilfish, ratfish, salmon, shrimp, crab or the like may be used.

The organ bud of the present disclosure may be formulated and used in the form of a composition for regenerative medicine. This composition of the present disclosure may be transplanted into a living body to prepare a tissue or an organ. Regeneration or function recovery of a tissue or an organ is also possible by transplanting the composition of the present disclosure into a living body.

Upon transplantation of the composition of the present disclosure into a living body, the organ bud may differentiate into a tissue or an organ with vascular networks. In such vascular networks, blood perfusion may occur. It is believed that the occurrence of blood perfusion in vascular networks enables generation of a tissue or an organ with a highly ordered tissue structure equivalent or close to the tissue structure of adult tissues.

The composition of the present disclosure may comprise a tissue vascularization promoter such as FGF2, HGF or VEGF, a gelatin sponge for hemostasis to cope with the bleeding from transplantation (product name: Spongel; Astellas Pharma), and a tissue adhesive for fixing transplants such as Bolheal (Teijin Pharma), Beriplast™ (CSL Behring) or TachoComb™ (CSL Behring).

The present disclosure also provides a method of preparing a non-human chimeric animal, comprising transplanting the above-described organ bud into a non-human animal and differentiating the organ bud into a tissue or an organ. The non-human animal (e.g., mouse) transplanted with the organ bud may mimic the physiological function of the organismal species (e.g., human) from which the tissue or organ cell used for preparing the organ bud is derived. In an Example to be described later, it was confirmed that mice into which organ buds prepared from human-derived iPS cells had been transplanted mimicked human liver function. Therefore, it is held possible to predict human drug metabolism profiles using those mice.

Still further, the present disclosure provides a method of evaluating a drug, comprising using at least one member selected from the group consisting of the organ bud, the tissue or organ and the non-human chimeric animal as prepared by the above-described methods, respectively. Specific examples of drug evaluation include, but are not limited to, evaluation of drug metabolism (e.g., prediction of drug metabolism profiles), evaluation of drug efficacy (e.g., screening for drugs that are effective as pharmaceuticals), toxicity evaluation, and evaluation of drug interactions.

Evaluation of drug metabolism may be performed as follows. Briefly, at least one member selected from the group consisting of the organ bud, the tissue or organ and the non-human chimeric animal as prepared by the above-described methods, respectively, is administered with a candidate compound for pharmaceuticals and the resulting biological sample is then collected and analyzed, whereby a human-type drug metabolism profile can be obtained. As a result, prediction of the distribution/metabolism/excretion processes of pharmaceuticals in human (which was extremely difficult to achieve by conventional methods)

becomes possible and it is expected that the development of safe and efficacious pharmaceuticals can be greatly accelerated.

Screening for drugs that are effective as pharmaceuticals may be performed as follows. Briefly, at least one member selected from the group consisting of the organ bud, the tissue or organ and the non-human chimeric animal as prepared from a cell established from a diseased patient by the above-described methods, respectively, is administered with a novel candidate compound for pharmaceuticals. This enables subsequent analysis. As a result, a potential is expected for achieving great improvement in the precision of drug efficacy prediction for the case of actual administration to human, which has been unsatisfactory in conventional in vitro tests.

Evaluation of toxicity may be performed as follows. Briefly, at least one member selected from the group consisting of the organ bud, the tissue or organ and the non-human chimeric animal as prepared by the above-described methods, respectively, is administered with a test substance and, thereafter, histological damage markers or the like are measured. This makes it possible to improve the precision of damage prediction.

Evaluation of drug interactions may be performed as follows. Briefly, at least one member selected from the group consisting of the organ bud, the tissue or organ and the non-human chimeric animal as prepared by the above-described methods, respectively, is administered with a plurality of drugs; then, each drug is examined for its pharmacokinetics such as distribution/metabolism/excretion processes, evaluated for its toxicity, and evaluated for its efficacy.

Further, it is also possible to create tissue stem cells from the tissue or organ prepared by the method of the present disclosure. Thus, the present disclosure is applicable to cell engineering techniques for large scale creation of human tissue cells and organ cells.

EXAMPLES

Hereinbelow, the present disclosure will be described in more detail with reference to the following Examples.

Example 1

Establishment of Massive Production Technique for Liver Buds from Human Pluripotent Stem Cells

Summary

Organoid transplantation therapy may potentially become a revolutionary therapeutic paradigm but securing reproducibility and scalability has been a major challenge. In this study, the present inventors attempted to solve this problem by constructing a scalable production platform for organ buds entirely from human induced pluripotent stem cells (iPSC). First, by conducting massive "reverse" screen experiments, the present inventors identified three progenitor populations (hepatic endoderm, endothelium and septum transversum mesenchyme) that can effectively generate liver buds in a highly reproducible manner. Furthermore, the present inventors achieved the level of scalability required for transplantation therapy by developing an omni-well-array culture platform for mass producing homogeneous and miniaturized liver buds on a $>10^8$ scale. Liver tissues which were generated entirely from iPSCs, vascularized and yet functional significantly improved subsequent hepatic functionalization to be potentiated by interactions of progenitors at gradual developmental stages. Further, this liver tissue enabled functional rescue to be achieved for acute liver failure via transplantation. Overall, this study provides a manufacturing platform for supplying multicellular liver bud organoids, which is expected to greatly facilitate clinical and pharmaceutical applications for the treatment of liver diseases.

Introduction

"Organoid technology" is a recently evolving approach for the treatment of intractable diseases as well as human development and disease models (Huch and Koo, 2015, Lancaster and Knoblich, 2014, Sasai, 2013). Based on a self-condensation principle, the present inventors have recently succeeded in building an additional complexity into organoids by developing multicellular organ buds (such as liver bud, pancreatic bud, and kidney bud) with therapeutic potential in various mouse disease models (Takebe et al., 2013, Takebe et al., 2014, Takebe et al., 2015). Nevertheless, given the purpose of generating sufficiently large and stable organoids for transplantation and drug testing in humans, broader applications of organoid-based approaches are subject to scalability and reproducibility challenges (Ding and Cowan, 2013). To facilitate the future therapeutic application of organ-bud-based approaches, the present inventors aimed at establishing a comprehensive, scalable, and reproducible method for generating vascularized human liver buds (LBs) entirely from feeder-free human induced pluripotent stem cells (iPSCs) and validating their functional capacity for transplant application.

Results

Figure 1:
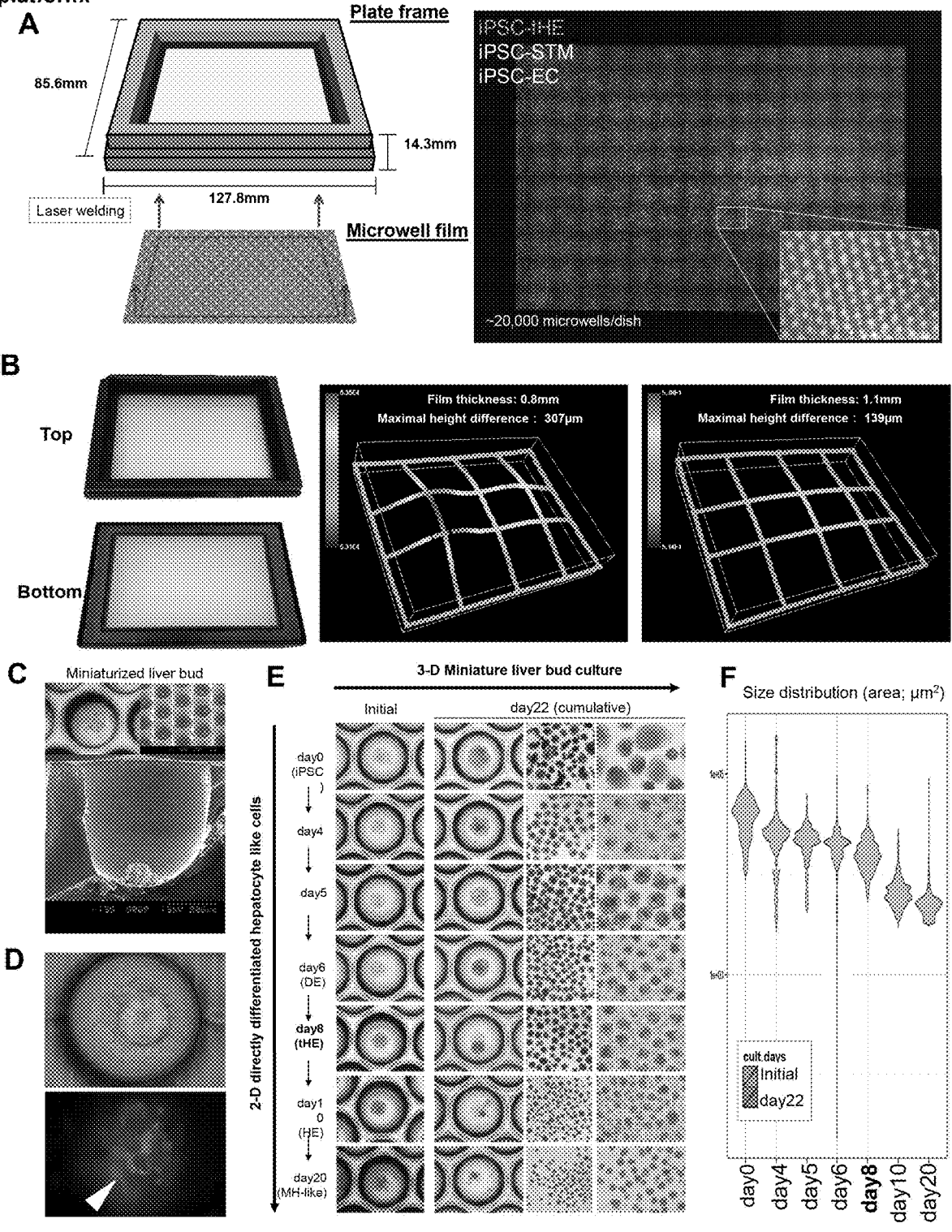
FIG. 1 Scalable liver bud production and differentiation by developing an omni-well-array platform.

The present inventors first aimed at establishing a scalable three-dimensional (3D) organoid culture platform with liver bud (LB) as an example. The overall strategy is summarized in FIG. 1A and FIG. 1B. Briefly, the present inventors developed a U-bottom-shaped microwell plate by combinatorial chemistry techniques to develop a finely structured film by transfer of a mold structure accurately onto a resin. The microwell array of the present inventors has an extremely high aspect ratio (the aperture diameter of each dimple is ~500 μm and the depth is 400 μm, and the dimples were tightly and triangularly arranged at an interval of 30 μm, as shown in FIG. 1C). It is difficult to broadly transfer such an aspect ratio with a conventional molding machine. Therefore, the present inventors improved the transfer accuracy by employing an internally optimized molding machine (see Experimental Procedures). As a result, prototyping has proven to be successful with 24-well and 6-well formats (Elplasia R B [round bottom]; 600 spots per well in 24 wells and 3,000 spots per well in 6 wells). The present inventors then adapted these plates into LB culture by mixing the human-iPSC-derived hepatic endoderm (iPSC-HE), human umbilical cord vein endothelial cells (HUVECs), and bone marrow mesenchymal stem cells (BMSCs) as previously described (Takebe et al., 2013). Upon optimization of coating material (FIG. 5 (Fig. S1)), dimple shape (data not shown), mixture ratio (FIG. 6A-6C (Figure S2A-S2C)) and cell count (FIG. 6D-6F (Figure S2D-S2F)), miniaturized LBs can be effectively formed using the microwell-array-based approach (see Supplementary Text).

To intensively scale up this strategy, the present inventors have devised an omni (1: one)-well-array plate containing over 20,000 microspots per well (FIG. 7A (Figure S3A)).

External dimensions of the frame (length, width, and height) of the omni-well-array plate meet the Society for Biomolecular Screening (SBS) standards as with common microplates. The plate was composed of two modules, a bottomless plate frame and a microwell transferred film, which were assembled by laser welding (FIG. 1A, left). The adaptation of microwell-transferred film used in 24-well/6-well formats was ineffective for the omni-well format, because the significant depression in the central portion led to abnormal organoid displacement and subsequent fusion (FIG. 1B (FIG. 1B), middle). Thus, the present inventors attempted to improve the flatness by (1) reducing the residual stress of the film and (2) enhancing the rigidity of the film. First, the present inventors minimized the molding pressure for transfer of patterns to lower the limit of mold transfer by optimizing the molding parameters, including mold temperature and pressing time, and by improving film deflection during laser welding. Second, the present inventors enhanced rigidity by thickening the film (FIG. 1B (FIG. 1B), caption). Among the various thickness conditions tested within a range of 0.8-1.4 mm, the present inventors found that 1.1 mm film thickness satisfied an acceptable rigidity without disturbing microscopic observation. The 3D profilometer demonstrated minimal height fluctuation under the improved conditions, enabling subsequent LB culture on a larger scale (FIG. 1B (FIG. 1B), right). Importantly, over 99% of the generated LBs were successfully collected by simple manual pipetting (FIG. 5B (Figure S1B)). Once the triple progenitors were seeded onto the omni-well plate, over 20,000 endothelialized LBs were self-organized, whereas LBs in single iPSC-HE culture were not self-organized (FIG. 1C, ID (FIGS. 1C and 1D)). Quality verification analysis by qRT-PCR showed that LBs in the omni-well were comparable in property to those in 24-well/6-well formats (FIG. 7B (Figure S3B)). In conclusion, the present inventors successfully developed a prototypal design of an omni-well-array plate for massive organoid production.

Next, the present inventors attempted to define the phenotype of an optimal endoderm cell population for LB generation in humans. For this purpose, the present inventors performed massive "reverse" screen experiments by comparing the multiple endoderm stages based on the quality of resultant organoids. Following the selection of the most reproducible mature hepatocyte differentiation protocols previously described (FIG. 8A-F (Figures S4A-S4F; Supplemental Experimental Procedures) (Kajiwara et al., 2012, Loh et al., 2014, Si-Tayeb et al., 2010), the present inventors further attempted to precisely determine the best endoderm stages for iPSC-LB functionality by starting LB culture from day 0 to day 20 cells (FIG. 9 (Figures S5) and FIGS. 2A and 2B (FIGS. 2A and 2B)). First, fluorescence-based quantitative assessment of the morphologic variation of the collected LBs generated from multiple stages (days 0-20) revealed that day 8 cells were the only population capable of maintaining highly homogeneous LBs within 100-200 μm in size (FIGS. 1E and 1F (FIGS. 1E and 1F). Subsequent qRT-PCR of hepatic marker genes (FIG. 9A (Figure S5A) and ELISA (FIG. 2A (FIG. 2A)) of protein production showed that day 8 cell-derived iPSC-LBs were higher in quality than day 0 (iPSC), 5, 6, 7, 10 and 20 cell-derived LB culture. Transcriptome analysis showed that the expression signatures of LBs were more similar to human adult liver tissues than 2D differentiated cells (FIG. 9 (Figure S5B)). Consistently, according to principal component analysis of overall gene expression, the PCI axis demonstrated that the profiles of day 8 buds were closer to those of human adult liver tissue samples, compared to other stage buds (FIG. 2B (FIG. 2B)). Interestingly, a remarkable enrichment in angiogenesis hallmark gene set was observed in day 8 buds, but not in day 7 buds (FIG. 9C (Figure S5C)), which possibly contributes to favorable in vivo vascularization outcomes.

To further characterize this "reversely" identified day 8 population, the present inventors performed SOX17/HNF4A co-immunostaining-, qRT-PCR-, fluorescence-activated cell sorting (FACS)- and Cerberus1-ELISA-based profiling and identified that day 8 cells represent a transitional population from definitive endoderm to hepatic endoderm (HE) cells (FIG. 8G (Figure S4G) and FIG. 2C (FIG. 2C)). Herein, the day 8 cells are defined as transitional hepatic endoderm (tHE) cells. Although being negative for definitive endoderm (DE) makers, day 8 cells do not express an HE marker such as HNF4A (FIG. 2C (FIG. 2C)), so the present inventors attempted to define the cells by identifying definable markers by comparative transcriptome analysis between day 6 and day 8 populations. Volcano plot analysis (comparing iPSC-DE and iPSC-tHE) identified T-box transcription factor 3 (TBX3) and adrenoceptor alpha 1B (ADRAIB) based on transcriptome dynamics (FIG. 2D (FIG. 2D) and FIG. 10 (Figure S6)), which was confirmed by immunostaining and qRT-PCR (FIG. 2E (FIG. 2E) and FIG. 3A (FIG. 3A)). Together although the developmental relevance of this reversely identified population remains elusive, the present inventors concluded that TBX3- and ADRAIB-co-positive tHE cells are the most effective stage for LB generation.

With respect to future applications of this LB-based approach, one major obstacle is the use of postnatal-tissue-derived stromal progenitors (i.e., HUVECs and BMSCs). Accordingly, the present inventors aimed at deriving two LB stromal progenitors from human iPSCs. During early liver organogenesis, HE cells migrate toward LIM homeobox 2 (LHX2)- and Wilms tumor 1 (WT1)-positive septum transversum mesenchyme (STM) to form LBs (Delgado et al., 2014, Kolterud et al., 2004). STM is involved not only in LB formation but also in the growth and survival of hepatoblasts mediated at least by STM-derived paracrine factors (Zaret, 2002). However, differentiation protocols for STM cells have not been developed (Iyer et al., 2015, Witty et al., 2014). In order to direct STM fate, the present inventors exposed potential inducers and their combinations in iPSC-derived lateral plate mesoderm (iPSC-Meso) at day 4. The transcriptional activation of the STM markers FOXF1, HNF4A, COL4A, and ALCAM was successfully induced by FGF2 and platelet-derived growth factor B (PDGFB) co-exposure at day 10, whereas the PSC marker NANOG and an early mesoderm marker T were barely detected (FIG. 2F (FIG. 2F)). Immunostaining of WT1, MIIA, and LHX2 also confirmed the correct cell fate induction in the presumptive STM cells (FIG. 3A (FIG. 3A)). Global gene array analysis suggested that iPSC-STM signatures show a remarkable shift toward reported human adult hepatic mesenchymal cell signatures (Asahina et al., 2009, Asahina et al., 2011, El Taghdouini et al., 2015) (FIG. 2G (FIG. 2G)). The present inventors previously demonstrated that one function of mesenchymal cells in LB generation is myosin-IIA-dependent self-condensation. Consistently, the present inventors demonstrated by time-lapse imaging that the self-condensation capacity of iPSC-STM was comparable to that of conventional BMSCs (FIG. 2H (FIG. 2H)).

In order to reproducibly generate endothelial progenitor cells (iPSC-EC), the present inventors developed four independent protocols that were modifications of previously described protocols, after adaptation into feeder-free iPSC culture (Narazaki et al., 2008, Orlova et al., 2014, Patsch et al., 2015, Samuel et al., 2013) (FIG. 11A (Figure S7A)). The iPSC-ECs subjected to full differentiation programs under each protocol were assessed by flow cytometric analysis (FACS) and qRT-PCR (FIGS. 11B and 11C (Figures S7B and S7C)). The results revealed that cells following Protocol 1 exhibited the highest expression of endothelial cell (EC) markers, minimizing pluripotency markers. Even without purification by magnetic-bead-based sorting, the combination of VEGF and forskolin induced the highest levels of CD144 (VE-cadherin) and CD31 co-expression, as determined by periodical FACS analysis (>92.8%, n=12) (FIG. 2I (FIG. 2I)). After serial passaging, ECs rigorously proliferated (~200-fold increase) (FIG. 11D (Figure S7D)), and this expression was maintained up to 4 passages. This was confirmed by immunostaining of endothelial markers; cells exhibited rigorous migration and subsequent endothelial spouting potential upon plating on a Matrigel plug (FIG. 2J (FIG. 2J)). More importantly, co-cultivation of iPSC-EC and iPSC-STM on a soft substrate led to formation of condensed tissues (Takebe et al., 2015) and was capable of generating patent blood vessels 48 hr after transplantation, as confirmed by confocal imaging of cells by using AAVS1::mCherry iPSC-ECs after fluorescent dextran infusion (FIG. 2K (FIG. 2K)). These results suggested that human iPSC-STM and iPSC-EC populations are successfully differentiated from feeder-free iPSCs with functional capacity for self-condensation and vascularization.

Figures 3A, 3B:
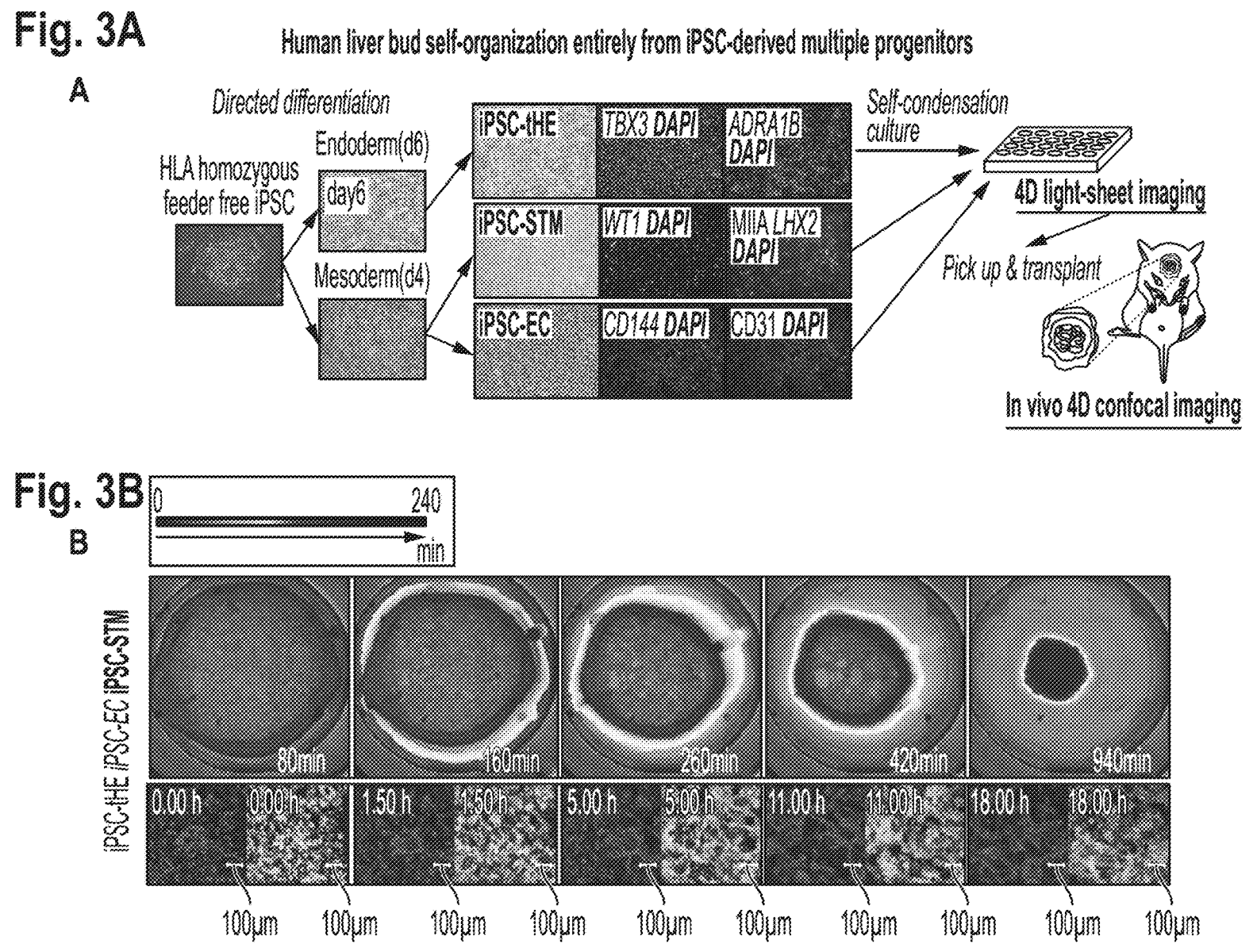

The robust induction of triple progenitors enabled the present inventors to examine the potential for generation of LBs entirely from iPSCs (generation of "all iPSC-LB") (FIG. 3A (FIG. 3A)). These three distinct progenitors were successfully induced from multiple human feeder-free iPSC sources (5 independent donor-derived clones were tested), including HLA homozygous clones such as Ff-101 and Ff-114. 4D bright-field and light-sheet image analysis showed successful self-condensation in the presence of STM (FIG. 3B (FIG. 3B), top) and self-organizing iPSC-EC networks (FIG. 3B (FIG. 3B), bottom), respectively. Confocal wide-field imaging of 3-day-cultured tissues confirmed sprouted iPSC-ECs in alignment with iPSC-tHEs (FIGS. 3C and 3D (FIGS. 3C and 3D)). Further, vascularization potential was assessed by transplantation into the cranial window of an immunodeficient mouse. Intravital imaging showed the formation of functional blood vessels at 48 hr and the eventual engraftment of iPSC-tHEs (FIG. 3E-3G (FIGS. 3E-3G)). iPSC-ECs directly anastomosed with mouse CD31 endothelial cells (FIG. 3H (FIG. 3H)) and were surrounded by iPSC-STMs at a perivascular location (FIG. 3I (FIG. 3I)). Thus, the present inventors have successfully generated vascularized and functional liver tissues entirely from human iPSCs.

Figure 4A:
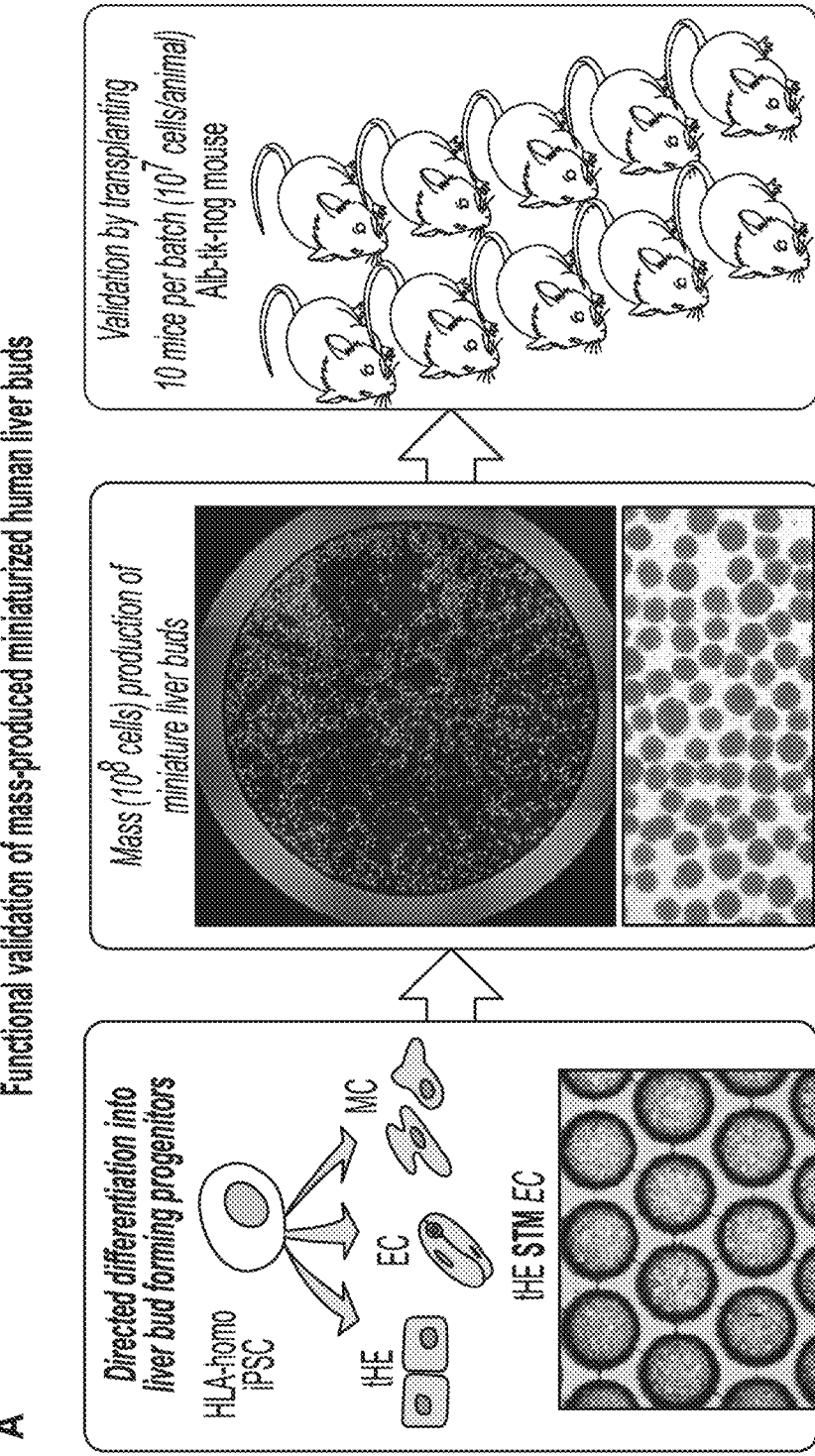
Figures 4B, 4C, 4D, 4E:
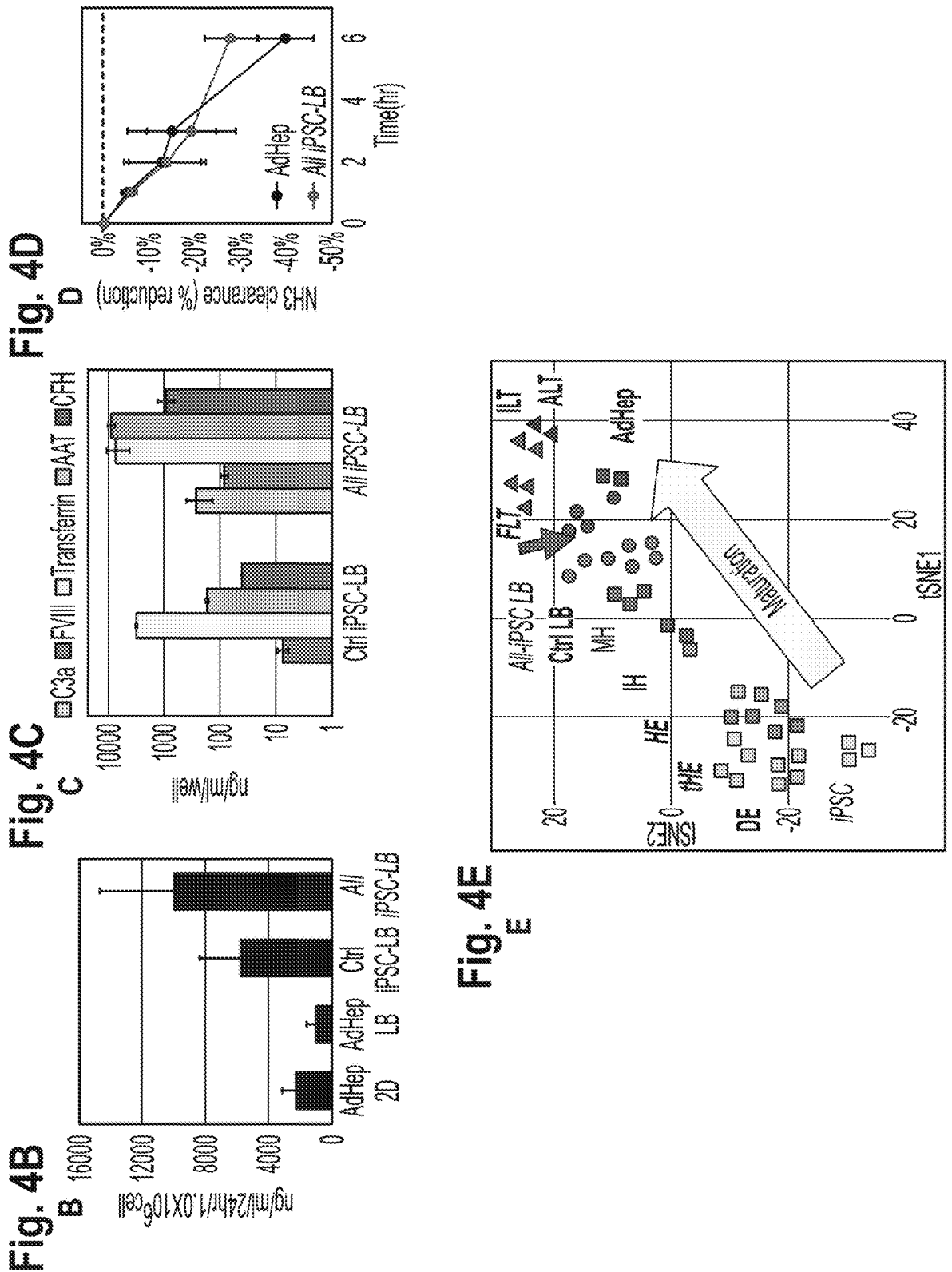
Figure 4F:
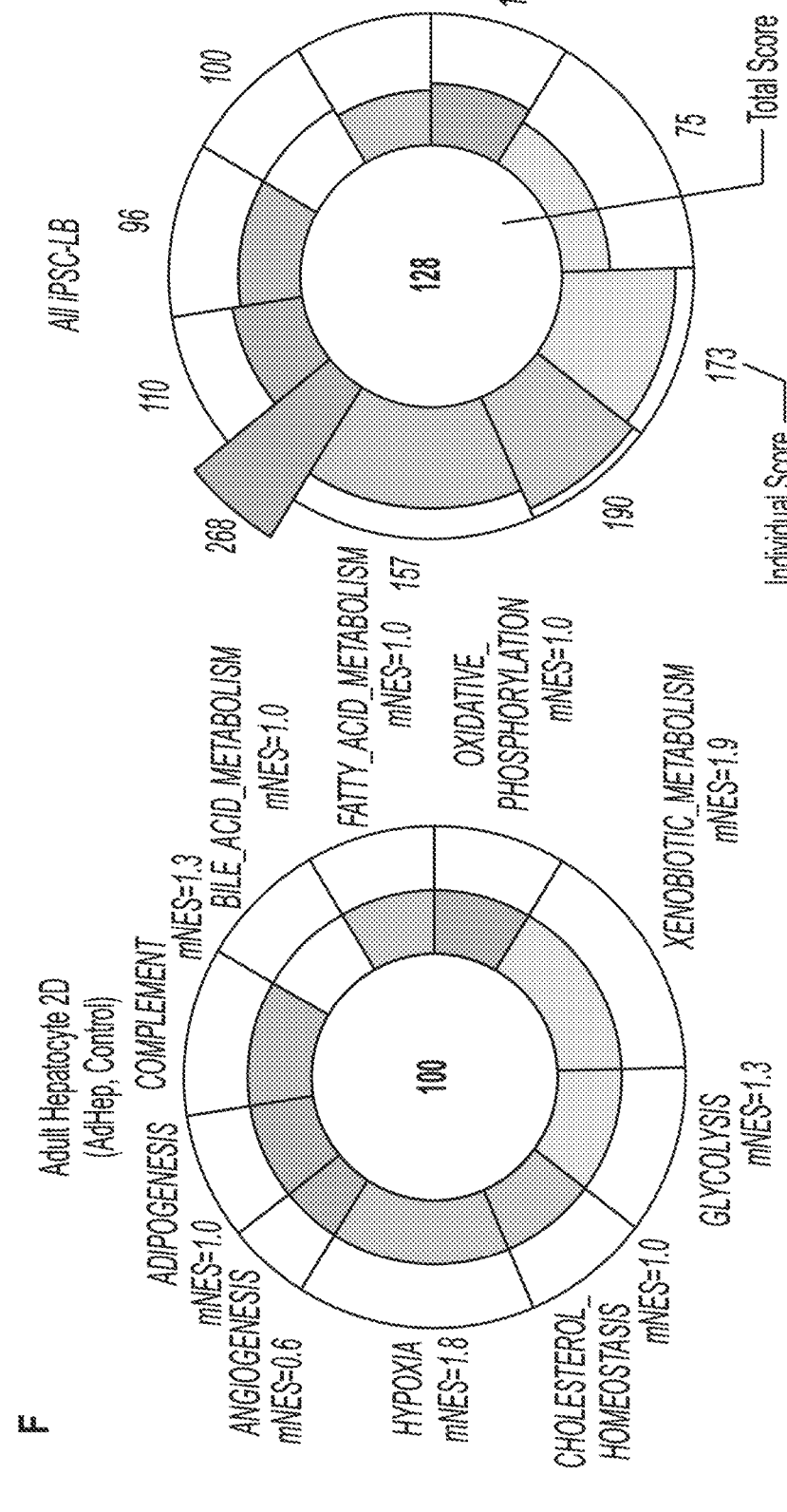

Since transplantation of at least $10^8$ hepatocytes is required to correct a specific metabolic liver function (Martin et al., 2014), the ultimate challenge is to adapt the all-iPSC-LB strategy to a culture platform scalable up to omni-well-array scale. To this aim, our strategy for mass production and batch validation of all iPSC-LBs is outlined in FIG. 4A (FIG. 4A). Briefly, the present inventors prepared 5-10 omni-well-array plates for manufacturing 108-cell-scale LBs per culture and characterized by in vitro functions and in vivo therapeutic potential. As a result, after 10 days of culture, mass-produced all iPSC-LBs not only exhibited higher albumin production (over 10 µg/mL/24 hr/$10^6$ cells) than conventional LBs (HUVEC/BMSC) or adult human hepatocytes (AdHep's) (FIG. 4B (FIG. 4B) and FIG. 9B (Figure S5B)) but also produced a number of key hepatic serum proteins, including complement factor H, coagulation factor VIII, transferrin, and AAT (FIG. 4C ((FIG. 4C)). Remarkably, the ammonium clearance potential of long-term cultured all iPSC-LBs was comparable to that of primary AdHep's in culture (FIG. 4D (FIG. 4D)). Additional global transcriptome analysis indicated that differentiated all iPSC-LBs are more mature than conventional LBs, comparable to AdHep's, but less mature than 30-year-old human adult liver tissues (FIG. 4E (FIG. 4E) and FIG. 9B (Figure S5B)). In order to make a fair comparison with human AdHep's, the present inventors developed a scoring method based on their hepatic functional gene signature data. This method was designated APRES (aster plot of relative enrichment score) algorithm. Using hallmark gene sets in MSigDB version 5.0 (Subramanian et al., 2005), the present inventors determined the width of each component of the aster plot using the relative size of the modified normalized enrichment score (mNES) calculated from the expressional level of progressive signatures in human adult hepatocytes (AdHep 2D) over fetal liver (see Experimental Procedures). For each tissue or cell type, the relative mNES score was shown as the height of each component of the aster plot after multiplying width and the height of the component, and then the total relative score was defined as a summation. Unbiased APRES-based scoring clearly indicated that the profiles of differentiated all-iPSC-LBs were similar to those of AdHep and conventional iPSC-MH, including complement, angiogenesis, and cholesterol homeostasis cascades (FIG. 4F (FIG. 4F)).

Finally, functional batch validation of mass-produced human LBs was carried out in an immunodeficient mouse model of liver failure. $10^8$ hepatic cell-equivalent LBs were prepared and then $10^7$ cell-equivalent LBs were distributed among about 10 mice per mass production so as to evaluate the entire buds by assessing their therapeutic potential. Transplantation was performed into the renal subcapsular site of an Alb-Tk-NOG mouse. Overall, the results collected from 114 transplanted mice provided statistically significant robust evidence for survival improvement as achieved by rescuing total liver dysfunction (FIG. 4G (FIG. 4G)). Importantly, follow-up serum analysis also supported the fact that mass-produced LBs are functionally stable by increasing albumin (ALB) and decreasing alpha fetoprotein (AFP) (not detected) in vivo independent of the production cycle (FIG. 12A (Figure S8A)). Notably, the magnitude and persistence of human albumin were significantly higher than those obtained from human primary hepatocyte (n=12, 4 donors) transplantation (FIG. 4H (FIG. 4H)). The drug metabolism capacity of LBs was also confirmed by human-specific diclofenac metabolite detection (FIG. 4I (FIG. 4I)). Transplantation of stromal cell-free iPSC-tHE cells was barely functional, as assessed by human ALB in the transplant mice (FIG. 12B (Figure S8B)), suggesting the potential role of iPSC-STM and iPSC-EC in hepatic functionalization as was shown in a recent study of single-cell RNA sequencing (Camp et al., 2017). To summarize, the organoid mass-production culture platform of the present inventors not only addresses the scaling issue but also provides a stringent and reproducible differentiation platform for a human iPSC-derived liver tissue which is comparable in function to more than 108 adult hepatocytes.

Discussion

In conclusion, the technology outlined in this study sheds light on an exciting strategy for iPSC-based multicellular organoid supply for drug testing and regenerative applications. Especially, production of more than $10^8$-cell-scale LBs achieved in this Example seems a reasonable scale for human transplant applications, as numbers of hepatocyte transplantation trials have demonstrated clinical efficacy at a minimum dose of $10^8$ cells, especially for pediatric patients (Enosawa et al., 2014, Jorns et al., 2012). Given that the standard therapeutic scale is $10^9$ hepatocytes per patient or even more (Horslen and Fox, 2004), continued scaling efforts would be anticipated in a parallel efficacy study in animal models of metabolic disorders. Nevertheless, this protocol is being developed through multiple academic and industrial collaboration efforts with the use of clinical-grade components, including genetically characterized iPSCs, defined media and substrates, microwell-array plates, and microscopic verification as a preparation for future clinical trials. To accelerate this, complete adaptation of the all-iPSC-LB strategy into a current Good Manufacturing Practices (cGMP)-grade system will be critical for future clinical applications as well as for safety assessment through clinically relevant transplant routing. Ultimately, the present inventors believe that through the integration of an array of manufacturing technologies, it will be feasible to develop a clinically effective LB transplant therapy for treating currently intractable liver diseases.

Experimental Procedures

Human Liver Bud Culture in Microwells

All iPSC lines were maintained on dishes in StemFit™ (Ajinomoto); the dishes had been coated with Laminin 511™ E8 fragment (iMatrix-511, kindly provided by Nippi). Methods for directed differentiation into each lineage are described in Supplemental Experimental Procedures. To generate human LBs in vitro, a total of 1,140-10,140 cells per microwell at a ratio of 10:7:2 (human iPSC-tHE/iPSC-EC/iPSC-STM) were resuspended in a mixture of endothelial cell growth medium (EGM) and hepatocyte culture medium (HCM) (Cambrex, Baltimore, MD) containing dexamethasone (0.1 μM; Sigma-Aldrich, St. Louis, MO), oncostatin M (10 ng/ml; R&D System, Minneapolis, MN), hepatocyte growth factor (HGF) (20 ng/mL, PromoKine), and SingleQuots (Lonza), and plated on either a 24-well plate or the Elplasia platform (co-developed by Kuraray, Inc.) in a 24-well, 6-well, or 1-well plate. The phase-contrast colony image shown in FIG. 3B (FIG. 3B) (top) was captured using a BioStation CT culture incubator, microscope, and digital imaging system (Nikon, Tokyo, Japan). The fluorescent time-lapse image shown in FIG. 3B (FIG. 3B) (bottom) was obtained with a Lightsheet Z.1 microscope (Zeiss, Germany). Generated human iPSC-LBs were collected by gentle pipetting and used for in vitro maturity assessment and in vivo transplantation experiments. As controls, the present inventors used five different human primary adult hepatocytes (lot numbers H768, H737, HC2-8, H4.1 and lot number: M00995, purchased from Xeno-Tech, KS, USA and Veritas, Tokyo, Japan).

Quantification and Statistical Analysis

Data are expressed as the means±SEM or means±SD of the number of independent experiments specified in the figure legends. No randomization or blinding method was used in this study. The statistical significance of the amount of albumin produced was assessed by the non-parametric Mann-Whitney U test. Two-tailed p values of <0.05 were considered significant. For survival analysis, GraphPad Prism Software version 6.0 was used for statistical analysis.

Supplemental Information

Supplemental information includes supplemental experimental procedures and eight figures (FIGS. 5 to 12 (Figures S1-S8)).

REFERENCES

Asahina, K., Tsai, S. Y., Li, P., Ishii, M., Maxson, R. E., Jr., Sucov, H. M., and Tsukamoto, H. (2009). Mesenchymal origin of hepatic stellate cells, submesothelial cells, and perivascular mesenchymal cells during mouse liver development. Hepatology 49, 998-1011.

Asahina, K., Zhou, B., Pu, W. T., and Tsukamoto, H. (2011). Septum transversum-derived mesothelium gives rise to hepatic stellate cells and perivascular mesenchymal cells in developing mouse liver. Hepatology 53, 983-995.

Camp, J. G., Sekine, K., Gerber, T., Loeffler-Wirth, H., Binder, H., Gac, M., Kanton, S., Kageyama, J., Damm, G., Seehofer, D., et al. (2017). Multilineage communication regulates human liver bud development from pluripotency. Nature 546, 533-538.

Delgado, I., Carrasco, M., Cano, E., Carmona, R., Garcia-Carbonero, R., Marin-Gomez, L. M., Soria, B., Martin, F., Cano, D. A., Munoz-Chapuli, R., et al. (2014). GATA4 loss in the septum transversum mesenchyme promotes liver fibrosis in mice. Hepatology 59, 2358-2370.

Ding, Q., and Cowan, C. A. (2013). Liver in a dish. Cell Res 23, 1242-1243.

El Taghdouini, A., Sorensen, A. L., Reiner, A. H., Coll, M., Verhulst, S., Mannaerts, I., Oie, C. I., Smedsrod, B., Najimi, M., Sokal, E., et al. (2015). Genome-wide analysis of DNA methylation and gene expression patterns in purified, uncultured human liver cells and activated hepatic stellate cells. Oncotarget 6, 26729-26745.

Enosawa, S., Horikawa, R., Yamamoto, A., Sakamoto, S., Shigeta, T., Nosaka, S., Fujimoto, J., Nakazawa, A., Tanoue, A., Nakamura, K., et al. (2014). Hepatocyte transplantation using a living donor reduced graft in a baby with ornithine transcarbamylase deficiency: a novel source of hepatocytes. Liver Transpl 20, 391-393.

Horslen, S. P., and Fox, I. J. (2004). Hepatocyte transplantation. Transplantation 77, 1481-1486.

Huch, M., and Koo, B. K. (2015). Modeling mouse and human development using organoid cultures. Development 142, 3113-3125.

Iyer, D., Gambardella, L., Bernard, W. G., Serrano, F., Mascetti, V. L., Pedersen, R. A., Talasila, A., and Sinha, S. (2015). Robust derivation of epicardium and its differentiated smooth muscle cell progeny from human 460 pluripotent stem cells. Development 142, 1528-1541.

Jorns, C., Ellis, E. C., Nowak, G., Fischler, B., Nemeth, A., Strom, S. C., and Ericzon, B. G. (2012). Hepatocyte transplantation for inherited metabolic diseases of the liver. J Intern Med 272, 201-223.

Kajiwara, M., Aoi, T., Okita, K., Takahashi, R., Inoue, H., Takayama, N., Endo, H., Eto, K., Toguchida, J., Uemoto, S., et al. (2012). Donor-dependent variations in hepatic differentiation from human-induced pluripotent stem cells. Proc Natl Acad Sci USA 109, 12538-12543.

Kolterud, A., Wandzioch, E., and Carlsson, L. (2004). Lhx2 is expressed in the septum transversum mesenchyme that becomes an integral part of the liver and the formation of these cells is independent of functional Lhx2. Gene Expr Patterns 4, 521-528.

Lancaster, M. A., and Knoblich, J. A. (2014). Organogenesis in a dish: modeling development and disease using organoid technologies. Science 345, 1247125.

Loh, K. M., Ang, L. T., Zhang, J., Kumar, V., Ang, J., Auyeong, J. Q., Lee, K. L., Choo, S. H., Lim, C. Y., Nichane, M., et al. (2014). Efficient endoderm induction from human pluripotent stem cells by logically directing signals controlling lineage bifurcations. Cell stem cell 14, 237-252.

Martin, I., Simmons, P. J., and Williams, D. F. (2014). Manufacturing challenges in regenerative medicine. Sci Transl Med 6, 232fs16.

Narazaki, G., Uosaki, H., Teranishi, M., Okita, K., Kim, B., Matsuoka, S., Yamanaka, S., and Yamashita, J. K. (2008). Directed and systematic differentiation of cardiovascular cells from mouse induced pluripotent stem cells. Circulation 118, 498-506.

Orlova, V. V., van den Hil, F. E., Petrus-Reurer, S., Drabsch, Y., Ten Dijke, P., and Mummery, C. L. (2014). Generation, expansion and functional analysis of endothelial cells and pericytes derived from human pluripotent stem cells. Nat Protoc 9, 1514-1531.

Patsch, C., Challet-Meylan, L., Thoma, E. C., Urich, E., Heckel, T., O'Sullivan, J. F., Grainger, S. J., Kapp, F. G., Sun, L., Christensen, K., et al. (2015). Generation of vascular endothelial and smooth muscle cells from human pluripotent stem cells. Nat Cell Biol 17, 994-1003.

Samuel, R., Daheron, L., Liao, S., Vardam, T., Kamoun, W. S., Batista, A., Buecker, C., Schafer, R., Han, X., Au, P., et al. (2013). Generation of functionally competent and durable engineered blood vessels from human induced pluripotent stem cells. Proc Natl Acad Sci USA 110, 12774-12779.

Sasai, Y. (2013). Cytosystems dynamics in self-organization of tissue architecture. Nature 493, 318-326.

Si-Tayeb, K., Noto, F. K., Nagaoka, M., Li, J., Battle, M. A., Duris, C., North, P. E., Dalton, S., and Duncan, S. A. (2010). Highly efficient generation of human hepatocyte-like cells from induced pluripotent stem cells. Hepatology 51, 297-305.

Subramanian, A., Tamayo, P., Mootha, V. K., Mukherjee, S., Ebert, B. L., Gillette, M. A., Paulovich, A., Pomeroy, S. L., Golub, T. R., Lander, E. S., et al. (2005). Gene set enrichment analysis: a knowledge-based approach for interpreting genome-wide expression profiles. Proc Natl Acad Sci USA 102, 15545-15550.

Takebe, T., Enomura, M., Yoshizawa, E., Kimura, M., Koike, H., Ueno, Y., Matsuzaki, T., Yamazaki, T., Toyohara, T., Osafune, K., et al. (2015). Vascularized and Complex Organ Buds from Diverse Tissues via Mesenchymal Cell-Driven Condensation. Cell Stem Cell 16, 556-565.

Takebe, T., Sekine, K., Enomura, M., Koike, H., Kimura, M., Ogaeri, T., Zhang, R. R., Ueno, Y., Zheng, Y. W., Koike, N., et al. (2013). Vascularized and functional human liver from an iPSC-derived organ bud transplant. Nature 499, 481-484.

Takebe, T., Zhang, R. R., Koike, H., Kimura, M., Yoshizawa, E., Enomura, M., Koike, N., Sekine, K., and Taniguchi, H. (2014). Generation of a vascularized and functional human liver from an iPSC-derived organ bud transplant. Nat Protoc 9, 396-409.

Witty, A. D., Mihic, A., Tam, R. Y., Fisher, S. A., Mikryukov, A., Shoichet, M. S., Li, R. K., Kattman, S. J., and Keller, G. (2014). Generation of the epicardial lineage from human pluripotent stem cells. Nat Biotechnol 32, 1026-1035.

Zaret, K. S. (2002). Regulatory phases of early liver development: paradigms of organogenesis. Nat Rev Genet 3, 499-512.

Details of Experimental Models and Subjects

Mice

In vitro generated LBs were collected and transplanted into a preformed cranial window or other indicated sites in non-obese diabetic/severe combined immunodeficient (NOD/SCID) mice (Sankyo Lab. Co., Tsukuba, Japan). The in vivo fate of the transplanted cells was monitored by intravital imaging using a Leica TCS SP8 confocal microscope (Leica Microsystems, Germany). For the in vivo functionalization studies, 8-week-old male NOG mice (~20-30 g body weight) were used (supplied by the Central Institute for Experimental Animals (CIEA), Kanagawa, Japan) (Hasegawa et al., 2011). For survival curves, albumin-TK-NOG mice (~20-30 g body weight) were used in this study (supplied by CIEA, Kanagawa, Japan). Ganciclovir (GCV, 50 mg/kg, i.p.), a drug that is not toxic to human or mouse tissues, was administered to induce tissue-specific ablation of transgenic liver parenchymal cells prior to transplantation, and $1 \times 10^7$ cell-equivalent iPSC-LBs per mouse were transplanted into the subscapular site of the kidney. The sample size was determined by the minimum size necessary to obtain a significant difference (P<0.05) at a power of 80% when there was a 30% change in the secreted albumin protein. The time point of euthanasia was randomly assigned. As for exclusion criteria for the transplant experiments, the present inventers pre-determined to exclude data from mice euthanized due to sickness, which are not related to transplantation. The mice were bred and maintained according to the Yokohama City University institutional guidelines for the use of laboratory animals.

Method Details

Human iPSC Culture and tHE Differentiation

Human iPSC lines (TkDA3-4, 1231A3, 1383D2, 1383D6 and Ff01) were kindly provided by Kyoto University and Tokyo University. 1231A3, 1383D2 and 1383D6 were established from ePBMC™ (Cellular Technology Limited, OH) at CiRA, Kyoto University. All iPSC lines were maintained on dishes in StemFit™ (Ajinomoto Co., Inc.); the dishes had been coated with Laminin 511 E8 fragment (iMatrix-511™, kindly provided by Nippi, Inc.) For in vitro and in vivo live imaging analysis, fluorescent protein knock-in reporters under the expression of adeno-associated virus integration site 1 (AAVS1::EGFP or mCherry) were used. To derive iPSC-tHEs, the present inventors developed a two-stage differentiation method (see, supplemental text). At the first stage, human iPSCs were seeded on an iMatrix-511-coated dish together with 10 μM ROCK Inhibitor Y-27632 (Wako, cat. no. 253-00513), and RPMI-1640 with 1% B27, 100 ng/ml human activin A (provided by Ajinomoto Inc.) and 50 ng/ml Wnt3a (R&D Systems) was used as the medium for 6 days. On the initial day of iPSC plating, 1 mM sodium butyrate (Sigma) was added. Successful endoderm specification was quantitatively assessed using Cerberus 1 ELISA kit (Dojin Kagaku, Kumamoto, Japan). Subsequently, human iPSC-derived endodermal cells were treated further with RPMI-1640 with 1% B27, 10 ng/ml human basic FGF, and 20 ng/ml human BMP4 for 2 days to derive a TBX3 and ADRA1B co-positive transitional hepatic endoderm population. Prior to adapting the described protocols for different iPSC clones, the present inventors strongly recommend that the respective specification markers of human iPSCs be examined at each time point of differentiation by immunostaining and gene expression studies in addition to careful microscopic observation, because successful liver bud generation is crucial for in vivo functional maturation. The use of human iPSC in this Example was approved by the Ethics Committee of the Yokohama City University.

Human iPSC-EC and STM Differentiation

For EC differentiation, human iPSCs were dissociated using Accutase and plated on Laminin 511 E8 fragment (iMatrix-511™, provided by Nippi, Inc.) at varying optimal densities (depending on the cell line) in StemFit™ (Ajinomoto Co., Inc.) with 10 µM ROCK inhibitor Y-27632. Next day, the medium was replaced with Priming Medium consisting of B27 medium [a 1:1 mixture of DMEM:F12 with 1% Glutamax and 1% B27 (all from Life Technologies)] containing 8 µM CHIR99021 (Tocris Bioscience) and 25 ng/ml BMP4 (R&D Systems). After additional three days, the priming medium was replaced with EC Induction Medium consisting of StemPro-34 SFM medium (Life Technologies) supplemented with 200 ng/ml VEGF (Life Technologies) and 2 µM forskolin (Sigma-Aldrich). The induction medium was renewed every day. At day 7 of differentiation, ECs were dissociated with 0.05% Trypsin and subjected to FACS analysis. iPSC-derived ECs are supposed to exhibit a typical endothelial morphology with localization of CD144/CD31 junctions. ECs were replated on 1 µg/cm² Fibronectin (Sigma-Aldrich)-coated dishes at a density of 50,000 cells/cm² in EC Expansion Medium consisting of StemPro-34 SFM supplemented with 50 ng/ml VEGF-A. EC 7 Expansion Medium was replaced every other day. For STM differentiation, human iPSCs were dissociated using Accutase, plated on Laminin 511 E8 fragment at 2000-8000 cells/cm² (depending on the cell line) in StemFit™ with 10 µM ROCK inhibitor Y-27632 and cultured for 4-6 days before induction. At the mesoderm induction stage, maintenance medium was replaced with mesoderm induction medium (1:1 mixture of DMEM:F12 with 1% Glutamax and 1% B27, the mixture further containing 8 µM CHIR99021 and 25 ng/ml BMP4; subsequently, 3 day-exposure to 2 ng/ml activin A and 10 ng/ml PDGFBB (R&D Systems) followed. After three days, the mesoderm induction medium was replaced with STM induction medium consisting of StmePro-34 SFM medium supplemented with 10 ng/ml FGF2 and 10 ng/ml PDGFBB, and cells were cultured for three days.

Elplasia™ Micro-Well Plate Manufacturing Process

Elplasia™ micro-well plate was industrially manufactured by a combination of two techniques; one for making a finely-structured metal mold and the other for transferring the structure accurately from the mold to a resin film. The production of such a finely-structured metal mold started with a process of master block preparation. The present inventors engraved micro-wells in a metal plate at equal distances by precise metal cutting work. Each micro-well was U-bottom shaped with an aperture diameter of about 500 µm and a depth of 400 µm. They were closely and triangularly arranged at 30 µm intervals in order that all the seeded cells would be distributed among individual micro-wells. The metal cutting work was followed by cutting into a square shape, polishing back side and giving a mold release treatment that improves detachment of resin from the metal mold. Through the above processes, a nickel plate was generated as a metal mold whose surface had many micro-pillars as inverted forms of micro-wells. Transfer of the micro-well structure from mold to resin film was conducted by using an internally developed transfer molding machine. Compared to the common injection molding machine, the developed molding machine significantly improves transfer accuracy especially in the part of high aspect ratio area such as the plate configuration of the present inventors (The 'aspect ratio' is the ratio of height to width of microstructure). In fact, the micro-well (depth: 400 µm, interval; 30 µm) of the present inventors has extremely high aspect ratio that is hard to transfer by the conventional molding machine. The present inventors attached the metal mold to the molding machine, and then applied melted polystyrene resin on the mold. Through several conditional optimizations including temperature, press weight and retention time, the present inventors finally obtained a resin film onto which micro-wells had been completely transferred. Trimmed film was welded with pre-made well plate frame without bottom, thereby completing Elplasia™ micro-well plate having a micro-well array in the bottom. Since there are about 320 micro-wells in every 1 cm² area, there are about 600 micro-wells/well in 24-well plate format, about 3,000 micro-wells/well in 6-well plate format, and about 20,000 micro-wells/plate in omni-plate format.

In Vitro Imaging

Acquisition of phase-contrast colony images shown in FIG. 3B (FIG. 3B) (upper panel) was achieved using a BioStation CT culture incubator, a microscope and a digital imaging system (Nikon, Tokyo, Japan) preadjusted to optimize the auto-focus and cell image-tiling acquisition functions according to the instructions provided. Fluorescent time-lapse imaging shown in FIG. 3B (FIG. 3B) (lower panel) was imaged with Lightsheet Z.1 microscope (Zeiss, Germany).

Intravital Imaging

Tail vein injections of 1% tetramethylrhodamine-conjugated dextran (MW 2,000,000), fluorescein isothiocyanate-conjugated dextran (MW 2,000,000) and Texas Red-conjugated dextran (70,000 MW, neutral) were used to identify vessel lumens (all from Invitrogen, Carlsbad, CA, USA). Host endothelial cells were visualized using intravenously injected Alexa647-conjugated mouse-specific CD31 (BD). Confocal image stacks were acquired for the implanted vessels and dextran.

Gene Expression Analysis qRT-PCR analyses were conducted as described previously (Takebe et al., 2013). For the microarray, total RNA was prepared using an RNeasy Mini Kit (Qiagen, Valencia, CA). RNA for gene expression profiling was hybridized on Whole Human Genome Agilent 4×44K v2 Oligonucleotide Microarray or Whole Human Genome Agilent 8×60K v2 Oligonucleotide (Agilent Technologies, Palo Alto, CA) according to the manufacturer's instructions. For control samples, human FLT (10 gwk or 22-40 gwk pool Fetal Liver Tissue), ILT (0 yr Infant Liver Tissue) and ALT (5 yrs, 30 yrs, 44 yrs or 55 yrs old Adult Liver Tissues) RNA samples were obtained from Biochain Institute (Hayward, CA, USA) in addition to the above-descried human primary hepatocyte samples.

Hierarchical Clustering Analysis

Microarray data were processed using the GeneSpring standard protocol. Briefly, a signal intensity less than 1 was corrected to 1 (not detected), and then the 75th percentile shift normalization was conducted. After averaging the signal intensity within replicate spots, the batch effect, observed within different 8×60 k v2 array chips (data not shown), was removed by Combat (Leek et al., 2012) with covariates of the same differentiation stages. When comparing with data from 4×44 k v2 arrays, the present inventors conducted quantile normalization for robustly removing the difference among chips and the batch effects. To analyze the genome-wide differentiation state, the present inventors performed principal component analysis (PCA) (Lê et al., 2008) using the scaled expression levels of protein-coding genes. Because the top principal component (PC) explained nearly 40% of the variance in all samples including 2-D cultured iPSCs and clinical specimens, the present inventors mainly used PC1 (FIG. 2D (FIG. 2D)). Unsupervised hierarchical clustering was performed with Pearson's correlation-based distance and average linkage method. To characterize development, we used the discovery lifemaps gene signatures acquired from http://discovery.lifemapsc.com/in-vivo-development/2015/4/8, and p-values from Gene Set Enrichment Analysis (GSEA) (Subramanian et al., 2005) were shown by heat map (FIG. 2H (FIG. 2H), comparison is described in this figure). Unless otherwise specified, data processing and analysis were performed using the statistical software R, version 3.0.1.

APRES (Aster Plot of Relative Enrichment Score) Algorithm

First, using hallmark gene sets in MSigDB version 5.0 (Subramanian et al., 2005), the present inventors conducted enrichment analysis which compares several different stages of tissue/cells with human fetal liver tissue (FLT, 10 w). Calculated normalized enrichment score (NES) by GSEA software, was converted into modified NES (mNES) as follows: if NES>1, then mNES is NES; if –1<NES<1, then mNES is 1; otherwise, mNES is 1/|NES|. This conversion allows the present inventors to compare NESs regardless of whether a target gene set was enriched in comparing sample or FLT. Next, the present inventors determined the width of each component of aster plot using the relative size of mNES calculated from comparison of human adult hepatocyte (AHEP 2D) versus FLT. For each tissue or cell type, relative mNES score was calculated as divided by mNES of AHEP 2D versus FLT, and this score was shown as the height of each component of aster plot. Finally, the present inventors multiplied the width and the height of the component, and then defined a total relative score by adding up the products. Total relative score is indicated at the center of the aster plot (FIG. 4F (FIG. 4F)).

ELISA

Blood samples were allowed to clot in a centrifuge tube (approximately 5 min) at room temperature, loosened from the sides of the tube and incubated at 4° C. (melting ice) for 20 min. Clotted blood was centrifuged for 10-15 min at 400 g at 4° C., and the serum fraction was removed with care being taken to exclude erythrocytes or clotted materials. Human CER1, ALB and AAT were measured in mouse serum samples using Human Cerberus 1 Quantification Kit (Dojin Kagaku, Kumamoto, Japan), Human Albumin ELISA Quantitation Kit (Bethyl Laboratories Inc., Montgomery, TX, USA) and human alpha 1-antitrypsin ELISA Quantitation Kit (GenWay Biotech, Inc., San Diego, CA, USA), according to the manufacturers' instructions. Blinded investigators performed all the ELISA experiments using in vitro culture supernatant or in vivo serum.

Data and Software Availability

The accession number of the microarray data reported in this Example will be updated once the data was uploaded via NCBI GEO.

Supplemental Text

Miniaturized Liver Bud Culture

After selecting a coating material (FIG. 5 (Fig. S1)), the present inventors first optimized the cell culture conditions by conducting mixture ratio- and dose-dependency studies. A mixing protocol for endothelial cells versus total cells was previously optimized based on efficient post-transplant vascularization (Takebe et al., 2014); however, a protocol for mesenchymal cells has not yet been determined. SEM analysis confirmed that 10%-1.4% (⅕-1/40 of endodermal cells) of the mesenchymal cell mixture enables reproducible LB generation (FIG. 6A (Figure S2A)), and subsequent gene expression analysis suggested that 2.8% (1/20 of endodermal cells) is the most efficient proportion for stable hepatic differentiation and tissue formation (FIG. 6B, C (Figure S2B, C)). The present inventors next performed a dose-reduction study to determine the minimal cell numbers for functional LB production (FIG. 6D-F (Figure S2D-F)). Cell number dependent LB size is shown in FIG. 6D (Figure S2D); LB size increased in a dose-dependent manner up to 4000 cells (over 6000 cells per microwell failed to form LB). An ELISA-based functional screening on long-term differentiated LB demonstrated that inclusion of 600 iPSC-tHE cells (total 1130 cells) per LB produced the highest level of human albumin compared to the inclusion of a larger or smaller number of iPSC-tHE cells (within the range from 150-1200 iPSC-tHE cells per LB) (FIG. 6F (Figure S2F)), as also confirmed by gene expression analysis of additional hepatic differentiation markers (FIG. 6D, E (Figure S2D, E).

Selection of Highly Efficient Differentiation Protocols for Generating Hepatocyte-Like Cells The present inventors performed a number of 'reverse' screen experiments by comparing the morphology and functionality of differentiated liver buds using endodermal cells of multiple differentiation stages. A huge number of publications reported that each specific method by sequential addition of genes and proteins results in hepatocyte-like cell production; however, comparative analyses were seldom performed. Initially, 2-D based screens were performed to select three promising step-wise differentiation protocols (Kajiwara et al., 2012; Loh et al., 2014; Si-Tayeb et al., 2010) (FIG. 8A (Fig. S4A)). Then, the three major protocols were modified to become suitable for the feeder-free iPSC culture of the present inventors by optimizing cell density, cytokine exposure duration and basal media; as a result, differentiated cells in Protocol (Pr) 1 revealed minimized expression of pluripotent markers (OCT4 and 17 NANOG) and higher expression of hepatic markers (FOXA2, HNF4A, ALB and AFP) in definitive endoderm (DE) and mature hepatocyte-like (MHs) cells compared with Pr 2 and Pr 3 (FIG. 8B-E (Figure S4B-E)). These results were confirmed by human albumin secretion analysis by ELISA, which revealed that the secretion from MH of Pr 1 was approximately 2.5 times that of Pr 2 and Pr 3 (data not shown). Under Pr1 which amplifies Wnt signaling pathways, four different patient-derived iPSC clones were capable of differentiating functional hepatocyte-like cells in a highly reproducible manner (FIG. 4F (FIG. 4F)). To summarize, Wnt3A exposure in early endoderm specification is effective for generating functional hepatocyte-like cells in 2D culture.

Prospective Validation by Detecting CER1 Secretion

To identify prospective validation markers, transcriptome-based comparison of albumin high (good)/low (bad) MH and original DE cells was performed. The results suggested that better outcomes in 2D MH function correlates with the efficiency of DE specification (data not shown). Therefore, the present inventors hypothesized that successful hepatic maturation is largely dependent on the quality of early endoderm specification, particularly at the DE stage. In order to identify good DE markers, the present inventors compared the global gene expression profiles of good and bad DEs (as distinguished by eventual iPSC-MH functionality) and found that good DEs tend to express Cerberus 1 (CER1) at a much higher level (Iwashita et al., 2013). Cerberus 1 is a secretory and a known definitive endodermal maker, the level of which can be measured in a culture supernatant by ELISA. Thus, the present inventors found that detection of CER1 protein in culture media at day 6 is at least essential for the final ALB detection at day 20 (FIG. 4G (FIG. 4G)). This suggests that the secreted protein level at day 6 might be a potential requirement for hepatic functions after the completion of terminal differentiation.

SUPPLEMENTAL REFERENCES

Iwashita, H., Shiraki, N., Sakano, D., Ikegami, T., Shiga, M., Kume, K., and Kume, S. (2013). Secreted cerberus1 as a marker for quantification of definitive endoderm differentiation of the pluripotent stem cells. PLOS One 8, e64291.

Kajiwara, M., Aoi, T., Okita, K., Takahashi, R., Inoue, H., Takayama, N., Endo, H., Eto, K., Toguchida, J., Uemoto, S., et al. (2012). Donor-dependent variations in hepatic differentiation from human-induced pluripotent stem cells. Proc Natl Acad Sci U S A 109, 12538-12543. Loh, K. M., Ang, L. T., Zhang, J., Kumar, V., Ang, J., Auyeong, J. Q., Lee, K. L., Choo, S. H., Lim, C. Y., Nichane, M., et al. (2014). Efficient endoderm induction from human pluripotent stem cells by logi-cally directing signals controlling lineage bifurcations. Cell stem cell 14, 237-252.

Si-Tayeb, K., Noto, F. K., Nagaoka, M., Li, J., Battle, M. A., Duris, C., North, P. E., Dalton, S., and Duncan, S. A. (2010). Highly efficient generation of human hepatocyte-like cells from induced pluripotent stem cells. Hepatology 51, 297-305.

Takebe, T., Zhang, R. R., Koike, H., Kimura, M., Yoshizawa, E., Enomura, M., Koike, N., Sekine, K., and Taniguchi, H. (2014). Generation of a vascularized and functional human liver from an iPSC-derived organ bud transplant. Nat Protoc 9, 396-409.

Example 2

Directed differentiation of human iPSC into tHE was performed. Human iPSC culture and tHE differentiation were carried out in the same manner as described in Example 1 except for the following modifications.

Briefly, at the first stage, human iPSCs were seeded in iMtrix-511-coated dishes together with 10 μM ROCK inhibitor Y-27632 (Wako, Cat. No. 253-00513). After adding 1% B27, RPMI-1640 containing 100 ng/ml human activin A (kindly provided by Ajinomoto Co., Inc.) and 50 ng/ml Wnt3a (R&D Systems) was used as a medium for 6 days. By adding 2 μM CHIR99021 for 3 days instead of the above 50 ng/ml Wnt3a, cost reduction, xeno-free culture, and compatibility with the "Japanese Standards for Biological Ingredients" are achieved (FIGS. 13 and 14).

A schematic diagram of the protocol using CHIR99021 as an alternative for Wnt3a is shown in FIG. 13A. As a result of preliminary examination, a condition was selected such that 2 μM CHIR99021 is added for 3 out of the 6 days of DE directed differentiation.

Cell morphologies at each differentiation stage in the conventional method using Wnt3a and under the condition of adding 2 μM CHIR99021 for 3 days are shown in FIG. 13B. No morphological differences are observed compared to the case of using Wnt3a.

Flow cytometry analyses of the positive ratio for CXCR4 (a DE marker) at the DE stage in the conventional method using Wnt3a and under the condition of adding 2 μM CHIR99021 for 3 days are shown in FIG. 13C. The positive ratio for CXCR4 in the latter case is comparable to the ratio in the case of using Wnt3a.

Expression analyses of individual differentiation markers by pPCR are shown in FIG. 13D. Marker expressions at individual stages that were obtained in the case of using DHIR d3 are comparable to those obtained in the case of using Wnt3a.

ELISA analysis of albumin secretion at the MH stage is shown in FIG. 13E. In multiple iPSC clones, albumin secretion in the case of using CHIR d3 tends to be comparable to, or higher than, the secretion in the case of using Wnt3a.

The cellular morphologies in MH (FIG. 14A) and LB (FIG. 14B) revealed no morphological differences as compared to the case of using Wnt3a.

Maker expression analyses in MH and LB by qPCR are shown in FIG. 14C. With respect to marker expression levels and ALB secretion levels, no significant difference was observed between Wnt3a and CHIR; there was observed no increase, either, in the expression of marker genes of other cell lineages (such as intestinal markers).

Example 3

EC extended culture was performed. Human iPSC-EC differentiation and STM differentiation were carried out in the same manner as described in Example 1, except for the following modifications.

For EC differentiation, human iPSCs were dissociated with Accutase and plated on Laminin 511 E8 fragment (iMatrix-511™, kindly provided by Nippi, Inc.) The medium was replaced with a priming medium containing a ROCK inhibitor. The priming medium is composed of 8 µM CHIR99021 (Tocris Bioscience)- and 25 ng/ml BMP4 (R&D Systems)-containing B27 medium [which is a 1:1 mixture of DMEM and F12, containing 1% Glutamax and 1% B27 (both from Life Technologies)]. This medium is exchanged with a ROCK-inhibitor-free priming medium on the next day.

Three days later, the priming medium was exchanged with an EC induction medium. This EC induction medium is composed of StemPro-34 SFM medium (Life Technologies) supplemented with 200 ng/ml VEGF (Life Technologies) and 2 µM forskolin (Sigma-Aldrich). The induction medium was renewed every day. At day 7 of differentiation, ECs were dissociated with 0.05% trypsin and subjected to FACS analysis. iPSC-derived ECs are supposed to exhibit a typical endothelial morphology with localization of CD144/CD31 junctions. ECs were re-plated on Laminin 511 E8 fragment (iMatrix-511™, kindly provided by Nippi, Inc.) in ROCK inhibitor-containing EC extended medium at a density of 50,000 cells/cm². The EC extended medium is composed of StemPro-34 SFM medium supplemented with 50 ng/ml VEGF-A.

On the next day, the medium was exchanged with Mira-cellTM EC (Takara Bio), which was then exchanged every other day.

By these procedures, it is possible to obtain highly CD31/CD144 co-positive cells in a more stable manner (FIGS. 15 and 16).

A revised version of directed differentiation protocol for iPS-derived vascular endothelial cells (iPS-EC) is shown in FIG. 15.

A schematic diagram of the directed differentiation protocol is shown in FIG. 16A.

Cellular morphologies from the conventional method and the revised method are shown in FIG. 16B. No morphological differences are observed.

Flow cytometry analyses of the positive ratio for EC markers in the conventional method and the revised method are shown in FIG. 16C.

The flow cytometry analyses in FIG. 16C are summarized in FIG. 16D. High CD31/CD144 positive ratios are obtained more stably in the revised method than in the conventional method.

Expression analyses of individual differentiation markers by qPCR are shown in FIG. 16E. Expression levels of EC markers are stable in the revised method even after passages.

Cell growth upon each passage is shown in FIG. 16F. Growth capacity after passages is high in the revised method compared to the conventional method.

These results show that even when the positive ratio was not stable in EC at P0, stable EC production was possible by re-seeding. Thus, the present inventors have succeeded in proliferating ECs after their completion.

All publications, patents and patent applications cited herein are incorporated herein by reference in their entirety.

[Example 4] Preparation of an Organ from Undifferentiated Organ Cell

Experimental Methods (1) Preparation of Human Hepatic Endoderm Cells

Human iPS cells (human skin-derived TkDA3 hiPSC clone (provided by Mr. Koji Eto and Mr. Hiromitsu Nakauchi)) were cultured in an activin-supplemented serum-free medium to thereby induce CXCR4- and E-cadherin-positive endodermal cells. The resultant endodermal cells were cultured in the presence of added BMP4 and FGF2 for 2 days to thereby obtain CXCR4-negative and HNF4α-positive hepatic endoderm cell populations. Expression of CXCR4 and HNF4α was confirmed by immunostaining and gene expression analysis as described previously (Hepatology, 51(1), 297-305, 2010).

(2) Preparation of Human Liver Buds

The resultant hepatic endoderm cell was cocultured with a vascular endothelial cell (human umbilical cord blood-derived vein endothelial cell) (Lonza, Basel, Switzerland) and an undifferentiated mesenchymal cell (human mesenchymal stem cell) (Lonza, Basel, Switzerland) mixed at 10:5-10:2. The vascular endothelial cell and the undifferentiated mesenchymal cell were individually labeled with fluorescence in advance. In the coculture, cell suspension was seeded on pre-solidified Matrigel (BD pharmingen) (stock gel or 2-fold dilution) in a culture dish. As a culture broth, endothelial cell medium kit-2: EGM-2 BulletKit (product code CC-3162: Lonza) was used.

Cells were cultured for a short period of time (3-10 days) to prepare human three-dimensional structures (liver buds). The process of formation and the formed structures were observed under confocal microscope, and kinetic/static analyses of cell morphology and localization were performed. Further, gene expression analysis was performed on the thus formed human three-dimensional structures.

(3) Preparation of Human Liver Tissue

The formed human three-dimensional structure was transplanted into the living body of an immunodeficient mouse (NOD/SCID mouse (Sankyo Lab. Co., Tsukuba, Japan)). Macroscopic and confocal microscopic live observations were performed, followed by confirmation of engraftment/proliferation of human cells and analysis of post-transplantation vascular maturation processes. Early samples (2 weeks post-transplantation) were recovered and analyzed histologically.

Experimental Results (1) Autonomous organization progressed only from human cells, forming a macroscopically observable three-dimensional structure (FIG. 17)

(2) At day 4 of culture, a vessel-like luminal structure was confirmed (FIG. 17, upper right panel, enlarged image).

(3) The formed three-dimensional structure was attenuated in the expression of undifferentiated cell markers NANOG and CXCR4 (FIG. 18).

(4) Compared with those cells in which terminal differentiation was induced by conventional techniques, expression of a hepatocyte differentiation marker albumin (ALB) was enhanced more than 100 times (FIG. 18) and expressions of other differentiation markers (FOXA2, TAT and PCK2) were also enhanced about several ten times (FIG. 19).

(5) By transplantation, human blood vessels were connected with mouse blood vessels, and blood perfusion began early (2 days post-transplantation) (FIG. 20).

(6) Proliferation of human iPS cell-derived hepatocytes was confirmed (FIG. 21).

(7) Histological analysis of early samples (2 weeks post-transplantation) confirmed formation of albumin-positive cord-like structures. Formation of sinusoid-like structures was also confirmed (FIG. 22).

(8) In the coculture, when cell suspension was not seeded on Matrigel-solidified culture dish but embedded in Matrigel, or seeded on non-coated culture dish, or seeded on type I collagen-coated culture dish, no three-dimensional structures formed.

(9) In the coculture, when Hepatocyte Medium (Xeno-Tech) or BMP4- and FGF2-supplmented hepatocyte inducing medium (Hepatology, 51(1), 297-305, 2010) was used instead of the endothelial cell medium as a culture broth, enhanced expression of genes characteristic of liver buds (Alb, TTR, etc.) was not recognized.

[Example 5] Preparation of an Organ from Differentiated Organ Cell

Experimental Methods

Pancreatic β cell strain (MIN6) was cocultured with a vascular endothelial cell (human umbilical cord blood-derived vein endothelial cell) and an undifferentiated mesenchymal cell (human mesenchymal stem cell) mixed at 5:5-10:2. The pancreatic β cell strain (KO) and the vascular endothelial cell (EGFP) were individually labeled with fluorescence in advance. In the coculture, cell suspension was seeded on pre-solidified Matrigel (BD pharmingen) (stock gel or 2-fold dilution) in a culture dish. When cell suspension was embedded in Matrigel, or seeded on non-coated culture dish, or seeded on type I collagen-coated culture dish, no three-dimensional structures formed. As a culture broth, endothelial cell medium kit-2: EGM-2 BulletKit (product code CC-3162: Lonza) was used.

Cells were cultured for a short period of time (3-10 days) to prepare three-dimensional structures. The process of formation and the formed structures were observed under confocal microscope, and kinetic/static analyses of cell morphology and localization were performed.

The formed three-dimensional structure was transplanted into the living body of an immunodeficient mouse (NOD/SCID mouse (Sankyo Lab. Co., Tsukuba, Japan)). Macroscopic and confocal microscopic live observations were performed, followed by confirmation of engraftment/proliferation of cells and analysis of post-transplantation vascular maturation processes. Transplant samples (4 weeks post-transplantation) were recovered and analyzed histologically.

Experimental Results (1) Autonomous organization progressed only from cells, form a macroscopically observable three-dimensional structure on the following day (FIG. 22).

(2) At day 2 of culture, pancreatic β cell strain formed cell masses, around which human vessel-like luminal structures were confirmed (FIG. 23).

(3) By transplantation, human blood vessels were connected with mouse blood vessels, and blood perfusion started early after transplantation (FIG. 24).

(4) Pancreatic β cells proliferated to form cell masses and formed pancreatic islet-like structures (FIG. 25).

(5) Formation of vasculatures consisting of human cells was confirmed in the formed pancreatic islet-like structures (FIG. 26).

(6) Visualization of blood flow confirmed that sufficient blood perfusion re-started inside the pancreatic islet-like structure (FIG. 27).

(7) Histological analysis of transplant samples confirmed formation of insulin-positive islet-like structures. The formed structures had complex vasculatures in their inside and had a similar structure to normal mouse pancreatic islets (FIG. 28).

[Example 6] Generation of a Functional and Vascularized Human Liver from an Induced Pluripotent Stem Cell-Derived Organ Bud Transplant A critical shortage of donor organs for treating end-stage organ failure highlights the urgent need for generating organs from patient-derived induced pluripotent stem cells (hiPSCs)[1,2]. Despite many reports describing functional cell differentiation3-7, no studies have succeeded in generating a three-dimensional vascularized organ such as liver. The present inventors have successfully generated a vascularized and functional human liver from hiPSCs by transplantation of liver buds created in vitro (hiPSC-LBs). When endothelial and mesenchymal cells were added to promote organogenesis8, iPS cell-derived hepatic endoderm cells self-organized into three-dimensional hiPSC-LBs. Immunostaining and gene-expression analyses revealed a resemblance between in vitro-grown hiPSC-LBs and in vivo liver buds. Human vasculatures in hiPSC-LB transplants connected to the host blood vessels within 48 hours to start blood perfusion. It became clear that the formation of functional vasculatures stimulated the maturation of hiPSC-LBs into a tissue resembling the adult liver. Highly metabolic hiPSC-derived transplant tissue performed liver-specific functions such as human-type protein production and human-specific drug metabolism, without recipient's liver replacement9.10 Furthermore, mesenteric transplantation of hiPSC-LBs rescued a drug-induced lethal liver failure model. As far as the present inventors know, this is the first report demonstrating the generation of a functional human organ from pluripotent stem cells. Although efforts must be made to apply these techniques to clinical treatments, this proof-of-concept demonstration of organ-bud transplantation provides a promising new approach to regenerative medicine.

Since the discovery of embryonic stem cells in 1981, decades of laboratory studies have failed to generate a complex vascularized organ such as liver from pluripotent stem cells, giving rise to the prevailing belief that in vitro recapitulation of the complex interactions among cells and tissues during organogenesis is essentially impractical2.11. The present inventors challenged this idea by focusing on the earliest process of organogenesis, that is, cellular interactions during organ-bud development.

During early liver organogenesis, cells delaminate from the foregut endodermal sheet and form a three-dimensional liver bud (LB)[12]. Such large-scale morphogenetic changes depend on the exquisite orchestration of signals between endodermal, mesenchymal and endothelial progenitors before blood perfusion[8]. Based on these observations, the present inventors hypothesized that three-dimensional liver-bud formation can be recapitulated in vitro by culturing hepatic endoderm cells with endothelial and mesenchymal lineages (FIG. 29*a*). To examine this hypothesis, the present inventors first prepared hepatic endoderm cells from human iPSCs (hiPSC-Heps) by directed differentiation with gradual addition of inducing factors. As a result, approximately 80% of the treated cells expressed the hepatic marker HNF4A which is involved in cell fate determination (FIGS. 33 and 29*b*).

Next, to recapitulate early liver organogenesis, hiPSC-Hep cells were cocultured with stromal cell populations. Human umbilical vein endothelial cells (HUVECs) and human mesenchymal stem cells (hMSCs) were used unless stated otherwise, because of their primitive nature. Notably, though cells were plated in two-dimensional conditions, hiPSC-Hep cells self-organized into macroscopically visible three-dimensional cell clusters by their intrinsic organizing capacity within 24 hours after seeding (FIG. 29*c, d, e*). The presumed hiPSC-Hep derived liver buds (hiPSC-LBs) were mechanically stable and could be manipulated physically through transplantation operation. Development of vascular networks accompanied by exquisite bud formation of endothelial cells in hiPSC-LBs was visualized by using fluorescent protein-labeled cells (FIG. 29*c*). Further, by using a single donor umbilical cord-derived MSCs and HUVECs, hiPSC-LBs were homogeneously distributed (FIG. 34*a*, right). Quantitative polymerase chain reaction (qPCR) analysis revealed that cells in hiPSC-LBs had significantly increased transcription of early hepatic marker genes such as alpha-fetoprotein (AFP), retinol binding protein 4 (RBP4), transthyretin (TTR) and albumin (ALB)[5] (FIG. 34*d*). Interestingly, liver maturation of stromal cell-dependent hiPSC-Hep cells was retained to some extent even in coculture systems using Transwell medium (FIG. 29*f*). Microarray and qPCR analyses were performed to examine intermediary factors which induce liver maturation. Among stromal cell-specific gene groups, expressions of BMP4 and FGF2 were remarkably elevated in coculture systems with endothelial and mesenchymal cells (FIG. 35). Noggin and SU-5402, which are BMP- and FGF-specific signaling inhibitors, inhibited the differentiation promoting effect brought about by coculture with stromal cells. On the other hand, when BMP4 and FGF2 were added to hiPSC-Hep medium, a similar liver differentiation inducing effect was observed (FIG. 29*g, h*). These results suggest, as observed in animal experiments[13], that in addition to the direct cell-to-cell interactions, paracrine support by stromal cell-dependent humoral factors is partially responsible for early liver maturation through activation of FGF and BMP pathways.

Figure 30A:
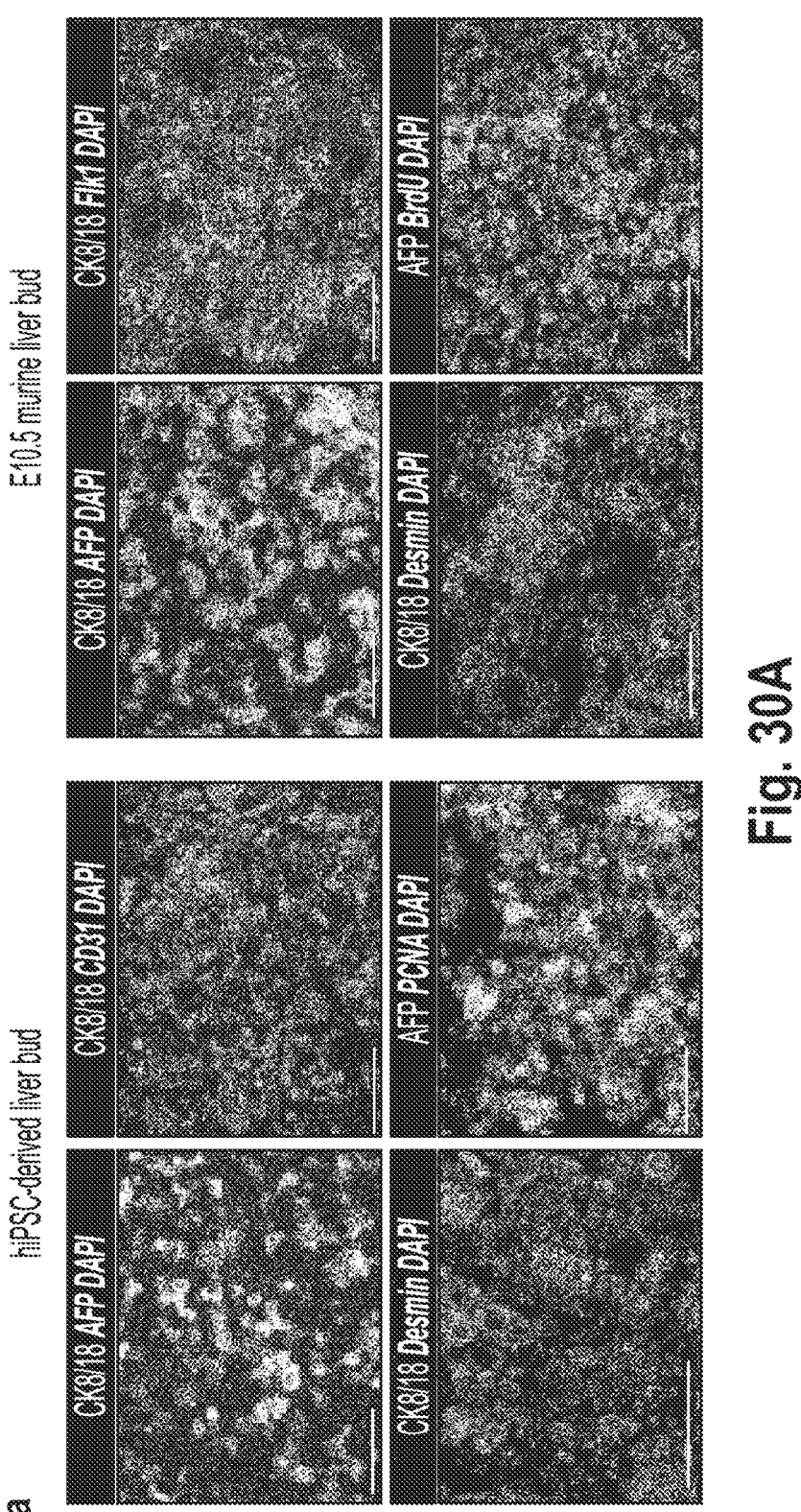

Unlike advanced livers as found in late pregnancy or post-natal mice, hiPSC-LBs were largely similar to E10.5 mouse LBs (mLBs) (FIG. 30*a*). Like mesenchymal and endothelial progenitor cells, hiPSC-LBs and E10.5 mLBs are composed of bipotential, proliferative hepatoblasts which express AFP[14, 15]. In hiPSC-LBs and E10.5 mLBs, 90% or more of the presumed liver cells expressed AFP, whereas no AFP expression was observed in E15.5 and E17.5 mLBs (FIG. 30*b*). Liver cells in hiPSC-LBs had a proliferating capacity comparable to that of E10.5 mLBs (FIG. 30*c*). Further, hiPSC-LBs were composed of mesenchymal and endothelial progenitor cells in similar proportions to those seen in E10.5 mLBs (FIG. 30*d, e*). To characterize gene expression, 83 genes that are serially upregulated during liver development were selected and their expressions were studied by microarray RNA profiling. It was described previously[16,17] that E10.5 mLBs correspond to human fetal liver of gestational week 3 to 4 (3-4 GW). Consistent with this, the gene expression patterns of the 83 genes in hiPSC-LBs were recognized to be in an appropriate differentiation stage, as compared with gene expressions in more advanced liver tissues derived from fetuses of 22-40 GW and adults (FIG. 30*f* and FIG. 36A-36E).

Haemodynamic stimulation is essential for liver-bud maturation[18]. To test whether hiPSC-LBs are capable of reconstituting completely functional liver tissue, liver buds were transplanted into a cranial observation window which enables repetitive imaging for a long term[19]. First, it was confirmed by using mouse liver bud-derived cells (mLB) in transplantation experiments that this model is capable of recapitulating the maturing process of LB (Supplementary Discussion; FIGS. 37 and 38). Further, in the culture, fetal liver cells having comparable LB (hFLC-LBs) forming capacity was used as a control (FIG. 34*a*). To track the in vivo fate of transplanted human cells, repeated live imaging of hiPSC-LB-derived tissues was performed at multiple time points. Notably, in vitro derived hiPSC-LBs connected quickly with host vasculatures within 48 hours of transplantation (FIG. 31*a, b* and FIG. 39). Infusion of fluorescein-conjugated dextran or Alexa 647-labeled mouse-specific CD31 antibody revealed that human blood vessels in the transplanted hiPSC-LBs connect with host vessels at the edge of the transplants. This result was also confirmed by whole mount immunostaining of explants (FIG. 31*c, d*; FIG. 40; FIG. 41*a, b*). Further, hiPSC-Heps transplanted without endothelial cells failed to vascularize and engraft, indicating that functional vessel formation was essential for the transplantation and expansion of hiPSC-LBs (FIG. 31*f* and FIG. 41). Human vessels stabilized by hMSC-derived perivascular cells remained for at least 180 days (FIG. 31*e, g*). Interestingly, the vascular networks of hiPSC-LB transplants were comparable in density to those of adult livers having a similar morphology. On the other hand, the vasculatures in the transplants composed of only HUVECs and hMSCs were less dense than those in hiPSC-LB transplants, though functional vessels were of similar diameter (approximately 12 μm) in both settings (FIG. 31*h, i*; FIG. 42; FIG. 43). Further, with the use of intravital imaging, it was found possible to estimate the state of differentiation based on the morphology of liver cells (FIG. 43*c* and Supplementary Discussion). Recently, results from detailed studies on genetically modified animals suggest that endothelial cells not only form passive conduits to deliver nutrients and oxygen but also establish an instructive vascular niche which stimulates liver organogenesis and regeneration through production of paracrine trophogens[8,20,21]. With such a transplantation model, it can be said that a unique intravital monitoring system even applicable to human tissue has been established for evaluating maturation and differentiation processes during organogenesis. Further studies are expected to elucidate the previously uncharacterized roles of human stromal cell strains during organogenesis which recapitulate physiological liver formation more precisely.

The LB transplants were examined histologically at day 60 post-transplantation. Similar to hFLC-LBs, hiPSC-LB transplants consisted of hepatic cord-like structures characteristic of adult liver (FIG. 32*a* and FIG. 44*a*). These structures were composed of cells expressing tight junction protein zona occludens 1 (ZO1), ALB and cytokeratin 8 and 18 (CK8/18) (FIG. 32*b*) and basement membrane containing collagen IV (FIG. 45*a*) which is normally found along the entire length of the sinusoid[22]. Further, the analysis revealed expression of asialoglycoprotein receptor 1 (ASGR1), a mature hepatocyte marker, and non-expression of AFP, an immature hepatocyte marker (FIG. 45*b* and FIG. 30*a*). Four months after transplantation, expression of Ki-67 (a proliferation marker) confirmed that proliferation terminated in most of the liver tissue constituting cells, just like hepato-cytes in normal liver (FIG. 44*b*). Transplant-derived cells had the ultrastructural features characteristic of mature hepa-tocytes, such as well-developed oval mitochondria, forma-tion of tight junctions, intracytoplasmic accumulation of glycogen and lipids, bile canaliculi, etc. (FIG. 46*b, c, d, e*).

Figure 47B:
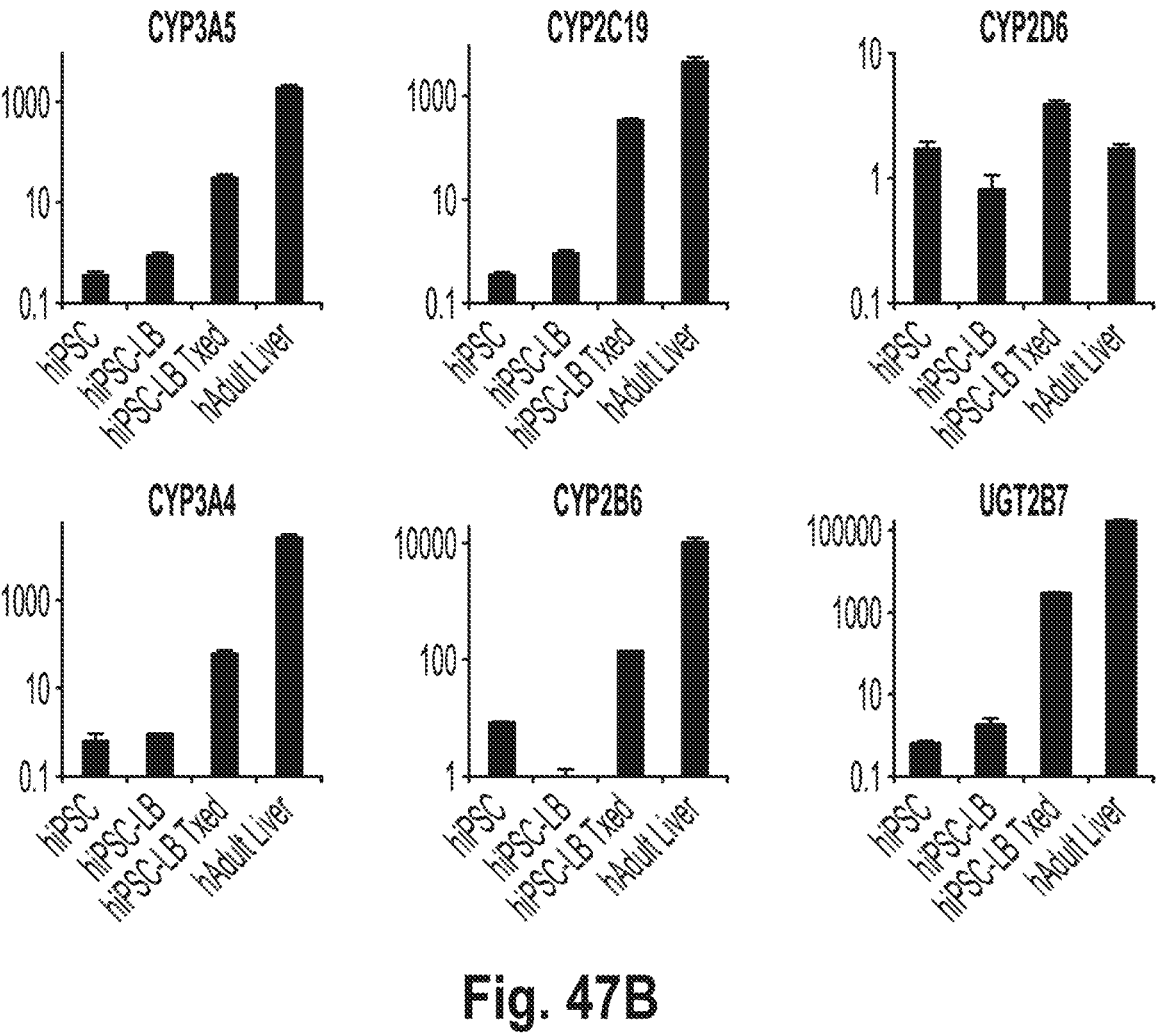

Analysis of sera from hiPSC-LB-transplanted mice con-firmed production and secretion of human-type ALB and A1 antitrypsin (AAT) (both are human proteins) (FIG. 32*e*). At day 60 post-transplantation, hiPSC-LBs were explanted and analyzed by qPCR. The results revealed significant liver maturation compared with in vitro-derived hiPSC-LBs (FIG. 47). Furthermore, to characterize the profiles of low molecu-lar weight metabolites such as the products of sugar, amino acid and nucleotide metabolism, metabolome analysis of hiPSC-LB transplants was performed, resulting in the detec-tion of 222 metabolites, including liver-specific metabolites such as taurocholic acid (FIG. 32F). These high metabolic profiles were similar to those of human adult liver rather than those of original hiPSCs (FIG. 48). Further, to analyze the drug metabolism activity that is a major function of the liver, the mice were challenged with ketoprofen[23] or debrisoquine[24,25], which are known to be metabolized dif-ferently in mice and humans. After the drug exposure, formation of human-specific metabolites was recognized in urine and serum samples collected from hiPSC-LB-trans-planted mice (FIG. 32*f, g, h* and Supplementary Discussion). This result shows that it is possible to predict drug metabo-lism profiles of humans by using the transplanted mouse and mimicking in vivo human physiological function. This is particularly striking, since conventional methods require high quality adult hepatocytes for transplantation into a host mouse bearing severely damaged liver[26,27]. It is very sig-nificant that, in future, human-type drug responsiveness could be precisely validated by using human iPS cells.

Towards clinical application in the future, the present inventors evaluated the possibility of a minimally invasive mesenteric transplantation model; the mesentery would be a more realistic target site than the cranium. When hiPSC-LBs were transplanted onto the mesentery covered with fibrin glue, human blood vessels connected with host vessels after a month and macroscopic observation confirmed the suc-cessful engraftment of transplanted LBs on mesentery (FIG. 49*a, b*). The hiPSC-LBs transplanted onto mesentery had higher functions in terms of protein production and drug metabolism than when they were transplanted into the cranium. As disclosed previously[28], importance of portal circulation was supported. Further, transplantation of hiPSC-LBs improved the survival of TK-NOG mice[29] after gancyclovir-induced liver failure compared with sham-op-erated mice (FIG. 32*i* and Supplementary Discussion). Thus, the present inventors have successfully induced a vascular-ized and functional human liver by transplanting in vitro hiPSCs-derived LBs.

Regenerative medicine using autologous pluripotent stem cells holds extremely great promise. However, clinical trials of cell transplantation, currently an important target of the stem-cell-based approach, have presented unsatisfactory results[30,31]. The present study has demonstrated that trans-plantation of organ buds is effective as a novel technique for preparing a three-dimensional, vascularized organ in vivo. These results highlight the enormous therapeutic potential of in vitro-grown organ-bud transplantation for treating organ failure.

Methods Summary For Examples 4-6

Hepatic early differentiation of hiPSCs was induced based on a protocol reported previously[5]. HUVECs and hMSCs (Lonza, Basel, Switzerland) were maintained in endothelial growth medium (EGM) (Lonza) or MSC growth medium (Lonza) at 37° C. in a humidified 5% $CO_2$ incubator. To generate human LBs in vitro, $1\times10^6$ hiPSC-derived hepatic cells, $0.8-1\times10^6$ HUVECs and $2\times10^5$ hMSCs were sus-pended in a mixture of EGM and hepatocyte culture medium (HCM) (Cambrex, Baltimoe, MD) [containing dexametha-sone (0.1 µM, Sigma-Aldrich, St Louis, MO), oncostatinM (10 ng/ml, R&D System, Minneapolis, MN), HGF (20 ng/ml, PromoKine) and SingleQuots (Lonza)] and plated on Matrigel (BD Biosciences, Bedford, MA, USA). After 4 to 6 days of culture, generated hiPSC-LBs were detached, collected and transplanted into a pre-formed cranial win-dow[19] of an immunodeficient mouse.

Methods

Cell culture and differentiation. TkDA3 human iPSC clone was kindly provided by Mr. Koji Eto and Mr. Hiromitsu Nakauchi. Undifferentiated hiPSCs were grown on mouse embryonic fibroblast cells as feeder cells. For endodermal differentiation, hiPSCs were seeded on a Matrigel-coated dish, transferred to RPMI1640 medium with 1% B27 with-out insulin and (100 ng/ml), and cultured for 5 to 6 days. For hepatic specification, hiPSC-derived endodermal cells were treated further with RPMI1640 containing hbFGF (10 ng/ml), hBMP4 (20 ng/ml) and 1% B27 for 3 to 4 days. Recombinant human activin A/EDF was kindly provided by Mr. Yuzuru Eto (Ajinomoto Co.). hFLCs (CS-ABI-3716; Applied Cell Biology Research Institute) were plated on collagen IV-coated 6-well plates (BD Biosciences) and cultured in the standard medium of the present inventors' lab (1:1 mixture of DMEM and F-12 (Sigma Aldrich) supple-mented with 10% FBS (Lot 7219F; ICN Biochemical, USA), 50 mmol/L HEPES (Wako Pure Chemical Industries, Japan), 2 mmol/L L-glutamine (Life Technologies Corpo-ration, USA), 50 mmol/L 2-mercaptoethanol (Sigma), 1× penicillin/streptomycin (Life Technologies), 10 mmol/L nicotinamide (Sigma), $1\times10^{-4}$ M Dexamethasone (Sigma) and 1 µg/ml insulin (Wako)). Human recombinant HGF (50 ng/ml) and EGF (20 ng/ml) (Sigma) were added before cultivation. HUVECs and hMSCs (Lonza) were maintained in endothelial growth medium or MSC growth medium (Lonza) at 37° C. in a humidified 5% $CO_2$ incubator.

Retroviral transduction. For live imaging, cells were infected with retroviruses expressing EGFP or Kusabira-Orange (KOFP) as described[19]. In brief, a retrovirus vector pGCDNsam IRES-EGFP or KOFP was transfected into 293 gp and 293 gpg packaging cells (kindly provided by Mr. Masafumi Onodera), in which viral particle production was induced using a tetracycline inducible system. Culture supernatants of retrovirus-infected cells were passed through a 0.45-µm filter (Whatman, GE Healthcare, Japan) and used immediately for infection. KOFP displays a major absorption wavelength maximum at 548 nm with a slight shoulder at 515 nm and emits a bright orange fluorescence with a peak at 561 nm[32].

Transplantation. In vitro-generated LBs were detached, col-lected and transplanted into a pre-formed cranial window of a severely immunodeficient (NOD/SCID) mouse (Sankyo Lab. Co., Tsukuba, Japan). The in vivo fate of transplanted cells was monitored by intravital imaging using a fluores-cence microscope (model BZ-9000; Keyence, Osaka, Japan) or the Leica TCS SP5 confocal microscope (Leica Micro-systems). For survival curves, TK-NOG mice (body weights <20 to 30 g) were used in this study (supplied by the Central Institute for Experimental Animals, Kanagawa, Japan)[29].

Ganciclovir (GCV, 50 mg/kg, intraperitoneal), a drug that is not toxic to human or mouse tissues, was administered to induce tissue-specific ablation of transgenic liver parenchymal cells at day 7 and 10 after a dozen hiPSC-LBs were transplanted on the mesentery. The mice were bred and maintained according to the Yokohama City University institutional guidelines for the use of laboratory animals.

Quantification of perfusion brought about by engrafted vessels. Tail vein injections of 1% tetramethylrhodamine-conjugated dextran (2,000,000 MW), fluorescein-isothio-cyanate-conjugated dextran (2,000,000 MW) and Texas-Red-conjugated dextran (70,000 MW, neutral) were used to identify vessel lumens (all from Invitrogen, Carlsbad, CA, USA). Confocal image stacks were acquired for the implanted vessels and dextran. Image projections were processed using MetaMorph Angiogenesis Module software (Molecular Devices, Union City, CA, USA). Total tubule length, the percentage of tubules per field and tube diameter were then logged automatically into an Excel spreadsheet.

Gene-expression analysis. Quantitative PCR analyses were conducted as described previously[33]. Total RNA of human fetal liver (Lot No. A601605) and human adult liver (Lot No. B308121) were obtained from Biochain Institute (Hayward, CA, USA).

Gene expression microarray and data analysis. Total RNA was prepared from hiPSC-derived cells/tissues (hiPSC, hiPSC-Def, hiPSC-Hep, hiPSC-IH, hiPSC-MH, hiPSC-LB, hiPSC-LB-Tx) using an RNeasy Mini Kit (Qiagen, Valencia, CA). Total RNA of human fetal liver (Lot No. A601605) and human adult liver (Lot No. B308121) were obtained from Biochain Institute (Hayward, CA, USA). cRNA was amplified, labeled using Low Input Quick Amp Labeling Kit (Agilent Technologies, Palo Alto, CA) and hybridized to 44K 60-mer oligomicroarray (Human Gene Expression 4×44K v2 Microarray Kit; Agilent Technologies) according to the manufacturer's instructions. Hybridized microarray slides were scanned with Agilent High-Resolution Microarray Scanner. Using Feature Extraction Software version 10.7.3.1 (Agilent Technologies), relative hybridization intensity and background hybridization value were calculated. According to the protocol recommended by Agilent Technologies and using flag standards in GeneSpring 11.5.1 Software, raw signal intensity and flag of each probe were calculated from hybridization intensity and spot information. Further, the row signal intensity of samples was log2 converted and normalized with quantile algorithm. For all samples, probes were selected except for "compromised" flag. As a result, 34,183 probes were obtained as detected genes. Further, expression data for 26,153 genes were focused at gene level. Heat maps were prepared by Gene-Spring. Normalized intensities were loaded and scaling-adjusted with the distance from the median of each probe. Samples and genes were classified using a hierarchical clustering method with Euclidean distance. To evaluate differences in gene expression patterns in hiPSCs of various stages, expression changes in the selected 83 genes were analyzed. These genes were identified in a previous study of the present inventors using microarray analyses of mouse liver cells of various developmental stages and human liver tissues of two different stages. Of all genes, 83 genes were selected as liver-specific genes because their expressions increased continuously during both murine and human liver development.

ELISA. Blood samples were allowed to clot in a centrifuge tube (approximately 5 min) at room temperature, loosened from the sides of the tube and kept at 4° C. (melting ice) for 20 min. Clotted blood was centrifuged for 10 to 15 min at 400 g, 4° C. and the serum fraction was removed, with care being taken to exclude erythrocytes or clotted materials. Human ALB and AAT in the mouse serum samples were measured using Human Albumin ELISA Quantitation Kit (Bethyl Laboratories Inc., Montgomery, TX, USA) and human alpha 1-antitrypsin ELISA Quantitation Kit (Gen-Way Biotech Inc., Inc., San Diego, CA, USA) according to the manufacturers' instructions.

Whole mount immunostaining. Mice were perfused with 4% paraformaldehyde (PFA) in PBS through cardiac puncture. The cover-glass forming the cranial window was removed, and the transplants (approximately 300 μm thick) were resected and placed in 4% PFA for 1.5 hours on ice. For immunostaining, fixed collagen gels were washed three times in PBS (10 min each), blocked with 3% BSA/0.1% Triton X-100 for 1 hour, incubated with primary antibodies at 4° C. overnight, followed by three 10-min washes in PBS/0.1% Triton X-100. The sample was incubated with secondary antibodies at 4° C. overnight, followed by three 10-min washes in PBS/0.1% Triton X-100. Tissue samples were counterstained with DAPI and mounted on glass slides in mounting media (Vector Laboratories, USA), under a cover slip. The following primary antibodies were used: mouse anti-human ZO1, mouse anti-human CD31 and rat anti-mouse CD31 (BD Biosciences), rabbit anti-mouse collagen IV (Millipore, USA) and desmin (Dako Corporation, Carpinteria, CA). Immunostaining was analyzed using the Leica TCS SP5 confocal microscope.

Tissue processing and immunostaining. Tissues were fixed overnight at 4° C. in 4% PFA, processed, and embedded in paraffin. Transverse sections (4 μm) were placed on MAS-coated slides (Matsunami, Osaka, Japan) for immunostaining with haematoxylin and eosin (HE) or standard histological staining. Immunostaining was preceded by autoclave antigen retrieval in citrate buffer (pH 6.0). The primary antibodies used were anti-human: CD31, smooth muscle actin, AFP, CK8/18 (all from Dako Corporation) and ALB (BD Biosciences). Tissue sections were incubated with secondary antibody Alexa Fluor (Life Technologies) for 1 hour at room temperature, followed by DAPI (Sigma) nuclear staining. The images were acquired using LSM510 laser scanning microscope (Carl Zeiss Co., Germany).

Statistical analysis. Data are expressed as the means±S.D. from three or six independent experiments. Comparisons between three or four groups were analyzed using Kruskal-Wallis test by ranks, and post-hoc comparisons were performed using Mann-Whitney U-test with Bonferroni correction. Two-tailed P values of <0.05 were considered significant.

REFERENCES

Cai, J. et al. Directed differentiation of human embryonic stem cells into functional hepatic cells. Hepatology 45, 1229-1239, (2007).

Chen, A. A. et al. Humanized mice with ectopic artificial liver tissues. Proc Natl Acad Sci U S A 108, 11842-11847, (2011).

Collardeau-Frachon, S. & Scoazec, J. Y. Vascular development and differentiation during human liver organogenesis. Anat Rec (Hoboken) 291, 614-627, (2008).

Ding, B. S. et al. Inductive angiocrine signals from sinusoidal endothelium are required for liver regeneration. Nature 468, 310-315, (2010).

Ding, B. S. et al. Endothelial-derived angiocrine signals induce and sustain regenerative lung alveolarization. Cell 147, 539-553, (2011).

Dudley, S. C., Jr. Beware of cells bearing gifts: cell replacement therapy and arrhythmic risk. Circ Res 97, 99-101, (2005).

Espejel, S. et al. Induced pluripotent stem cell-derived hepatocytes have the functional and proliferative capabilities needed for liver regeneration in mice. J Clin Invest 120, 3120-3126, (2010).

Gouysse, G. et al. Relationship between vascular development and vascular differentiation during liver organogenesis in humans. J Hepatol 37, 730-740, (2002).

Hasegawa, M. et al. The reconstituted 'humanized liver' in TK-NOG mice is mature and functional. Biochem Biophys Res Commun 405, 405-410, (2011).

Ishizaki, T. et al. Pharmacokinetics of ketoprofen following single oral, intramuscular and rectal doses and after repeated oral administration. Eur J Clin Pharmacol 18, 407-414, (1980).

Jiang, H. et al. Parkin controls dopamine utilization in human midbrain dopaminergic neurons derived from induced pluripotent stem cells. Nat Commun 3, 668, (2012).

Jung, J., Zheng, M., Goldfarb, M. & Zaret, K. S. Initiation of mammalian liver development from endoderm by fibroblast growth factors. Science 284, 1998-2003, (1999).

Kamimura, H. et al. Assessment of chimeric mice with humanized liver as a tool for predicting circulating human metabolites. Drug Metab Pharmacokinet 25, 223-235, (2010).

Katoh, M. et al. In vivo drug metabolism model for human cytochrome P450 enzyme using chimeric mice with humanized liver. J Pharm Sci 96, 428-437, (2007).

Klein, A. S. et al. Organ donation and utilization in the United States, 1999-2008. Am J Transplant 10, 973-986, (2010).

Kobayashi, T. et al. Generation of rat pancreas in mouse by interspecific blastocyst injection of pluripotent stem cells. Cell 142, 787-799, (2010).

Kobayashi, S. et al. Reconstruction of human elastic cartilage by a CD44+CD90+ stem cell in the ear perichondrium. Proc Natl Acad Sci U S A 108, 14479-14484, (2011).

Koike, N. et al. Tissue engineering: creation of long-lasting blood vessels. Nature 428, 138-139, (2004).

Korzh, S. et al. Requirement of vasculogenesis and blood circulation in late stages of liver growth in zebrafish. BMC Dev Biol 8, 84, (2008).

Kriks, S. et al. Dopamine neurons derived from human ES cells efficiently engraft in animal models of Parkinson's disease. Nature 480, 547-551, (2011).

Kroon, E. et al. Pancreatic endoderm derived from human embryonic stem cells generates glucose-responsive insulin-secreting cells in vivo. Nat Biotechnol 26, 443-452, (2008).

Lee, C. S., Friedman, J. R., Fulmer, J. T. & Kaestner, K. H. The initiation of liver development is dependent on Foxa transcription factors. Nature 435, 944-947, (2005).

Martinez-Hernandez, A. The hepatic extracellular matrix. I. Electron immunohistochemical studies in normal rat liver. Lab Invest 51, 57-74, (1984).

Matsumoto, K., Yoshitomi, H., Rossant, J. & Zaret, K. S. Liver organogenesis promoted by endothelial cells prior to vascular function. Science 294, 559-563, (2001).

Mizuguchi, T., Mitaka, T., Katsuramaki, T. & Hirata, K. Hepatocyte transplantation for total liver repopulation. J Hepatobiliary Pancreat Surg 12, 378-385, (2005).

Rautio, A., Kraul, H., Kojo, A., Salmela, E. & Pelkonen, O. Interindividual variability of coumarin 7-hydroxylation in healthy volunteers. Pharmacogenetics 2, 227-233, (1992).

Sanal, M. G. Future of liver transplantation: non-human primates for patient-specific organs from induced pluripotent stem cells. World J Gastroenterol 17, 3684-3690, (2011).

Sanuki, S. et al. A new red fluorescent protein that allows efficient marking of murine hematopoietic stem cells. J Gene Med 10, 965-971, (2008).

Sekiya, S. & Suzuki, A. Direct conversion of mouse fibroblasts to hepatocyte-like cells by defined factors. Nature 475, 390-393, (2011).

Si-Tayeb, K., Lemaigre, F. P. & Duncan, S. A. Organogenesis and development of the liver. Dev Cell 18, 175-189, (2010).

Yu, A. M., Idle, J. R. & Gonzalez, F. J. Polymorphic cytochrome P450 2D6: humanized mouse model and endogenous substrates. Drug Metab Rev 36, 243-277, (2004).

Zhao, R. & Duncan, S. A. Embryonic development of the liver. Hepatology 41, 956-967, (2005).

Supplementary Methods

HUVEC MSC isolation. Umbilical cord samples were obtained following the approved guidelines set forth by the ethical committee at Yokohama City University (Approval No. 13120510008). HUVECs and MSCs were simultaneously isolated from the umbilical cord as previously described[2].

smFLC isolation. E13.5 mFLCs isolated from C57BL/6-Tg CAG::EGFP (SLC, Japan) were mechanically dissociated by pipetting in Dulbecco's modified Eagle's medium (DMEM) containing 10% foetal bovine serum (FBS) (JRH Bioscience, USA). Liver cells were separated from non-parenchymal cells by several rounds of low-speed centrifugation (690 rpm/4° C. for 1 min). Dissociated cells were passed twice through a 70 μm cell strainer (Falcon, USA) to obtain single cells Quantification of engrafted hepatocyte morphology. Intra-vital confocal images were processed with IN Cell Investigator software (GE Healthcare, Fairfield, CT, USA), and the states of hepatocyte differentiation were classified using a "form factor" (standard estimation of roundness which correlates perimeter with area). The thus measured values vary from 0 to 1, with 1 being taken as a complete circle.

Acquisition of metabolome profiles. At day 60 post-transplantation, hiPSC-LB transplants (n=3) were harvested and analyzed. CE-TOFMS was carried out using an Agilent CE Capillary Electrophoresis System equipped with an Agilent 6210 Time of Flight mass spectrometer, Agilent 1100 isocratic HPLC pump, Agilent G1603A CE-MS adapter kit, and Agilent G1607A CE-ESI-MS sprayer kit (Agilent Technologies, Waldbronn, Germany). The system was controlled by Agilent G2201AA ChemStation software version B.03.01 for CE (Agilent Technologies, Waldbronn, Germany). Cationic metabolites were analyzed with a fused silica capillary (50 μm i.d.×80 cm total length), with Cation Buffer Solution (Human Metabolome Technologies) as an electrolyte. The sample was injected at a pressure of 50 mbar for 10 sec (approximately 10 nl). The applied voltage was set at 27 kV. Electrospray ionization-mass spectrometry (ESI-MS) was conducted in the positive ion mode, and the capillary voltage was set at 4,000 V. The spectrometer was scanned from m/z 50 to 1,000. Other conditions were the same as in the cation analysis[3].

Anionic metabolites were analyzed with a fused silica capillary (50 μm i.d.×80 cm total length), with Anion Buffer Solution (Human Metabolome Technologies) as an electrolyte. The sample was injected at a pressure of 50 mbar for 25 sec (approximately 25 nl). The applied voltage was set at 30 kV. ESI-MS was conducted in the negative ion mode, and the capillary voltage was set at 3,500 V. The spectrometer was scanned from m/z 50 to 1,000. Other conditions were the same as in the anion analysis[4].

Raw data obtained by CE-TOFMS were processed with the automatic integration software MasterHands[5]. Peak information including m/z, migration time (MT) and area was obtained. Peak area was converted to relative peak area according to the equation given below. Each peak was aligned according to similar migration time on CE and m/z value determined by TOFMS.

Relative peak Area =

Metabolite Peak Area/(Internal Standard Peak Area × Sample Amount)

The metabolic pathway map was provided using public-domain software, VANTED: Visualisation and Analysis of Networks containing Experimental Data[6].

Drug metabolizing activity. Ketoprofen (15 mg/kg) was administered intravenously to the NOD/SCID mice into which hiPSC-LBs were transplanted through the cranial window (n=3). Sham-operated NOD/SCID mice were used as a control. Urine samples (0-2 hr) were collected in 0.5 M acetate buffer (pH 5.0). After adding 1 N KOH, the urine samples were incubated at 80° C. for 3 hours and then neutralized with an equal volume of 1 N HCl. After adding acetonitrile containing 1% acetic acid, the mixture was centrifuged (15000 rpm, 4° C., 5 min).

The supernatant was subjected to liquid chromatograpy-tandem mass spectrometry (LC/MS/MS). LC-20A series (Shimadzu, Kyoto, Japan) equipped with Inertsil ODS-3 column (GL Sciences, Tokyo, Japan) was used for liquid chromatography (LC) experiments. Chromatographic separation was achieved on Inertsil ODS-3 column (5 μm, 4.6×150 mm I.D.; GL Sciences Inc., Tokyo, Japan). The column temperature was maintained at 40° C. A mobile phase consisting of 0.1% acetic acid (solvent A) and 0.1% acetic acid-containing acetonitrile (solvent B) was pumped in at a flow rate of 0.5 mL/min according to the following gradient schedule: a linear gradient from 25 to 80% solvent B (0-15 min), 80% solvent B (15-25 min), a linear gradient from 80 to 25% solvent B (25-26 min), and 25% solvent B (26-35 min). The LC was connected to a 4000 Q Trap system (AB SCIEX, Foster City, CA), and operated in negative electrospray ionization mode. The turbo gas was maintained at 600° C.

Parent and/or fragment ions were filtered in the first quadrupole and dissociated in the collision cell using nitrogen as the collision gas. Ion spray voltage was set at −4500 V, and the analyzed m z transitions (Q1/Q3) for ketoprofen and 1-hydroxyketoprofen were 253.1/209.3 and 269.1/209.3, respectively.

Debrisoquine (2 mg/kg) was orally administered to NOD/SCID mice transplanted with hiPSC-LB intracranially (n=3) and mesentirically (n=3). Sham-operated NOD/SCID mice were used as a control. Blood samples were collected 0.5, 1, 2 and 8 hours after administration, and heparin-Na was added. Plasma was centrifugally separated from blood. Internal standard (niflumic acid 1 μM) and methanol solution (100 μL) were added to 5 μL of the plasma and centrifuged (15000 rpm, 4° C., 5 min). The supernatant was subjected to LC/MS/MS. An Acquity UltraPerformance LC system (Waters, Milford, MA, USA) equipped with an Aquity UPLC BEH C18 column (Waters, Milford, MA, USA) was used for LC experiments. Chromatographic separation was achieved on Acquity UPLC BEH C18 (1.7 μm, 2.1×50 mm I.D.; Waters, Milford, MA, USA). The column temperature was maintained at 40° C. A mobile phase consisting of 10 mM ammonium acetate (solvent A) and acetonitrile (solvent B) was pumped in at a flow rate of 0.8 mL/min according to the following gradient schedule: 0% solvent B (0-0.2 min), a linear gradient from 0 to 30% solvent B (0.2-0.3 min), a linear gradient from 30 to 60% solvent B (0.3-0.85 min), 60% solvent B (0.85-1.15 min), a linear gradient from 60 to 100% solvent B (1.15-1.16 min), and 100% solvent B (1.16-1.5 min). The LC was connected to API4000 system (AB SCIEX, Foster City, CA) and operated in positive electrospray ionization mode. The turbo gas was maintained at 450° C. Parent and/or fragment ions were filtered in the first quadrupole and dissociated in the collision cell using nitrogen as the collision gas. Ion spray voltage was set at 5000 V and the analyzed m/z transitions (Q1/Q3) for 4-hydroxydebrisoquine and internal standard were 192.6/132.1 and 283.2/245.4, respectively.

Liver injury model. To evaluate the therapeutic potential of the transplantation strategy of the present inventors, Alb-TRECK/SCID mice were used for liver injury studies. Alb-TRECK/SCID mice were kindly provided by Hiromichi Yonekawa and Kunie Matsuoka (Tokyo Metropolitan Institute of Medical Science). This transgenic strain expresses HBEGF from ALB enhancer/promoter and develops fulminant hepatitis following administration of a small amount of diphtheria toxin (DT)[7]. hFLCs-LBs were transplanted into the mesentery covered with fibrin glue. At day 2 after transplantation, 1.5 μg/kg DT was infused via the tail vein to trigger severe liver injury. Survival was compared between transplanted and non-transplanted mice.

Supplementary Discussion

Feasibility of Cranial Window Model for
Functional Liver Tissue Generation

Detailed procedures for cranial window preparation were previously described[8]. The present inventors assessed the feasibility of cranial window to study liver cell maturation using transplants of EGFP-expressing E13.5 murine foetal liver cells (mFLCs). A section of mFLCs embedded in collagen/fibronectin gel was cut out and placed at the center of the cranial window. The window was then sealed with an 8-mm cover glass which was adhered to the bone using a histocompatible cyanoacrylate glue. Intravital fluorescence microscopy imaging showed a successful engrafting of transplanted mFLCs and a formation of functional vascular networks within the transplant (FIG. 21a). The transplanted tissue extensively differentiated into tissues resembling hepatic cords, sinusoids and bile ducts, all being characteristic of adult livers and not of donor E13.5 LBs (FIG. 21b). Liver tissue reconstitution by mFLCs was enhanced by addition of HGF and EGF, which are known to stimulate hepatic stem/progenitor cell expansion (FIG. 22)[9,10]. Thus, it was suggested that this transplantation approach provides a useful intravital monitoring system for evaluating LB cell maturation and differentiation.

Intravital Evaluation of Human Liver Cell Maturation

In the process of normal liver development, the morphology of liver cell changes from a round shape into a cobblestone-like shape[11]. This change can be easily visualized by cytokeratin immunostaining (FIG. 16a, left). Using IN Cell Investigator software, the present inventors have found that the roundness (form factor) of mouse liver cells decreases from 0.833±0.18 at E13.5 to 0.568±0.16 at postnatal week 8. Similarly, intravital imaging of single cell morphology revealed that the roundness of transplanted EGFP-labeled hFLCs changes from 0.93±0.07 at day 0 to 0.512±0.13 at day 30 post-transplantation (FIG. 27c, right). Consistent with these observations, enzyme-linked immunosorbent assay (ELISA) showed the occurrence of human albumin production at day 30 post-transplantation and thereafter (FIGS. 16c and d). Therefore, intravital monitoring of cell morphology can be an indicator for predicting the state of in vivo liver cell differentiation.

Detection of Human Specific-Drug Metabolism

The present inventors assessed the human specific-drug metabolism function using ketoprofen (KTP). KTP is primarily metabolized by cytochrome P450s in mice to produce 1-hydroxyketoprofen (OH-KTP)[12], while in humans KTP is mainly metabolized by UDP-glucuronosyltransferase (UGT) to produce ketoprofen glucuronide (KTP-G)[13].

Liver-humanized mice are a useful tool for studying human specific-drug metabolism. The human specific-drug metabolism function in liver-humanized mice was previously reported using high quality adult hepatocytes and immunodeficient mice bearing severely damaged liver. It was observed that UGT facilitated KTP glucuronidation after administration of KTP and that KTP was metabolized to KTP-G by hydrolysis. The KTP/OH-KTP peak area ratio was calculated and compared between hydrolysis and non-hydrolysis samples. The fold increase of the KTP/OH-KTP peak area ratio suggests the formation of KTP-G in samples. The fold increases in the urine of NOD/SCID mice with transplanted hiPSC-LBs and control mice were 11.8±5.2 and 2.3±0.7, respectively, suggesting that KTP glucuronidation (a human specific-drug metabolism function) was observed in hiPSC-LBs-transplanted NOD/SCID mice.

Debrisoquine, which serves as a common phenotyping reagent for human CYP2D6, is metabolized to 4-hydroxydebrisoquine (4-OHDB) in humans but negligible in mice. Importantly, human CYP2D6 is involved in the metabolism of 25% of known drugs and, due to its high number of polymorphisms, contributes to pronounced inter-individual variability. Following the oral administration of debrisoquine, the plasma concentration of 4-OHDB in the mesenterically or cranially transplanted group is higher than that in the sham-operated group, reflecting the production of a human specific-drug metabolite.

Establishment of Mesenteric Transplantation Model of hFLC- or hiPSC-LB Towards Clinical Application Cranial window model is not a very efficient method for organ bud transplantation because it is highly invasive.

Therefore, if clinical application is assumed, development of a less invasive transplantation method is necessary. In addition, the transplantable volume is not sufficient to reverse hepatic failure. Hence, the present inventors attempted to examine the possibility of a minimally invasive mesenteric transplantation model with clinical relevance because portal blood flow was considered to be important for improvement of hepatic functions. Consistent with the expectations of the present inventors, a recent report showed that the intraperitoneal site could support human adult hepatocyte engraftment and maintenance of hepatic functions, presumably due to host vessel recruitment from mesenteric blood flow[15]. In vitro-grown hFLC-LBs or hiPSC-LBs were transplanted on the mesentery (FIG. 33a).

Stimulation by ⅔ Partial Hepatectomy

To determine whether hepatic cell maturation in hiPSC-LB transplant can be promoted by regenerative factors such as HGF, ⅔ partial hepatectomy (PH) was performed at day 7 post mesenteric transplantation. Following the ⅔ PH, production of human albumin was elevated to 121 ng/ml in the ⅔ PH group from 82.1 ng/ml in a sham-operated group at day 30 post surgery (FIG. 33c). These results suggested that hiPSC-Heps are capable of responding to regenerative stimuli after 2/3 PH, presumably because of extensive hepatocyte proliferation and maturing in hiPSC-LB transplants.

Reversal of Liver Failure Using hFLC-LB Mesenteric Transplantation

To evaluate the therapeutic potential of the present inventors' strategy, in vitro-grown hFLC-LBs were transplanted on the mesentery sealed with fibrin glues. As a liver injury model, transgenic immunodeficient mice expressing human HB-EGF precursor under the control of a liver cell-specific albumin promoter were used. These mice, called toxin receptor-mediated cell knockout/severe combined immunodeficient (TRECK/SCID) mice, develop fulminant hepatitis upon administration of a small amount of diphtheria toxin (DT)[7]. DT agent was infused via tail vein at a dose of 1.5 μg/kg at day 2 post-transplantation. Survival curves revealed that all of the TRECK/SCID mice without transplantation died within 10 days. In contrast, 28% of the hFLC-LB transplanted TRECK/SCID mice survived for more than 40 days, indicating the therapeutic potential of the inventors' proof-of-concept (FIG. 32d). However, though this transplant model worked to some extent, it does not achieve a high rescue rate because DT is also toxic to human cells. Therefore, the present inventors adopted a TK-NOG mouse as immunodeficient liver injury model because administration of GCV, which is not toxic to human tissues, induces tissue-specific removal of transgenic liver parenchymal cells at appropriate timing. In this model, the present inventors removed host liver cells at days 7 and 10 post-transplantation at which time transplants are likely to engraft successfully through formation of functional human vascular networks.

All publications, patents and patent applications cited herein are incorporated herein by reference in their entirety. U.S. Pat. No. 11,326,150, and Patent Application Publication Nos. 2017-0159024 and 2020-0362315 are incorporated herein by reference in their entirety.

INDUSTRIAL APPLICABILITY

The present disclosure is applicable to regenerative medicine and drug discovery screening. Tissues and organs prepared according to the method of the present disclosure can be used for drug discovery screening and the like. Therefore, the present disclosure is applicable to industries such as pharmaceutical industry.

The invention claimed is:

1. An organ bud comprising iPSC-derived hepatocytes, vascular cells, and mesenchymal cells, wherein the hepatocytes are HNF4A positive.

2. The organ bud of claim 1, wherein the organ bud is vascularized.

3. The organ bud of claim 1, wherein the vascular cell includes a vascular endothelial cell.

4. The organ bud of claim 1, wherein the only cells cocultured to prepare the organ buds are the iPSC-derived hepatocytes, the vascular cells, and the mesenchymal cells.

5. The organ bud of claim 1, wherein the mesenchymal cell comprises a differentiated cell.

6. The organ bud of claim 1, wherein the mesenchymal cell comprises an undifferentiated cell.

7. A method of preparing the organ bud of claim 1, the method comprising culturing the iPSC-derived hepatocytes together with the vascular cells, and the mesenchymal cells.

8. The method of claim 7, wherein the iPSC-derived hepatocytes are cultured in a medium for culturing vascular cells, together with the mesenchymal cells.

9. The method of claim 7, wherein the iPSC-derived hepatocytes are plated on a gel and cultured together with the vascular cells, and the mesenchymal cells.

10. A method of transplanting an organ bud, comprising transplanting the organ bud of claim 1 into a human or a non-human animal.

11. The method of claim 10, wherein the site of transplantation of the organ bud comprises at least one selected from the group consisting of intracranial space, mesenteric space, liver, spleen, kidney, kidney subcapsular space, and supraportal space.

12. A method of regeneration or function recovery of a tissue or an organ, comprising transplanting the organ bud of claim 1 into a human or a non-human animal, wherein the organ bud is transplanted into at least one site selected from the group consisting of intracranial space, mesenteric space, kidney subcapsular site, and kidney.

13. A method of preparing a non-human chimeric animal, comprising transplanting the organ bud of claim 1 into a non-human animal, wherein the organ bud is transplanted into at least one site selected from the group consisting of intracranial space, mesenteric space, kidney subcapsular site, and kidney.

14. An organ bud comprising iPSC-derived transitional hepatic endoderm cells, vascular cells, and mesenchymal cells, wherein the iPSC-derived transitional hepatic endoderm cells are TBX3 positive and ADRA1B positive.

15. A method of regeneration or function recovery of a tissue or an organ, comprising transplanting the organ bud of claim 1 into a human or a non-human animal, wherein the organ bud is transplanted into liver or spleen.

16. A method of preparing a non-human chimeric animal, comprising transplanting the organ bud of claim 1 into a non-human animal, wherein the organ bud is transplanted into liver or spleen.

* * * * *